US007993880B2

(12) United States Patent
Willis et al.

(10) Patent No.: US 7,993,880 B2
(45) Date of Patent: *Aug. 9, 2011

(54) PRECIRCLE PROBE NUCLEIC ACID AMPLIFICATION METHODS

(75) Inventors: Thomas D. Willis, San Francisco, CA (US); Paul Hardenbol, Los Altos, CA (US); Maneesh Jain, Menlo Park, CA (US); Viktor Stolc, Cupertino, CA (US); Mostafa Ronaghi, Palo Alto, CA (US); Ronald W. Davis, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/709,319

(22) Filed: Feb. 19, 2010

(65) Prior Publication Data

US 2010/0330619 A1 Dec. 30, 2010

Related U.S. Application Data

(63) Continuation of application No. 10/826,633, filed on Apr. 15, 2004, now Pat. No. 7,700,323, which is a continuation of application No. 09/999,362, filed on Oct. 24, 2001, now Pat. No. 6,858,412.

(60) Provisional application No. 60/242,901, filed on Oct. 24, 2000.

(51) Int. Cl.

| | |
|---|---|
| ***C12P 19/34*** | (2006.01) |
| ***C07H 21/02*** | (2006.01) |
| ***C07H 21/04*** | (2006.01) |
| ***C12Q 1/68*** | (2006.01) |

(52) U.S. Cl. .................... 435/91.1; 435/91.2; 435/6.12; 536/24.3; 536/23.1

(58) Field of Classification Search ........................ None
See application file for complete search history.

(56) References Cited

U.S. PATENT DOCUMENTS

| | | | |
|---|---|---|---|
| 4,876,187 | A | 10/1989 | Duck |
| 4,883,750 | A | 11/1989 | Whiteley |
| 5,011,769 | A | 4/1991 | Duck |
| 5,035,996 | A | 7/1991 | Hartley |
| 5,130,238 | A | 7/1992 | Malek |
| 5,149,625 | A | 9/1992 | Church |
| 5,185,243 | A | 2/1993 | Ullman |

(Continued)

FOREIGN PATENT DOCUMENTS

EP 0303459 2/1989

(Continued)

OTHER PUBLICATIONS

Porreca, et al., "Multiplex amplification of large sets of human exons," *Nature Methods*, 4: 931-936 (Nov. 1, 2007, Epub Oct. 14, 2007).

(Continued)

*Primary Examiner* — Mark Staples
(74) *Attorney, Agent, or Firm* — Morse, Barnes-Brown & Pendleton, PC; Lisa M. Treannie, Esq.

(57) ABSTRACT

The invention is directed to novel methods of multiplexing nucleic acid reactions, including amplification, detection and genotyping. The invention relies on the use of precircle probes that are circularized in the presence of the corresponding target nucleic acids, cleaved, and then amplified.

6 Claims, 18 Drawing Sheets

U.S. PATENT DOCUMENTS

| | | | |
|---|---|---|---|
| 5,403,711 A | 4/1995 | Walder | |
| 5,409,818 A | 4/1995 | Davey | |
| 5,426,180 A | 6/1995 | Kool | |
| 5,455,166 A | 10/1995 | Walker | |
| 5,473,060 A | 12/1995 | Gryaznov | |
| 5,494,810 A | 2/1996 | Barany | |
| 5,541,311 A | 7/1996 | Dahlberg | |
| 5,571,639 A | 11/1996 | Hubbell | |
| 5,573,907 A | 11/1996 | Carrino | |
| 5,614,402 A | 3/1997 | Dahlberg | |
| 5,635,400 A | 6/1997 | Brenner | |
| 5,660,988 A | 8/1997 | Duck | |
| 5,679,524 A | 10/1997 | Nikiforov | |
| 5,719,028 A | 2/1998 | Dahlberg | |
| 5,763,175 A | 6/1998 | Brenner | |
| 5,830,711 A | 11/1998 | Barany | |
| 5,843,669 A | 12/1998 | Kaiser | |
| 5,846,717 A | 12/1998 | Brow | |
| 5,846,719 A | 12/1998 | Brenner | |
| 5,854,033 A | 12/1998 | Lizardi | |
| 5,866,337 A | 2/1999 | Schon | |
| 5,871,921 A | 2/1999 | Landegren | |
| 5,876,924 A | 3/1999 | Zhang | |
| 5,942,391 A | 8/1999 | Zhang | |
| 5,952,174 A | 9/1999 | Nikiforov | |
| 5,952,176 A | 9/1999 | McCarthy | |
| 5,981,176 A | 11/1999 | Wallace | |
| 6,027,889 A | 2/2000 | Barany | |
| 6,183,960 B1 | 2/2001 | Lizardi | |
| 6,187,575 B1 | 2/2001 | Sobek | |
| 6,210,884 B1 | 4/2001 | Lizardi | |
| 6,221,603 B1 | 4/2001 | Mahrani | |
| 6,228,580 B1 | 5/2001 | Blumenfeld | |
| 6,235,472 B1 | 5/2001 | Landegren | |
| 6,268,148 B1 | 7/2001 | Barany | |
| 6,355,431 B1 | 3/2002 | Chee | |
| 6,458,530 B1 | 10/2002 | Morris | |
| 6,506,594 B1 | 1/2003 | Barany | |
| 6,558,928 B1 | 5/2003 | Landegren | |
| 6,852,487 B1 | 2/2005 | Barany | |
| 7,700,323 B2 | 4/2010 | Willis et al. | |
| 2003/0104436 A1 | 6/2003 | Morris | |
| 2003/0207295 A1 | 11/2003 | Gunderson et al. | 435/6 |
| 2003/0215821 A1 | 11/2003 | Gunderson et al. | |
| 2004/0146901 A1 | 7/2004 | Morris | |
| 2005/0026180 A1 | 2/2005 | Willis et al. | |
| 2005/0100893 A1 | 5/2005 | Gunderson et al. | |

FOREIGN PATENT DOCUMENTS

| | | |
|---|---|---|
| EP | 0320308 B1 | 11/1993 |
| EP | 0336731 B1 | 5/1994 |
| EP | 0439182 B1 | 4/1996 |
| EP | 0799897 | 10/1997 |
| EP | 0799897 A1 | 10/1997 |
| JP | 04/262799 A2 | 9/1992 |
| JP | 04/304900 A2 | 10/1992 |
| WO | WO 89/09835 A1 | 10/1989 |
| WO | WO 89/12696 A1 | 12/1989 |
| WO | WO 90/01069 A1 | 2/1990 |
| WO | WO 93/25563 A1 | 12/1993 |
| WO | WO 95/00667 A1 | 1/1995 |
| WO | WO 95/05480 A2 | 2/1995 |
| WO | WO 95/14106 A2 | 5/1995 |
| WO | WO 96/15271 A1 | 5/1996 |
| WO | WO 96/17958 A1 | 6/1996 |
| WO | WO 97/31256 A2 | 8/1997 |
| WO | WO 98/04746 A1 | 5/1998 |
| WO | WO 00/55369 A1 | 9/2000 |
| WO | WO 00/58516 | 10/2000 |
| WO | WO 03/006677 A2 | 1/2003 |

OTHER PUBLICATIONS

Hartvig et al., Abstract 15, Localised Mutation Detection With Padlock Probes and Rolling Circle Replication, The San Diego Conference Nucleic Acid Technologies in Disease Detection, Nov. 17-19, 1999, Poster Session Abstracts, Clinical Chemistry, vol. 45, No. 11, 1999, p. 2050.

Hatch et al., Rolling Circle Amplification of DNA Immobilized on Solid Surfaces and Its Application to Multiplex Mutation Detection, Apr. 1999, Genetic Analysis: Biomolecular Engineering 15 (1999) 35-40.

Lin et al., Identification of a Region in the Integrin B3 Subunit That Confers Ligand Binding Specificity, 1997, The Journal of Biological Chemistry, vol. 272, No. 38, Issue of Sep. 19, pp. 23912-23920.

Sabanayagam et al., Molecular DNA Switches and DNA Chips, Jun. 1999, in Micro- and Nanofabricated Structures and Devices for Biomedical and Environmental Applications II, vol. 3606, Ed. Ferrari, M. (Proceedings of the International Society for Optical Engineering, Bellingham, WA), pp. 90-98.

Speel, Detection and amplification systems for sensitive,multiple-target DNA and RNA in situ hybridization: looking inside cells with a spectrum of colors, presented at the 41st Symposium of the Society for Histochemistry in Gargellen, Austria, on Sep. 25, 1999, Histochem Cell Biol (1999) 112: pp. 89-113.

Press Release: Illumina Challenges Ownership Rights for Patent Covering Parallele Technology Acquired by Affymetrix. Published online by Illumina on Oct. 24, 2005 (illumina.com).

Antson, et al, "PCR-Generated PadlockProbes Detect Single Nucleotide Variation in Genomic DNA", Nucleic Acids Research (2000) 28(12):1-6.

Baner, et al, "Signal of Padlock Probes by Rolling Circle Replication", Nucleic Acids Research, (1998) 26(22): 5073-5078.

Barany, et al, "Genetic disease detection and DNA amplification using cloned thermostable ligase", Proc. Natl. Acad. Sci., 88:189-193 (1991).

Beaucage, et al, "Deoxynucleoside phosphoramides", Tetrahedron Lett., 22: 1859-1862 (1981).

Chee, "Enzymatic multiplex DNA sequencing", Nucleic Acids Research, 19: 3301-3305 (1991).

Dolinnaya, et al, "Oligonucleotide Circularization by Template-Directed Chemical Ligation", Nucleic Acids Research (1993) 21(23):5403-5407.

Favis, et al, "Universal DNA Array Detection of Small Insertions and Deletions in BRCA1 and BRCA2", Nature Biotechnology (2000) 18:561-564.

Fire, et al, "Rolling Replication of Short DNA Circles", Proc. Natl. Acad. Sci., (1995) 92:4641-4645.

Fodor, et al, "Light-directed, spatially addressable parallel chemical synthesis", Science, 251: 767-773 (1991).

Gade, et al, "Incorporation of Nonbase Residues into Synthetic Oligonucleotides and Their Use in the PCR", GATA (1993) 10(2): 61-65.

Gerry, et al, "Universal DNA Microarray Method for Muiltiplex Detection of Low AbundancePoint Mutations", J. Mol. Biol. (1999) 292:251-262.

Gronostajski, R.M., "Site-specific DNA Binding of Nuclear Factor I: Effect of the Spacer Region", Nucleic Acids Research (1987) 15: 5545-5559.

Kozal, et al, "Extensive polymorphisms observed in HIV-1 clade B protease gene using high-density oligonucleotide arrays", Nature Medicine, 2: 753-759 (1996).

Landegren, et al, "A ligase-mediated gene detection techniques", Science, 241: 1077-1080 (1988).

Landegren, et al, "Detecting Genes with Ligases", Methods (1996); 9(1): 84-90.

Lizardi, et al, "Mutation Detection and Single-Molecule Counting Using Isothermal Rolling-Circle Amplification", Nature Genetics (1998) 19:225-232.

Longo et al., "Use of uracil DNA glycosylase to control carry-over contamination in polymerase chain reactions," Gene, 93: 125-128 (1990).

Needham-Van Devanter, et al, "Characterization of an adduct between CC-1065 and a defined oligodeoxynucleotide duplex", Nucleic Acids Research, 12:6159-6168 (1984).

Nilsson, et al, "Padlock Probes Revel Single-Nucleotide Differences, Parent of Origin and In Situ Distribution of Centromeric Sequences in Human Chromosomes 13 and 21", Nature Genetics (1997) 16(3): 252-255.

Nilsson, et al, "Padlock Probes: Circularizing Oligonucleotides for Localized DNA Detection", Science (1994) 265:2085-2088.

Sheldon, et al, "Matrix DNA hybridization", Clin. Chem., 39:718-719 (1993).
Shoemaker et al., "Quantitaive phenotypic analysis of yeast deletion mutants using a highly parallel molecular bar-coding strategy," Nature Genetics, 14:450-456 (1996).
Sooknanan et al., "Nucleic acid sequence based amplification," Molecular Methods for Virus Detection, Wiedbrauk and Farkas, eds., Chapter 12, pp. 261-285 (Academic Press, New York, 1995).
Thomas, et al, "Amplification of Padlock Probes for DNA Diagnostics by Cascade Rolling Circle Amplification or the Polymerase Chain Reaction", Arch Pathol Lab Med. (1999) 123(12): 1170-1176.
Xu et al., "High sequence fidelity in a non-enzymatic DNA autoligation reaction," Nucleic Acids Research, 27:875-881 (1999).
Zhang, et al, "Amplification of target-specific, ligation-dependent circular probe", Gene, 211:277-285 (1998).

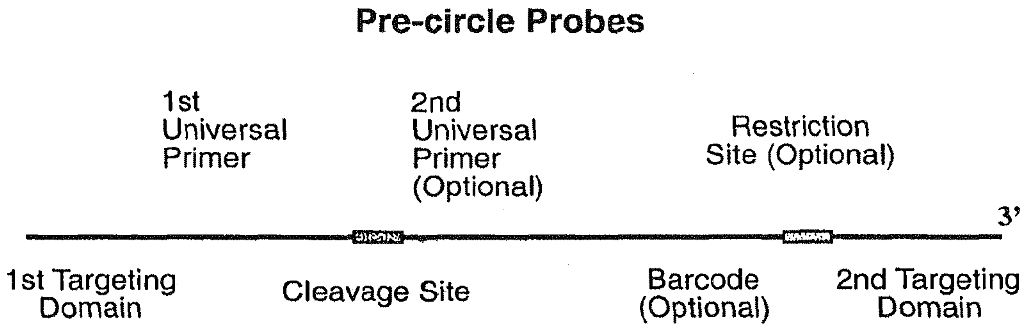
FIG._1
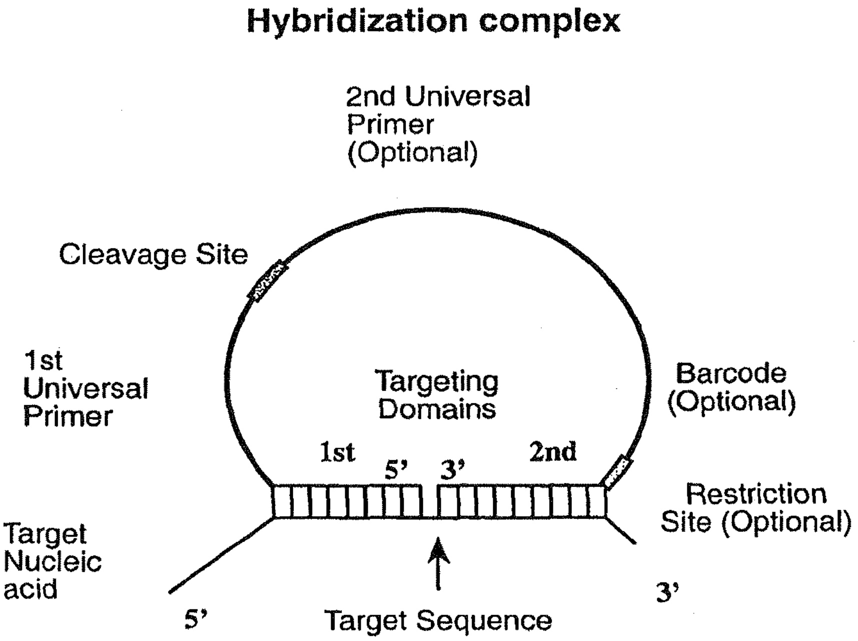
FIG._2A

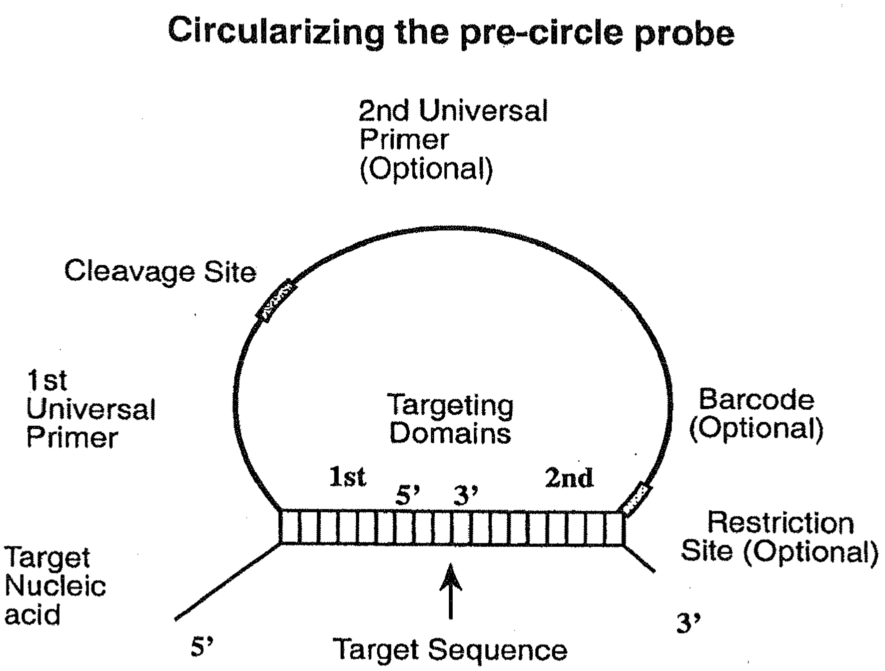
FIG._2B
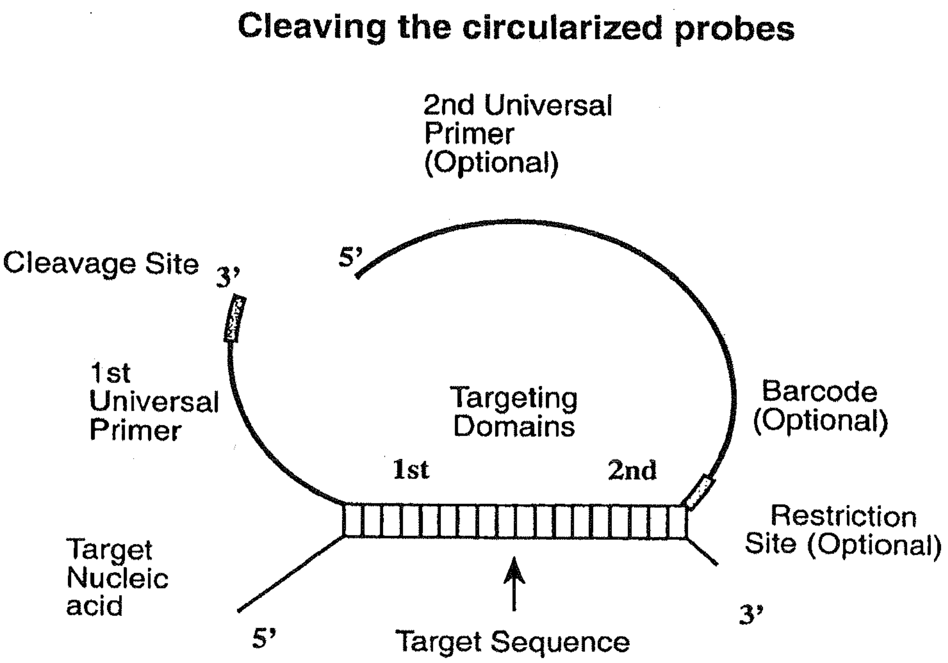
FIG._2C

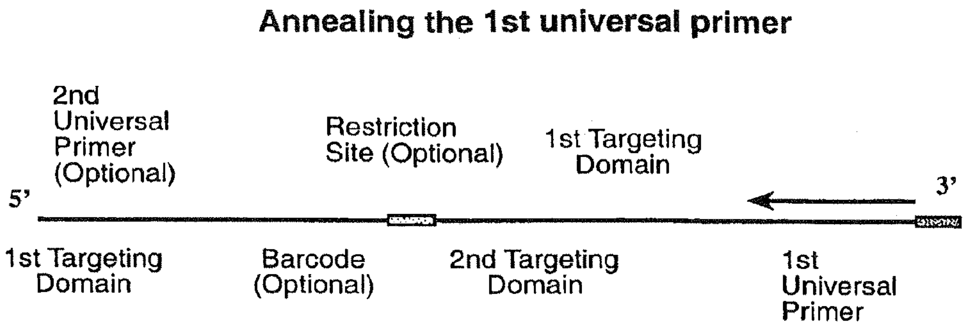
FIG._2D
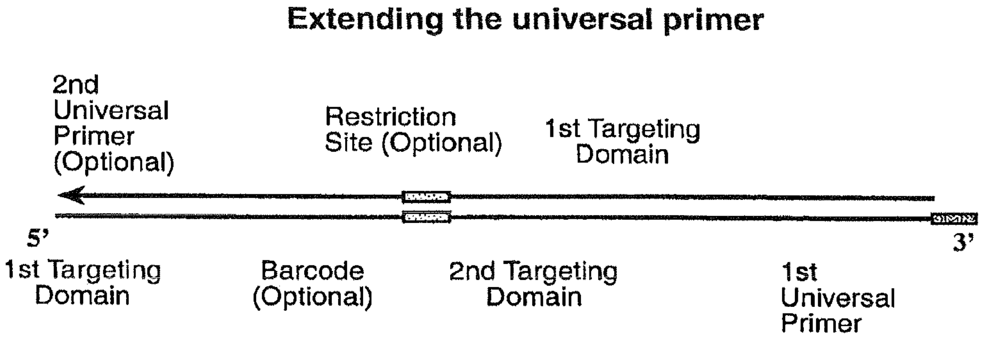
FIG._2E
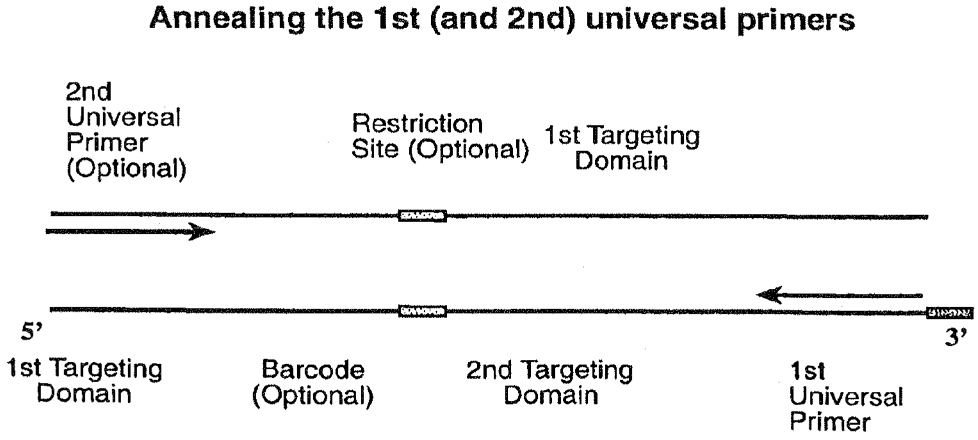
FIG._2F

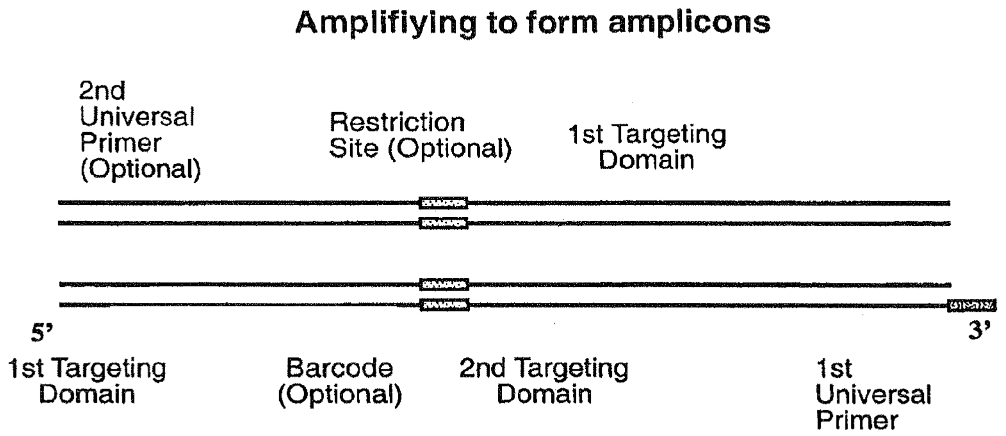
FIG._2G
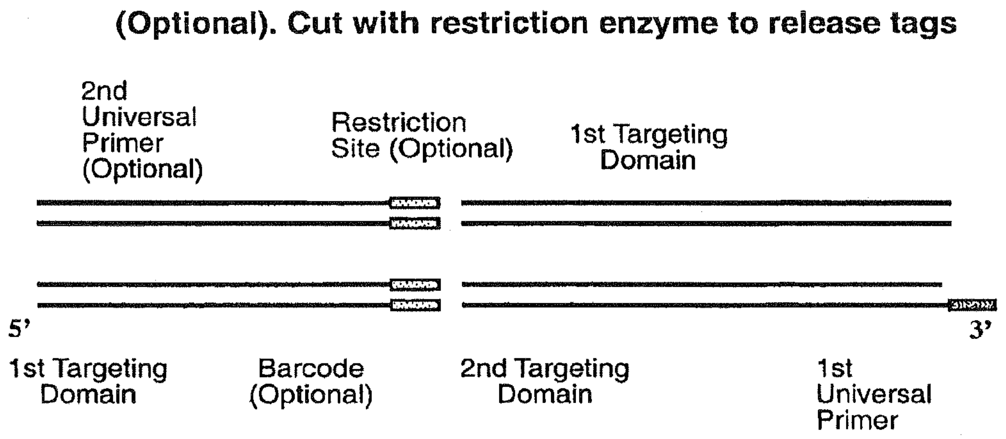
FIG._2H

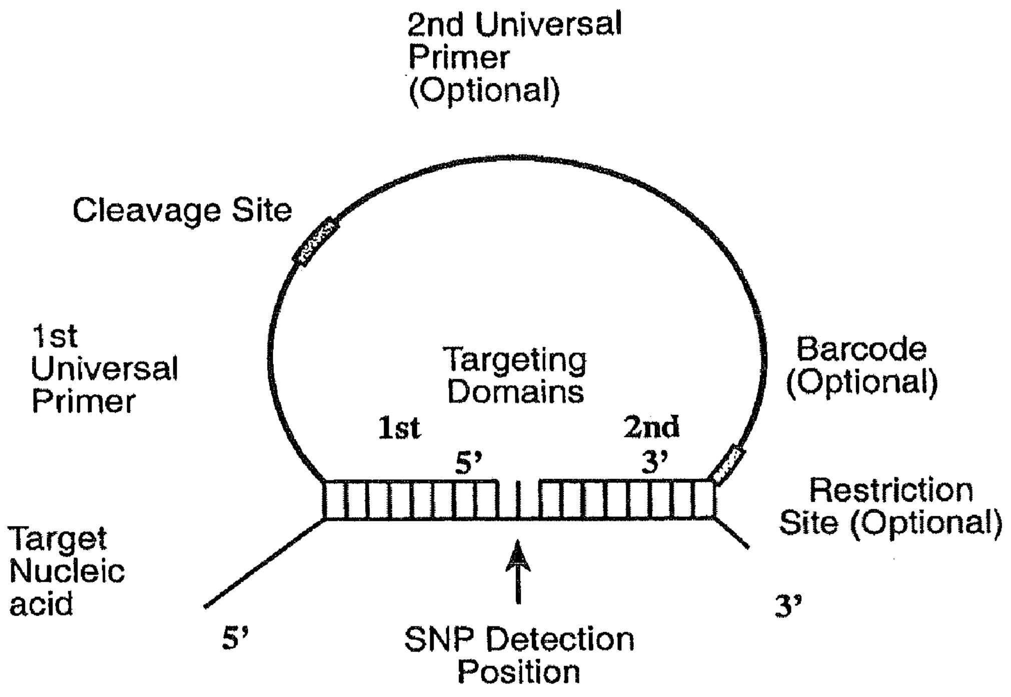
FIG._3A
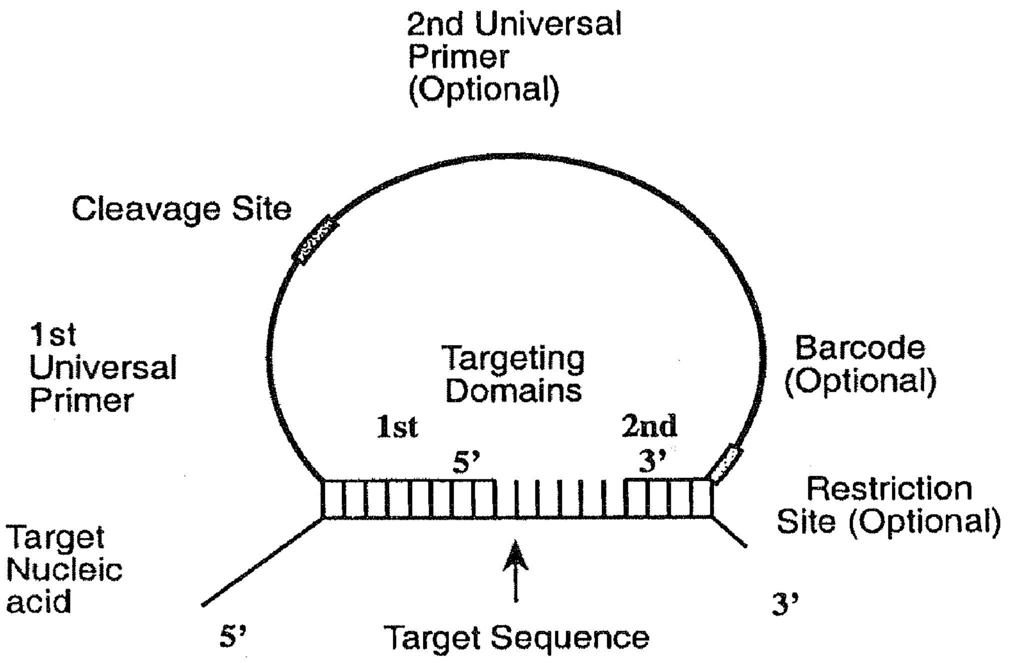
FIG._3B

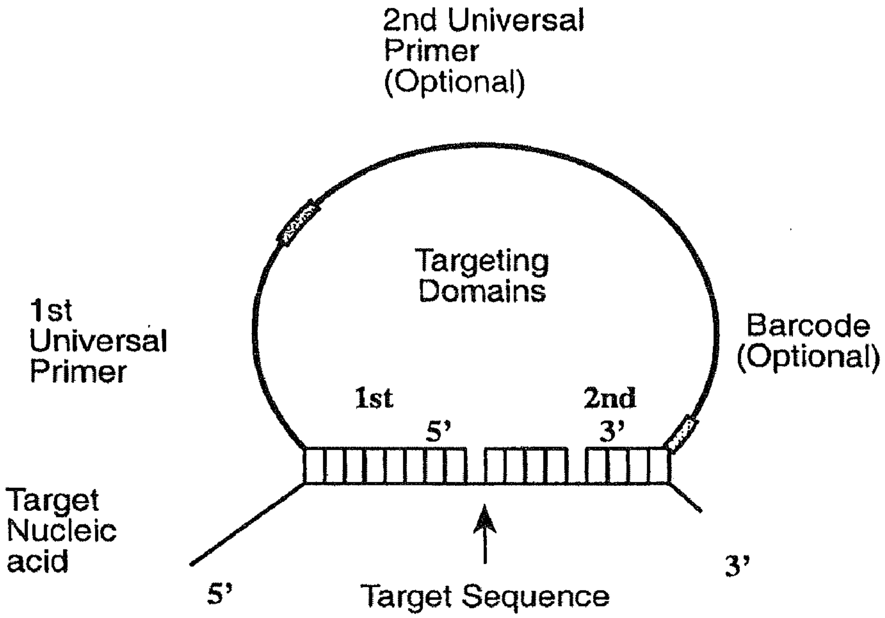
FIG._3C
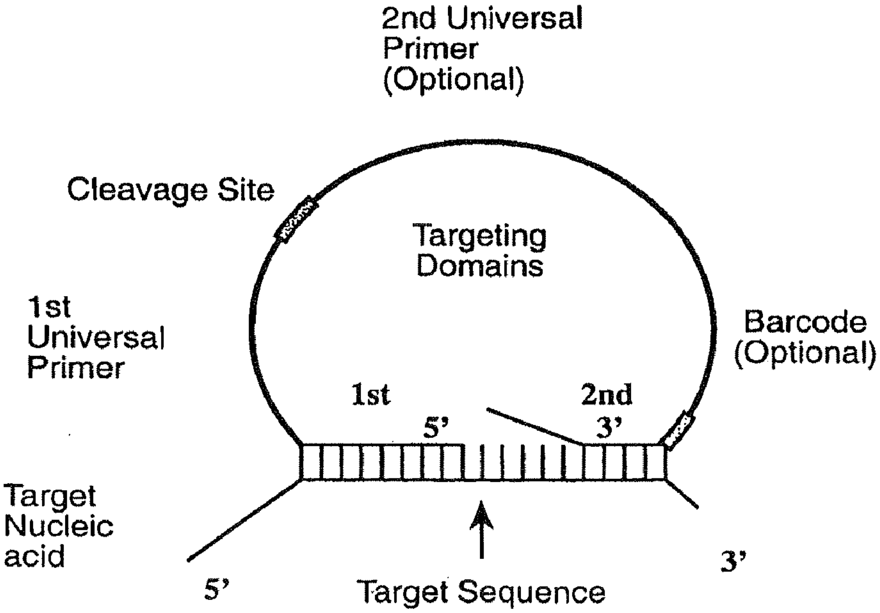
FIG._3D

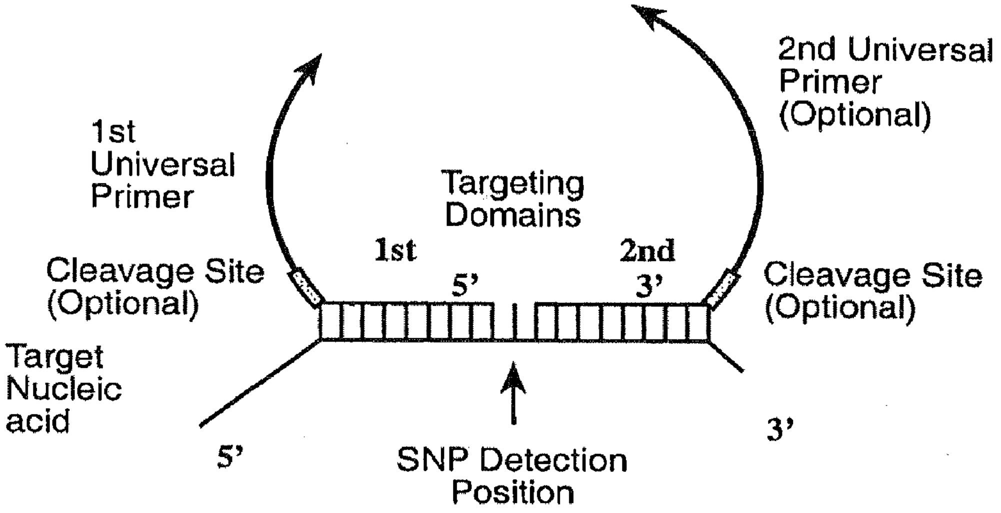
FIG._4

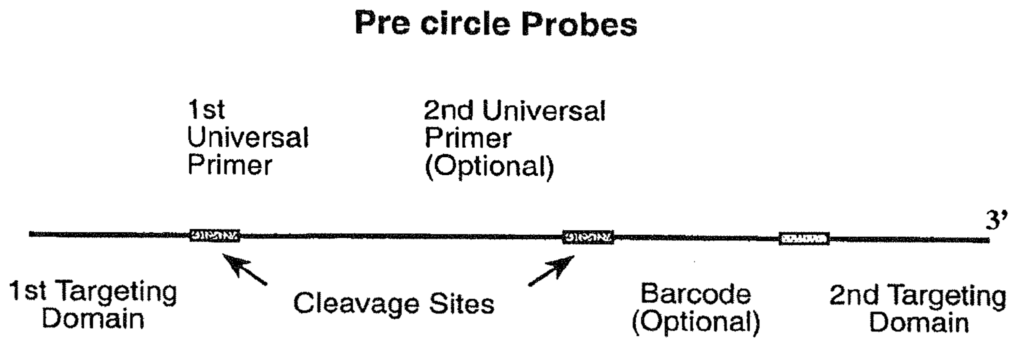
FIG._5A
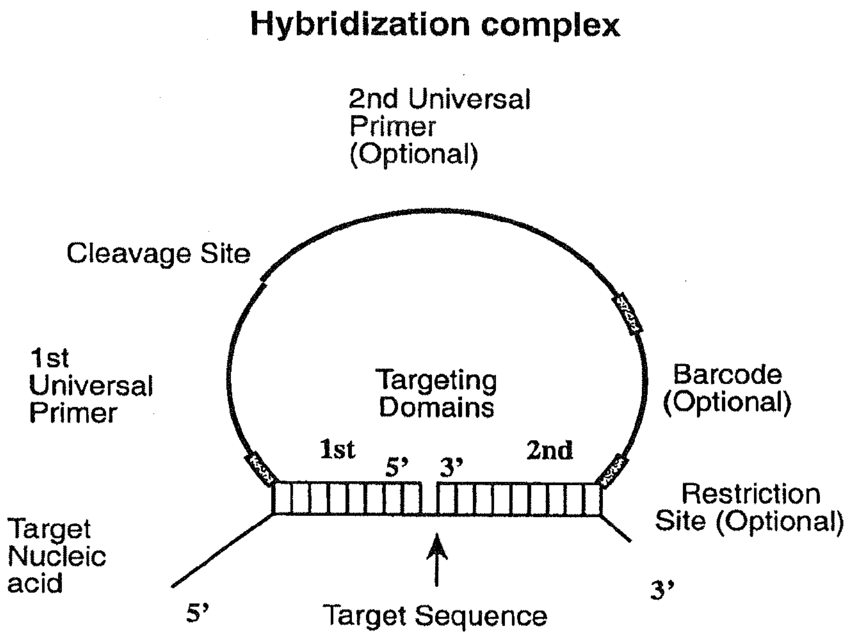
FIG._5B

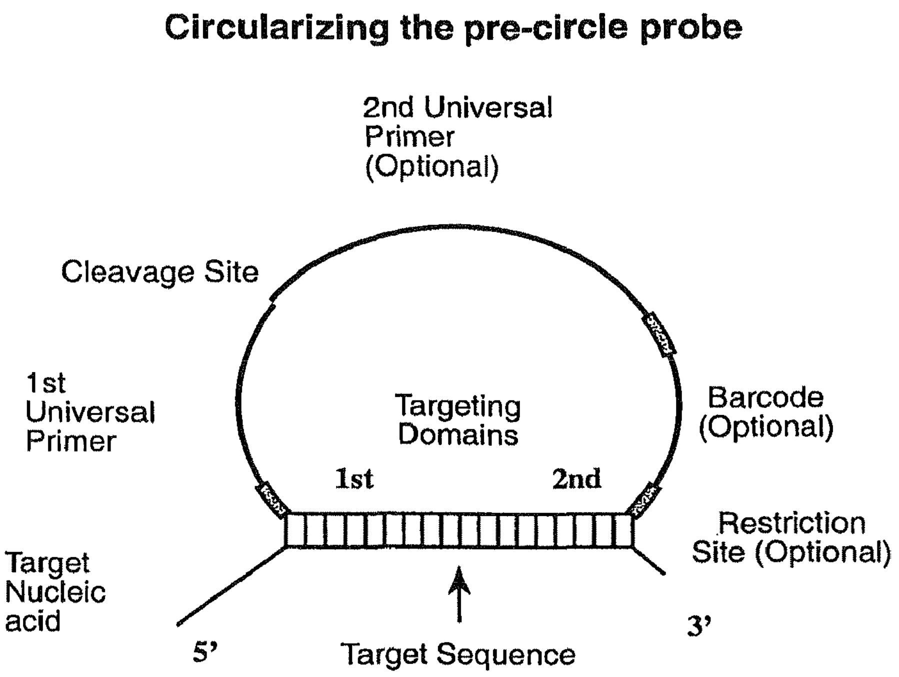
FIG._5C
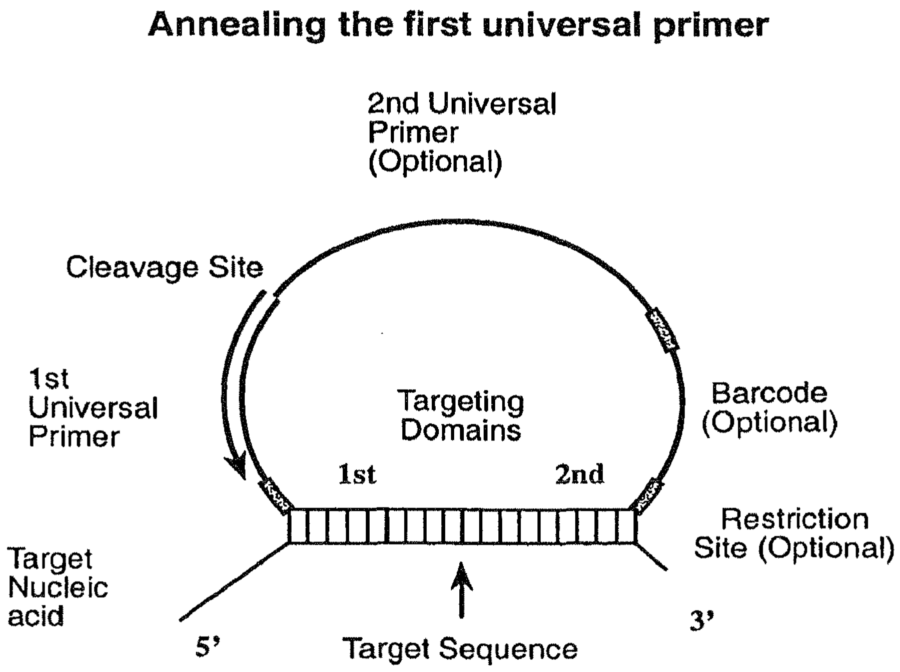
FIG._5D

Extending the first universal primer to form an extension product
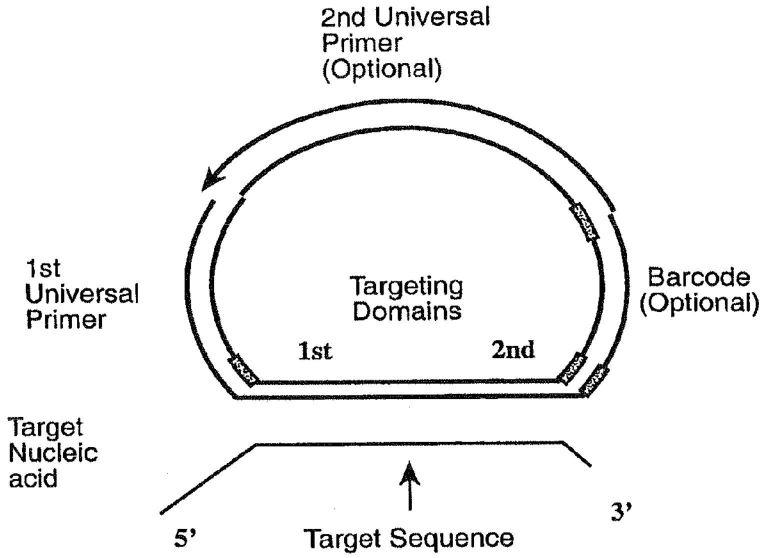
FIG._5E
Cleaving the probe at the cleavage sites
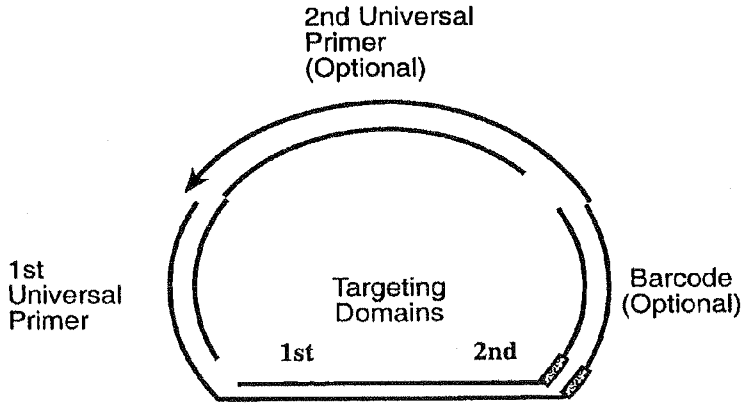
FIG._5F Annealing the 2nd universal primer to the extension product
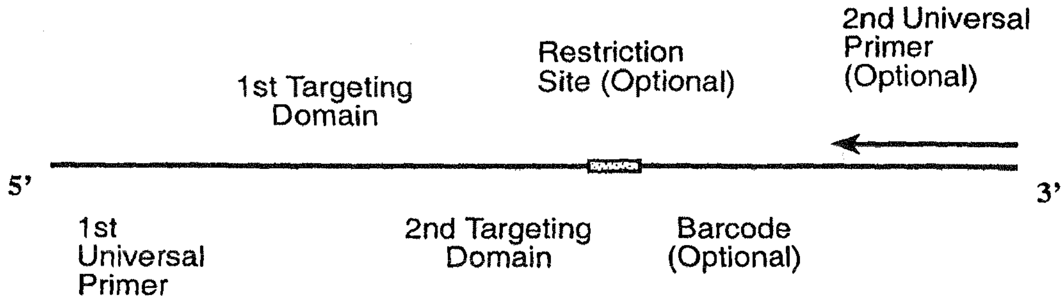
FIG._5G
Extending the universal primer
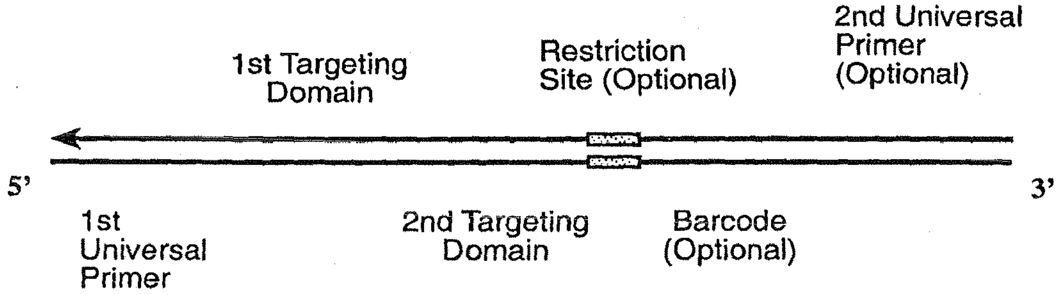
FIG._5H
Annealing the 1st (and 2nd) universal primers
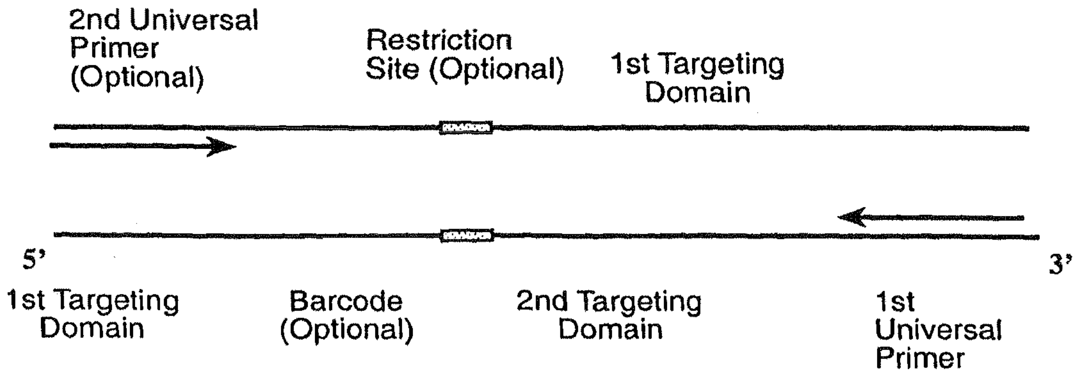
FIG._5I

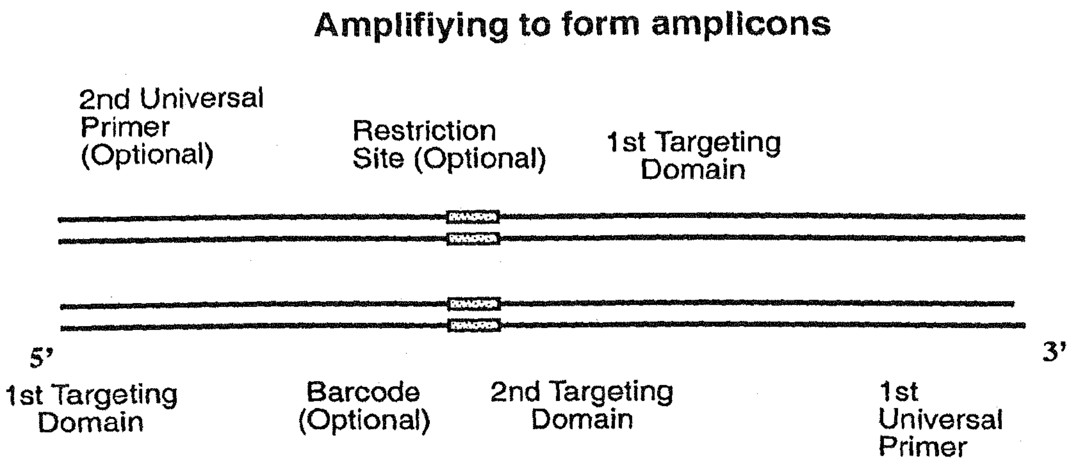
FIG._5J
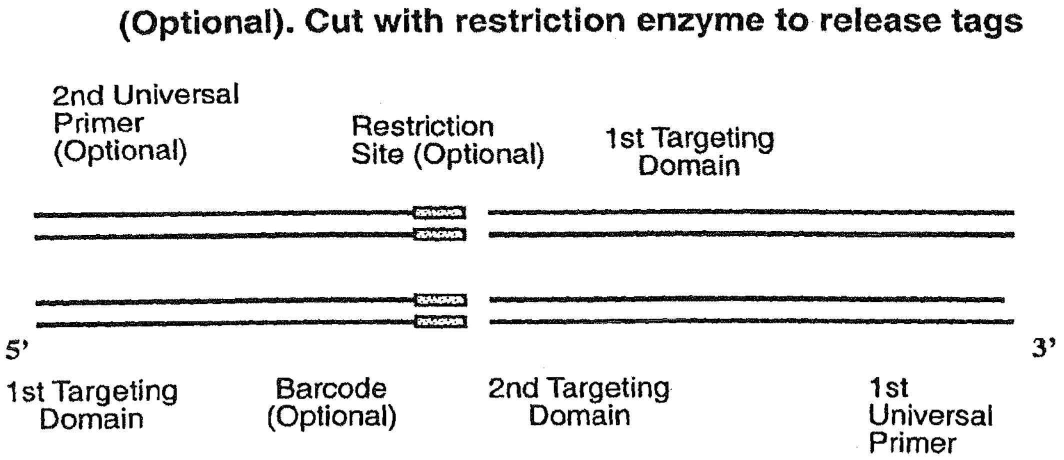
FIG._5K

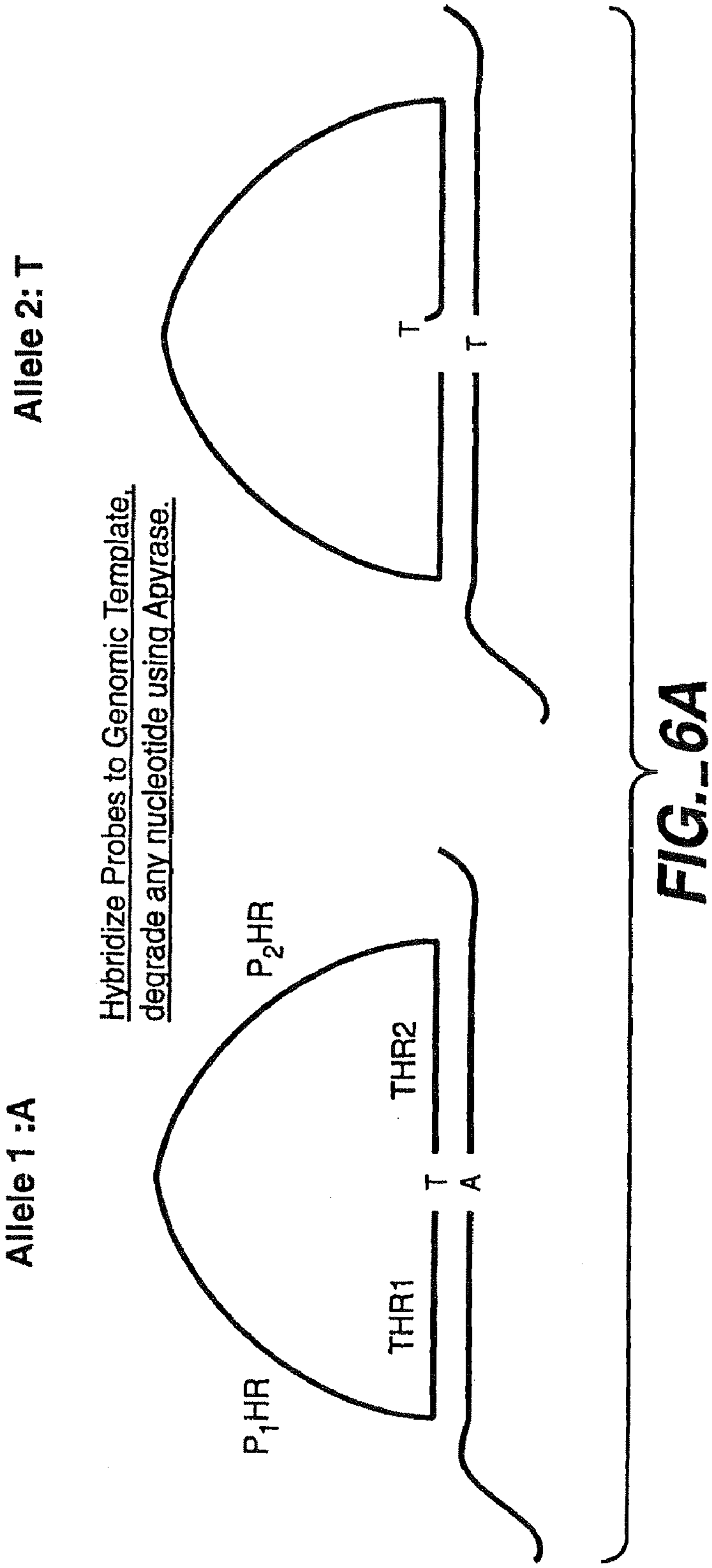
FIG._6A

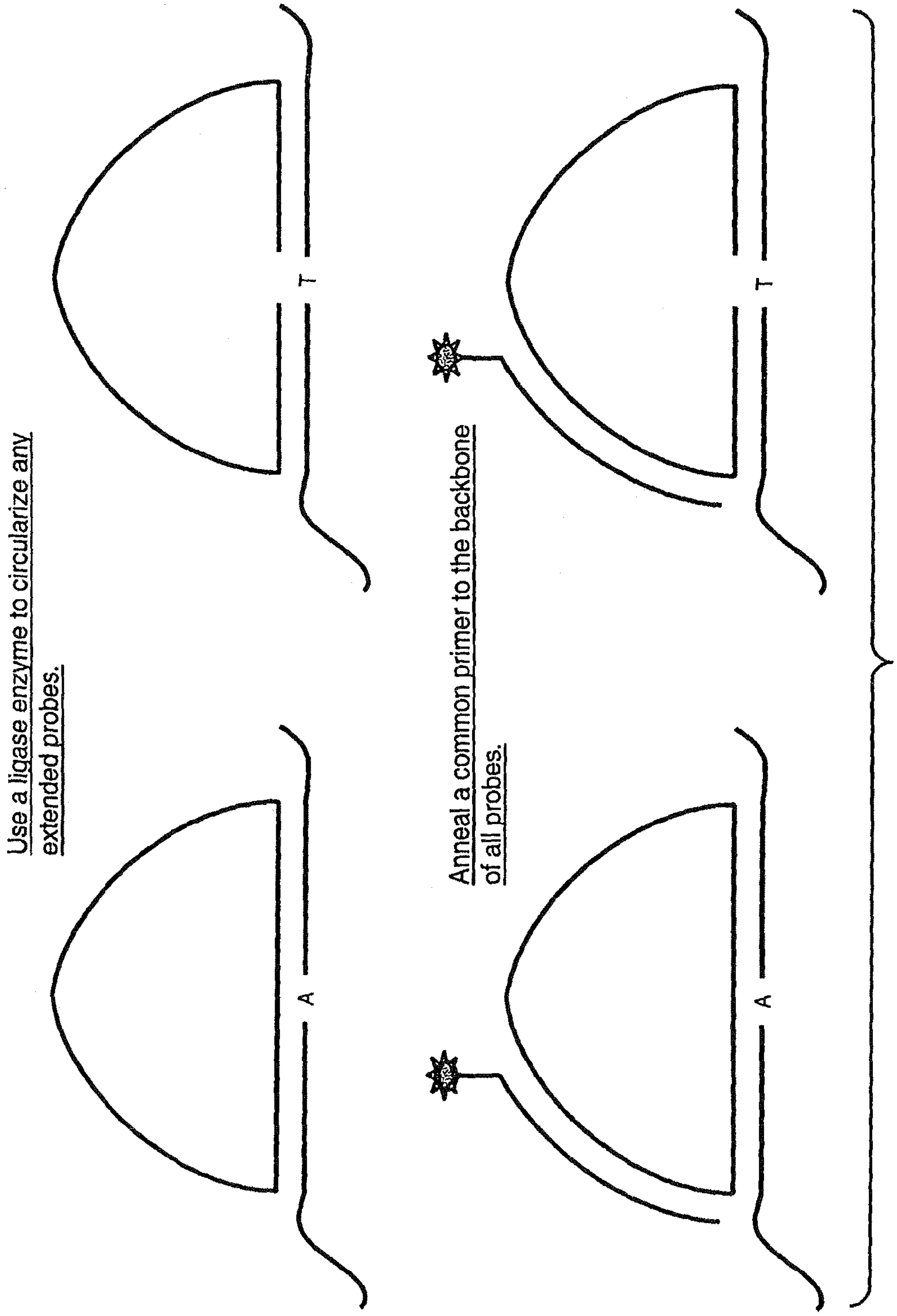
FIG._6B

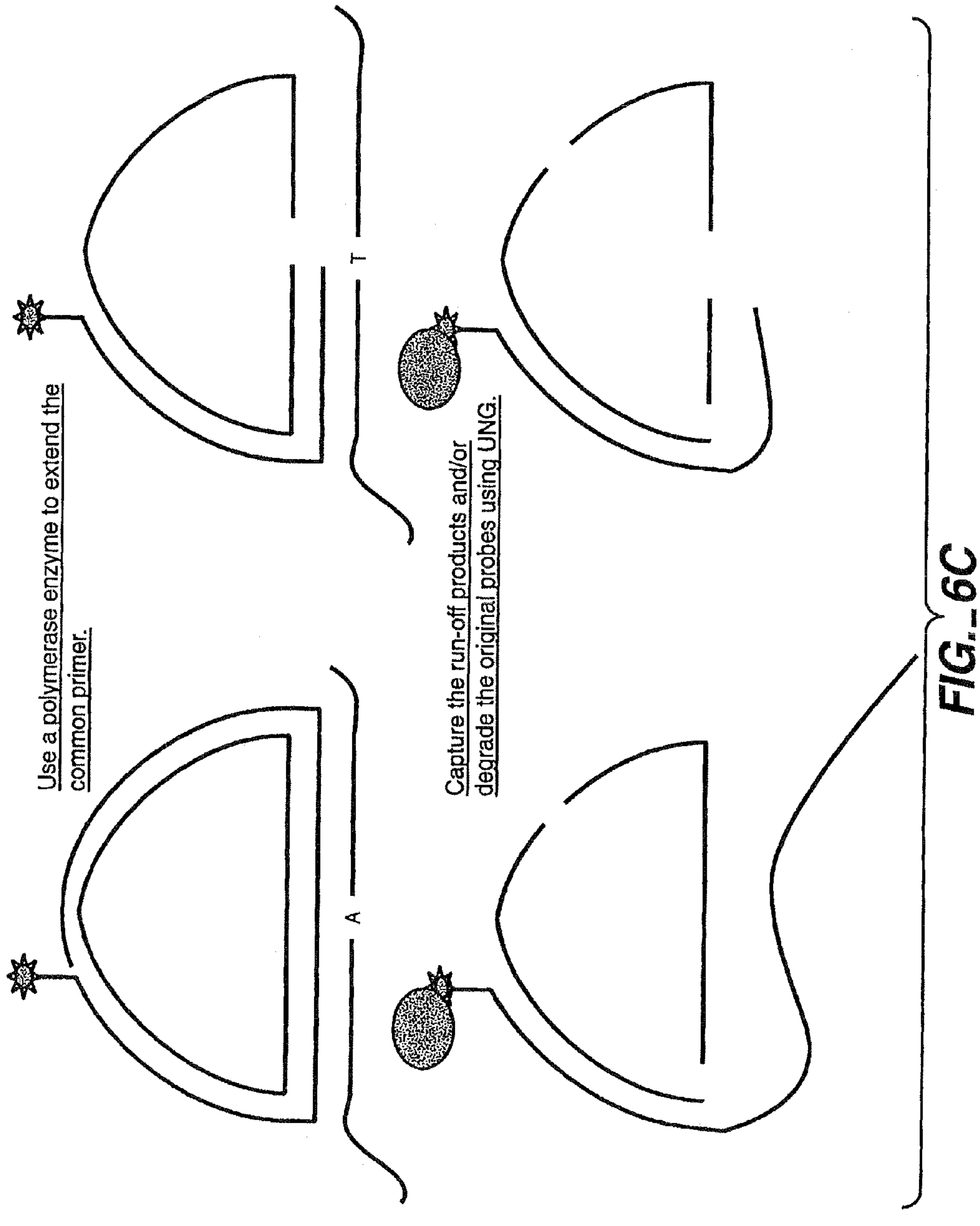
FIG._6C

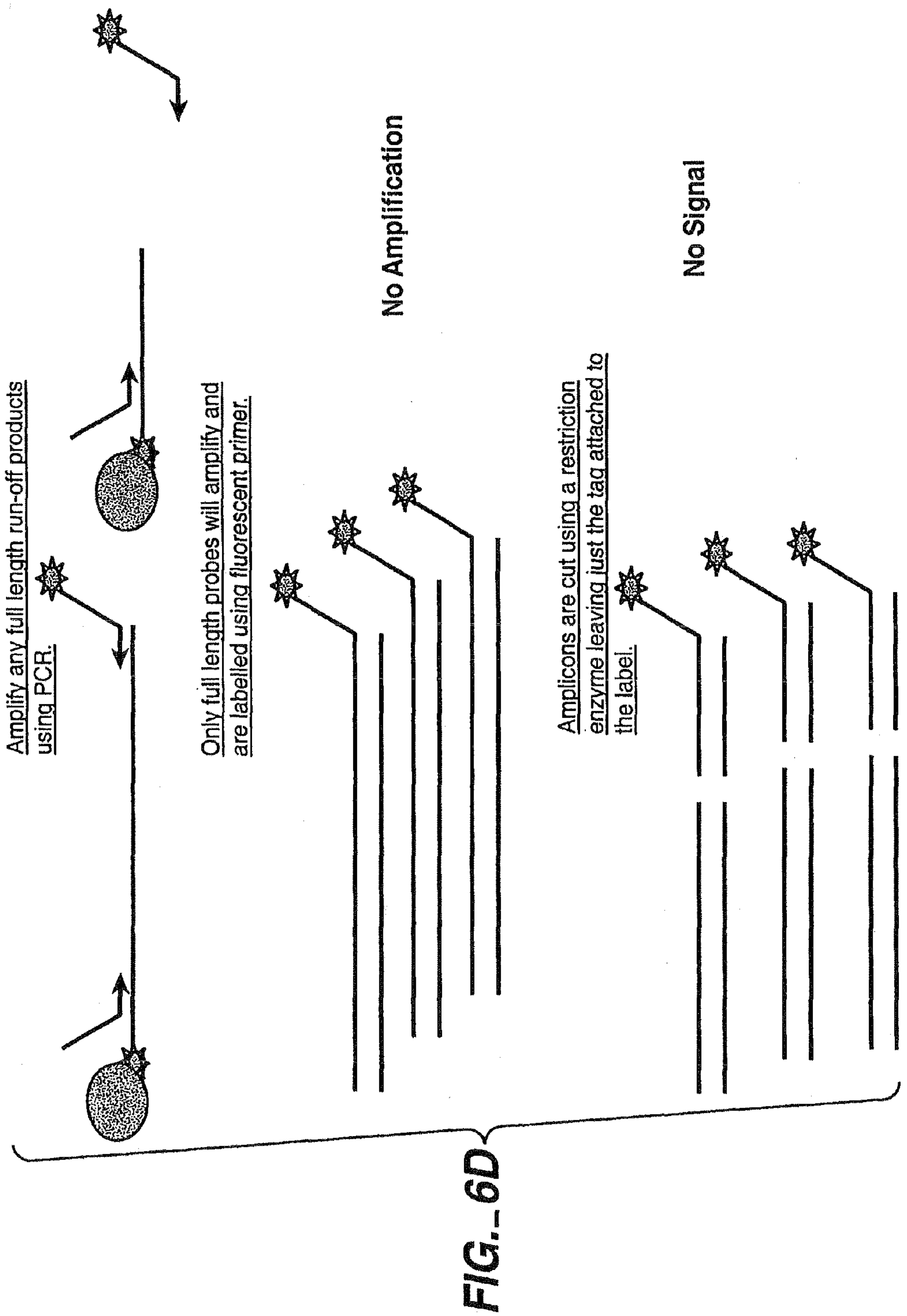
FIG._6D

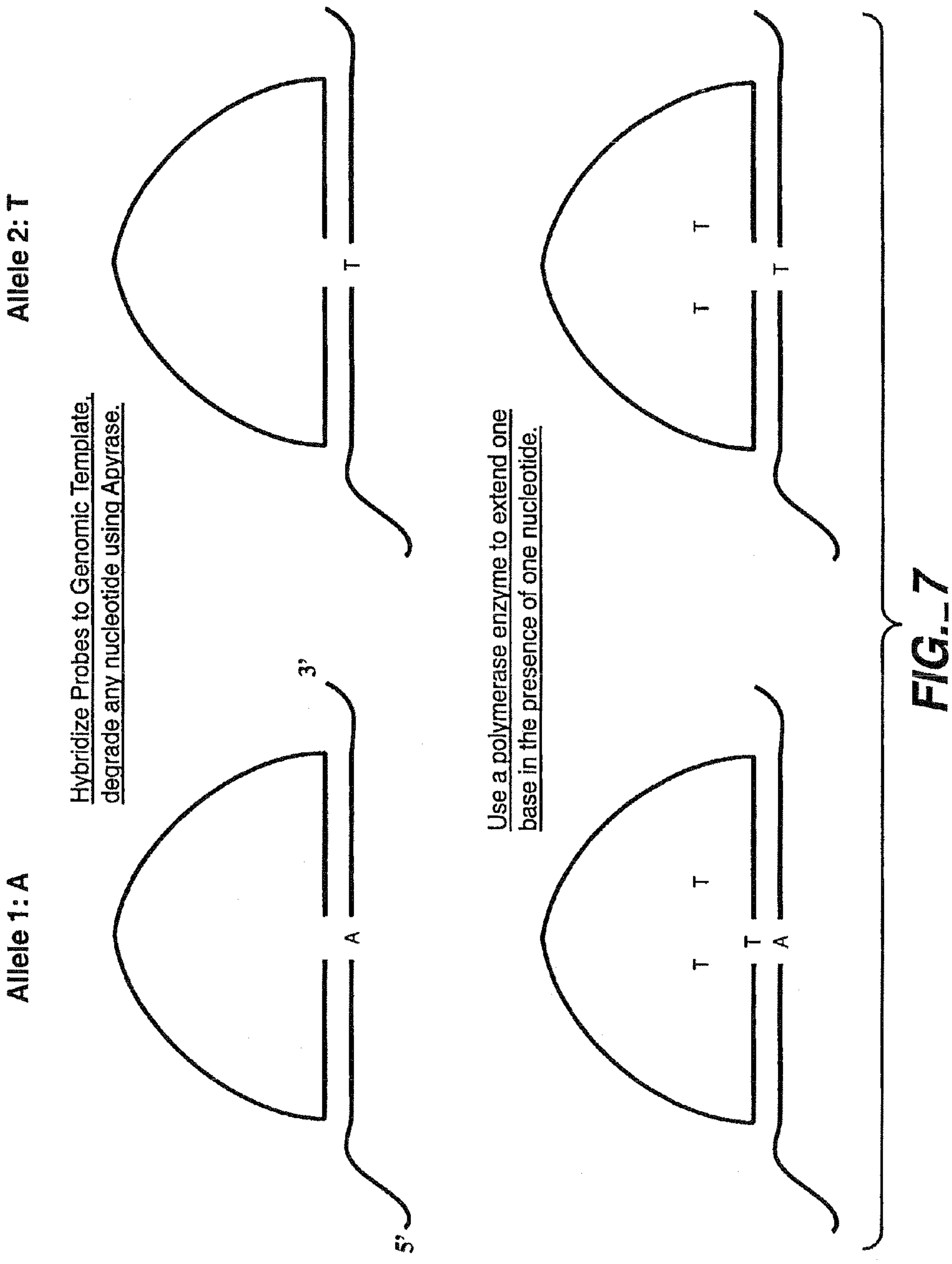
FIG._7

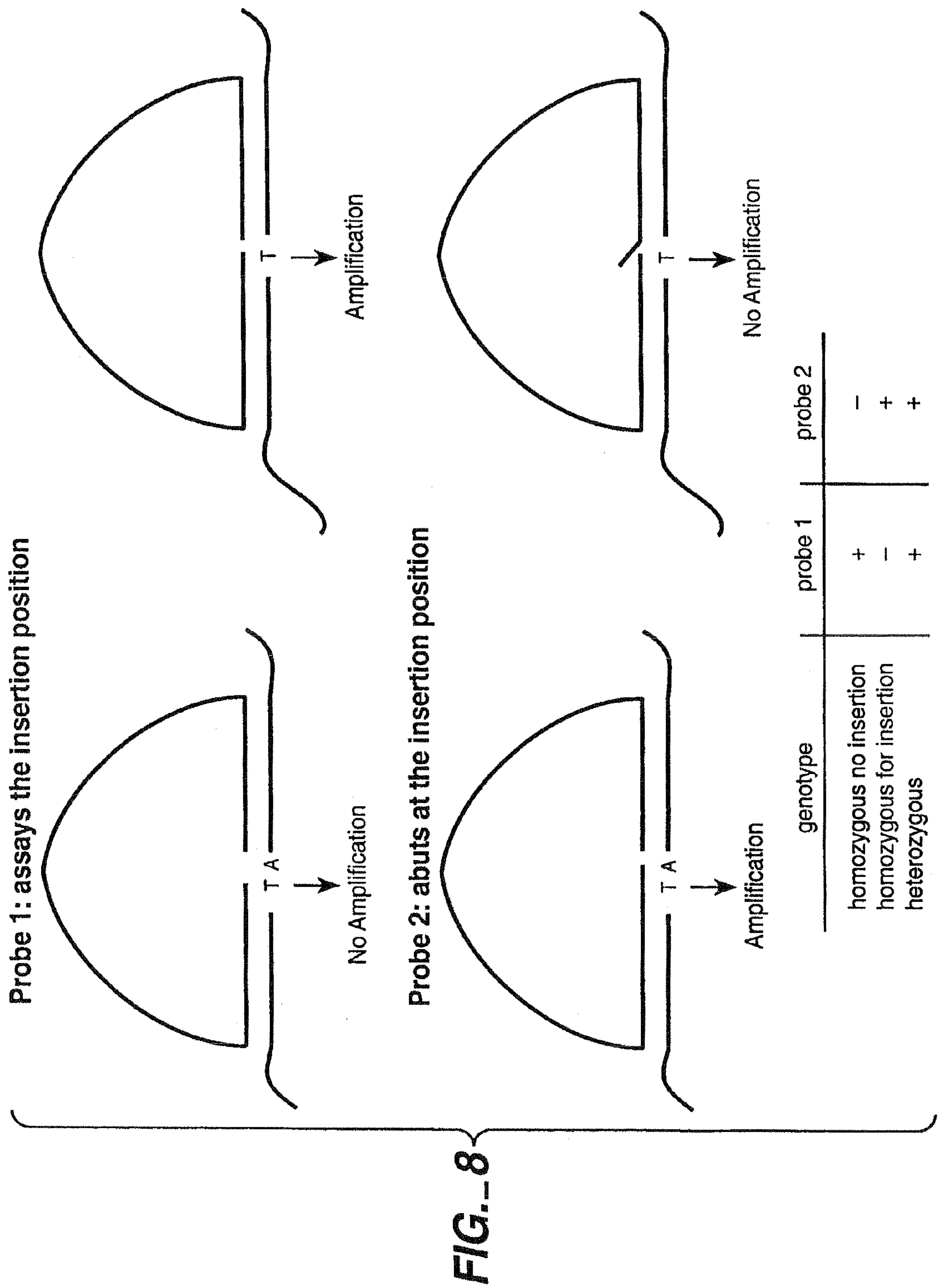
| genotype | probe 1 | probe 2 |
|---|---|---|
| homozygous no insertion | + | − |
| homozygous for insertion | − | + |
| heterozygous | + | + |
FIG._8

PRECIRCLE PROBE NUCLEIC ACID AMPLIFICATION METHODS

CROSS-REFERENCE TO RELATED APPLICATIONS

This application is a continuation of U.S. application Ser. No. 10/826,633 (U.S. Pat. No. 7,700,323) filed Apr. 15, 2004, which is a continuation of U.S. application Ser. No. 09/999, 362 (U.S. Pat. No. 6,858,412) filed Oct. 24, 2001, which claims the benefit of U.S. Provisional Application No. 60/242,901, filed Oct. 24, 2000. The disclosures of each of the foregoing applications are expressly incorporated by reference herein.

GOVERNMENT INTERESTS

This invention was made with government support under HG00205 awarded by the National Institutes of Health. The government has certain rights in the invention.

FIELD OF THE INVENTION

The invention is directed to novel methods of multiplexing nucleic acid reactions, including amplification, detection and genotyping. The invention relies on the use of precircle probes that are circularized in the presence of the corresponding target nucleic acids, cleaved, and then amplified.

BACKGROUND OF THE INVENTION

Human diseases arise from a complex interaction of DNA polymorphisms or mutations and environmental factors. Single nucleotide polymorphisms (SNPs) have recently been identified as potentially powerful means for genetic typing, and are predicted to supersede microsatellite repeat analysis as the standard for genetic association, linkage, and mapping studies.

The major goal in human genetics is to ascertain the relationship between DNA sequence variation and phenotypic variation. For these studies, molecular polymorphisms are indispensable for conventional meiotic mapping, fine-structure mapping and haplotype analysis. However, with the contemplated sequencing of a reference human genome and identification of all human genes, studies of complex genetic disorders are expected to be more efficient if one were to systematically search all, human genes for functional variants by association and linkage disequilibrium studies. This requires the development of technology and methods for the systematic discovery of genetic variation in human DNA, primarily the single nucleotide polymorphisms (SNPs) which are the most abundant.

Several different types of polymorphism have been reported. A restriction fragment length polymorphism (RFLP) means a variation in DNA sequence that alters the length of a restriction fragment as described in Botstein et al., Am. J. Hum. Genet. 32, 314-331 (1980). The restriction fragment length polymorphism may create or delete a restriction site, thus changing the length of the restriction fragment. RFLPs have been widely used in human and animal genetic analyses (see WO 90/13668; WO90/11369; Donis-Keller; Cell 51, 319-337 (1987); Lander et al., Genetics 121, 85-99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., FEBS Lett. 307, 113-115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs and VNTRs. Some single nucleotide polymorphisms occur in protein-coding sequences, in which case, one of the polymorphic forms may give rise to the expression of a defective or other variant protein. Other single nucleotide polymorphisms occur in noncoding regions. Some of these polymorphisms may also result in defective or variant protein expression (e.g., as a result of defective splicing). Other single nucleotide polymorphisms have no phenotypic effects. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The presence of SNPs may be linked to, for example, a certain population, a disease state, or a propensity for a disease state.

Generally, polymorphisms can be associated with the susceptibility to develop a certain disease or condition. The presence of polymorphisms that cause a change in protein structure are more likely to correlate with the likelihood to develop a certain type or "trait." Thus, it is highly desirable to dispose of methods that allow quick and cheap genotyping of subjects. Early identification of alleles that are linked to an increased likelihood of developing a condition would allow early intervention and prevention of the development of the disease.

Pharmacogenomics is the study of the relationship between an individual's genotype and that individual's response to a foreign compound or drug. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining the type of drug and dosage and/or therapeutic regimen of treatment.

Pharmacogenomics deals with clinically significant hereditary variations in the response to drugs due to altered drug disposition and abnormal action in affected persons. See, for example, Eichelbaum, M. et al. (1996) Clin. Exp. Pharmacol, Physiol, 23(10-11):983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofarans) and consumption of fava beans. Thus, it would be highly desirable to dispose of fast and cheap methods for determining a subject's genotype so as to predict the best treatment.

Thus, there is a considerable demand for high throughput, very low cost nucleotide sequence (e.g., SNPs) identification in regions of known sequence in order to identify alleles of polymorphic genes, e.g., SNPs. There are currently many methods available to screen polymorphisms, e.g., SNPs. A typical genotyping strategy involves three basic steps. The first step consists of amplifying the target DNA, which is necessary since a human genome contains $3\times10^9$ base pairs of DNA and most assays lack both the sensitivity and the selectivity to accurately detect a small number of bases, in particular a single base, from a mixture this complex. As a result, most strategies currently used rely on first amplifying a region of several hundred bases including the polymorphic region to be screened using PCR. This reaction requires 2 unique primers for each amplified region ("amplicon"). Once the complexity has been reduced, the second step in the currently used methods consists of differentially labeling the alleles so as to be able to identify the genotype. This step involves attaching some identifiable marker (e.g. fluorescent label, mass tag, etc.) in a manner which is specific to the base being assayed. The third step in currently used methods consists of detecting the allele to determine the individuals genotypes. Detection mechanisms include fluorescent signals, the polarization of a fluorescent signal, mass spectrometry to identify mass tags, etc.

Sensitivity, i.e. detection limits, remain a significant obstacle in nucleic acid detection systems, and a variety of techniques have been developed to address this issue. Briefly, these techniques can be classified as either target amplification or signal amplification. Target amplification involves the amplification (i.e. replication) of the target sequence to be detected, resulting in a significant increase in the number of target molecules. Target amplification strategies include the polymerase chain reaction (PCR), strand displacement amplification (SDA), and nucleic acid sequence based amplification (NASBA).

Alternatively, rather than amplify the target, alternate techniques use the target as a template to replicate a signaling probe, allowing a small number of target molecules to result in a large number of signaling probes, that then can be detected. Signal amplification strategies include the ligase chain reaction (LCR), cycling probe technology (CPT), invasive cleavage techniques such as Invader™ technology, Q-Beta replicase (QβR) technology, and the use of "amplification probes" such as "branched DNA" that result in multiple label probes binding to a single target sequence.

The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", allelic PCR (see Newton et al. Nucl. Acid Res. 17:2503 91989); "reverse transcriptase PCR" or "RT-PCR", "biotin capture PCR", "vectorette PCR", "panhandle PCR", and "PCR select cDNA subtraction", among others.

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Nucleic acid sequence based amplification (NASBA) is generally described in U.S. Pat. No. 5,409,818 and "Profiting from Gene-based Diagnostics", CTB International Publishing Inc., N.J., 1996, both of which are incorporated by reference.

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667; all of which are specifically incorporated herein by reference.

The oligonucleotide ligation assay (OLA; sometimes referred to as the ligation chain reaction (LCR)) involves the ligation of at least two smaller probes into a single long probe, using the target sequence as the template for the ligase. See generally U.S. Pat. Nos. 5,185,243, 5,679,524 and 5,573,907; EP 0 320 308 81; EP 0 336 731 81; EP 0 439 182 81; WO 90/01069; WO 89/12696; and WO 89/09835, all of which are incorporated by reference.

Invader™ technology is based on structure-specific polymerases that cleave nucleic acids in a site-specific manner. Two probes are used: an "invader" probe and a "signaling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

None of the methods currently used are particularly well suited to very high throughput at low cost. One of the principal shortcomings of the available methods are their reliance on the Polymerase Chain Reaction (PCR) in order to generate relatively simple DNA template for polymorphism analysis (i.e., genotyping). This reaction is not easily multiplexed which implies that each assay for identifying a particular polymorphism requires a separate reaction. This makes any high throughput assay cumbersome and expensive as millions of reactions will have to be performed in order to screen the requisite number of polymorphism. Thus, there is a need for a method that allows thousands of polymorphic regions, e.g., SNPs to be analyzed and quantified in a single reaction vessel, greatly increasing the throughput and decreasing the cost of analysis.

SUMMARY OF THE INVENTION

In accordance with the objects outlined above, the present invention provides methods for detecting a target sequence comprising a first and second target domain in a sample. The method comprises hybridizing the target sequence to a precircle probe to form a first hybridization complex. The precircle probe comprises: a first targeting domain, a second targeting domain, at least a first universal priming site and a cleavage site. The first and second targeting domains hybridize to the first and second target domains. The first hybridization complex is contacted with a ligase to form a closed circular probe, and cleaving the closed circular probe at the cleavage site to form a cleaved probe. The cleaved probed is amplified to form a plurality of amplicons and the amplicons are detected to detect the presence of said target sequence in said sample. The precircle probe can optionally comprise a second universal priming site, and the second contacting step further comprises contacting the cleaved probe with a second universal primer. The cleavage site is optionally situated between the first and second universal priming sites.

In addition the target sequence may further comprise a gap domain between the first and second target domains. The method further comprises the additional step of contacting the first hybridization complex with an extension enzyme and at least one interrogation NTP prior to forming the closed circular probe. Alternatively, the method further comprises the additional step of contacting said first hybridization complex with at least one gap oligonucleotide prior to forming said closed circular probe, said gap oligonucleotide having a nucleic acid sequence perfectly complementary to said gap domain, wherein detecting said amplicons identifies said gap domain.

In an additional aspect, the method further comprises the additional step of digesting any linear precircle probes prior to cleaving said closed circular probe.

In an additional aspect, the method further comprises the additional step of degrading any dNTPs prior to the addition of said interrogation dNTPs.

In a further aspect, the invention provides methods for detecting a target sequence in a sample, said target sequence comprising a first and second target domain and a gap domain between said first and second target domains, said method comprising:

a) hybridizing at least one of a plurality of precircle probes to said target sequence to form a plurality of first hybridization complexes, said precircle probes each comprising:
  i) a first targeting domain;
  ii) a second targeting domain;
  iii) a detection domain;
  iv) at least a first universal priming site;
  v) a cleavage site; and
  vi) a barcode sequence;
  wherein said plurality of first and second targeting domains are complementary to said plurality of first and second target domains and said gap domain will hybridize to at least one of said plurality of detection domains;
b) contacting said plurality of first hybridization complexes with a ligase to form a plurality of closed circular probes;
c) cleaving said plurality of closed circular probes at said cleavage sites to form a plurality of cleaved probes;
d) amplifying said cleaved probes to form amplicons; and
e) detecting the presence of said amplicons to detect the presence of said plurality of target sequences in said sample.

In an additional aspect, the invention provides methods for detecting in a sample a plurality of target sequences, wherein each of said plurality of target sequences comprises first and second target domains, said method comprising:

a) hybridizing said plurality of target sequences to a plurality of precircle probes to form a plurality of first hybridization complexes, each of said precircle probes comprising:
  i) a first targeting domain;
  ii) a second targeting domain;

iii) at least a first universal priming site;
  iv) a cleavage site; and
  v) a barcode;
  wherein said plurality of first and second targeting domains hybridize to said plurality of first and second target domains;
b) contacting said plurality of first hybridization complexes with a ligase to form a plurality of closed circular probes;
c) cleaving said plurality of closed circular probes at said cleavage sites to form a plurality of cleaved probes;
d) amplifying said cleaved probes to form amplicons; and
e) detecting the presence of said amplicons to detect the presence of said plurality of target sequences in said sample.

In a further aspect, the invention provides methods for identifying the base at a detection position in a target sequence comprising a first and second target domain separated by a gap domain, said gap domain comprising said detection position, said method comprising:

a) hybridizing said target sequence to a precircle probe to form a first hybridization complex, said precircle probe comprising:
  i) a 5' first targeting domain;
  ii) a 3' second targeting domain;
  iii) at least a first universal priming site; and
  iv) a cleavage site;
  wherein said first and second targeting domains hybridize to said first and second target domains;
b) contacting said first hybridization complex with a polymerase and at least one interrogation dNTP to form an extended precircle probe;
c) contacting said first hybridization complex comprising said extended precircle probe and said target sequence with a ligase to form a closed circular probe;
d) cleaving said closed circular probe at said cleavage site to form a cleaved probe;
e) amplifying said cleaved probe to form a plurality of amplicons;
f) detecting the presence of said amplicons to detect the presence of said target sequence in said sample.

In an additional aspect, the invention provides methods for amplifying a target sequence comprising a first and second target domain in a sample, said method comprising:

a) hybridizing said target sequence to a precircle probe to form a first hybridization complex, said precircle probe comprising:
  i) a first targeting domain;
  ii) a second targeting domain;
  iii) at least a first universal priming site; and
  iv) a cleavage site;
  wherein said first and second targeting domains hybridize to said first and second target domains;
b) contacting said first hybridization complex with a ligase to form a closed circular probe;
c) cleaving said closed circular probe at said cleavage site to form a cleaved probe; and
d) amplifying said cleaved probe.

In an additional aspect, the invention provides methods for detecting a target sequence comprising a first and second target domain in a sample, said method comprising:

a) hybridizing said target sequence to a precircle probe to form a first hybridization complex, said precircle probe comprising:
  i) a first targeting domain;
  ii) a second targeting domain; and
  iii) at least a first universal priming site;

wherein said first and second targeting domains hybridize to said first and second target domains;

b) contacting said first hybridization complex with a ligase to form a closed circular probe;

c) contacting said closed circular probe at least a first universal primer, an extension enzyme and NTPs to form an extension product;

d) amplifying said extension product to form amplicons; and e) detecting said amplicons to detect the presence of said target sequence in said sample.

BRIEF DESCRIPTION OF THE DRAWINGS

FIG. 1 is a diagram of a preferred embodiment of a precircle probe according to the present invention, comprising first and second targeting domains, a first universal primer, a cleavage site, a second optional primer, an optional barcode, and an optional restriction site.

FIGS. 2A-2H depicts a preferred assay of the invention using an abutting ("gap-less") precircle probe. FIG. 2A depicts the formation of a hybridization complex, wherein the targeting domains of the precircle probe hybridize to the target domains of the target sequence, leaving the 5' and 3' termini of the bound probe adjacent. In the case of genotyping reactions, either the 5' or 3' end of the precircle probe can comprise an interrogation position, and a plurality of precircle probes, each comprising a different base at the interrogation position and a different barcode sequence may be used. FIG. 2B depicts the use of a ligase to circularize the precircle probe to form a closed circle. Optionally (not shown), the remaining linear precircle probes, and/or the target sequence, may be removed, degraded or otherwise rendered incapable of being amplified. FIG. 2C depicts the cleavage at the cleavage site, with the target sequence still present. FIGS. 2D-2G depict the preferred PCR amplification reaction, comprising the annealing of the first universal primer (2D), the extension of the first primer (2E), the annealing of the second and first primers (2F) and the extension of the primers (2G). Optionally, the use of a restriction enzyme can release the barcode and second universal priming sequences, which can be labeled as outlined herein.

FIGS. 3A-3D depict a various embodiments of the gap precircle probes of the present invention. FIG. 3A depicts a single nucleotide gap precircle probe, wherein the gap position corresponds to the SNP detection position in the target sequence. Upon addition of the correct NTP and an extension enzyme, followed by ligation with a ligase, the method proceeds as in FIG. 2. FIG. 3B depicts a multi nucleotide gap precircle probe that can be filled in with NTPs using an extension enzyme. FIG. 3C depicts the use of a gap oligonucleotide to fill the gap of the precircle probe, with ligation occurring at both ends of the gap oligo. FIG. 3D depicts a "flap-gap" precircle probe. All of these can be used in the general method shown in FIG. 2.

FIG. 4 depicts a variation on the compositions and methods of the invention. In this embodiment, which can be used with any of the abutting or gap precircle probes, the universal primers flank the barcode sequence. This embodiment can take on a variety of forms; in one embodiment, the precircle probe is hybridized to the target sequence, gaps are filled as required, and the precircle probes are ligated to form closed circular probes. In this embodiment, it is important that any non-circularized probes are removed. The universal primers are added and the barcode sequence is amplified. This can be done either with a closed circular probe, or the probes may be optionally cleaved at one or more positions.

FIGS. 5A-5K depict the "two step" embodiment of the invention, starting with an abutting precircle probe, although as will be appreciated by those in the art, any of the gap probes may be used as well. FIG. 5A depicts the precircle probe. FIG. 5B depicts the formation of a hybridization complex, wherein the targeting domains of the precircle probe hybridize to the target domains of the target sequence, leaving the 5' and 3' termini adjacent. In the case of genotyping reactions, either the 5' or 3' end of the precircle probe can comprise an interrogation position, and a plurality of precircle probes, each comprising a different base at the interrogation position and a different barcode sequence may be used. FIG. 5C depicts the use of a ligase to circularize the precircle probe to form a closed circle. Optionally (not shown), the remaining linear precircle probes, and/or the target sequence, may be removed, degraded or otherwise rendered incapable of being amplified. FIG. 5D depicts the annealing of the first primer, followed by extension using NTPs and an extension enzyme (FIG. 5E). FIG. 5F depicts the cleavage at the cleavage sites which renders all probes incapable of amplification. FIGS. 5G-5J depict the preferred PCR amplification reaction of the extension product generated in 5E, comprising the annealing of the second universal primer (5G), the extension of the primer (5H), the annealing of the second and first primers (5I) and the extension of the primers (5J). Optionally, the use of a restriction enzyme can release the barcode and second universal priming sequences, which can be labeled as outlined herein (FIG. 5K).

FIGS. 6A-6D depict a diagram of a "ligase" type method of the invention on two alleles of a gene, one allele having an A at the SNP detection position, while the other allele has a T at that position.

FIG. 7 is a diagram of a "ligase/polymerase" type method of the invention on alleles of a gene, one allele having an A at the SNP position, while the other allele has a T at that position.

FIG. 8 is a diagram representing a method for determining whether a subject is homozygous or heterozygous in an insertion mutation.

DETAILED DESCRIPTION OF THE INVENTION

The present invention is directed to novel methods of multiplexing amplification, detection and genotyping reactions, particularly polymerase chain reaction (PCR) reactions, although as described herein a variety of amplification techniques can be used. As will be appreciated by those in the art, there are a wide variety of configurations and assays that can be used; in general, the invention can be described as follows and is generally depicted in the Figures. There are two general methodologies: a "one step" and a "two step" process.

The "one step" process can generally be described as follows. A precircle probe is added to a target sequence from a sample that contains a first and a second target domain to form a hybridization complex. As outlined more fully below, these target domains in the target sequence can be directly adjacent, or can be separated by a gap of one or more nucleotides. The precircle probe comprises first and second targeting domains at its termini that are substantially complementary to the target domains of the target sequence. The precircle probe comprises one or optionally more universal priming sites, separated by a cleavage site, and a barcode sequence. If there is no gap between the target domains of the target sequence, and the 5' and 3' nucleotides of the precircle probe are perfectly complementary to the corresponding bases at the junction of the target domains, then the 5' and 3' nucleotides of the precircle probe are "abutting" each other and can be ligated together, using a ligase, to form a closed circular probe. The 5' and 3' end of a nucleic acid molecule are referred to as “abutting” each other when they are in contact close enough to allow the formation of a covalent bond, in the presence of ligase and adequate conditions.

This method is based on the fact that the two targeting domains of a precircle probe can be preferentially ligated together, if they are hybridized to a target strand such that they abut and if perfect complementarity exists at the two bases being ligated together. Perfect complementarity at the termini allows the formation of a ligation substrate such that the two termini can be ligated together to form a closed circular probe. If this complementarity does not exist, no ligation substrate is formed and the probes are not ligated together to an appreciable degree.

Once the precircle probes have been ligated, the unligated precircle probes and/or target sequences are optionally removed or inactivated. The closed circular probe is then linearized by cleavage at the cleavage site, resulting in a cleaved probe comprising the universal priming sites at the new termini of the cleaved probe. The addition of universal primers, an extension enzyme such as a polymerase, and NTPs results in amplification of the cleaved probe to form amplicons. These amplicons can be detected in a variety of ways. For example, in the case where barcode sequences are used, the amplicons containing the barcodes can then be added to universal biochip arrays, as is well known in the art, although as will be appreciated by those in the art, a number of other detection methods, including solution phase assays, can be run.

In a preferred embodiment, there is a gap between the target domains of the target sequence. In the case of a genotyping reaction, there is a single nucleotide gap, comprising the detection position, e.g. the SNP position. The addition of a single type of dNTP and a polymerase to the hybridization complex to “fill” the gap, if the dNTP is perfectly complementary to the detection position base. The dNTPs are optionally removed, and the ligase is added to form a closed circle probe. The cleavage, amplification and detection proceeds as above.

Alternatively, there may be a gap of more than one nucleotide between the target domains. In this case, as is more fully outlined below, either a plurality of dNTPs, a “gap oligonucleotide” as generally depicted in FIG. 3C or a precircle probe with a “flap” as is generally depicted in FIG. 30 can be used to accomplish the reaction.

The “two step” process is similar to the process outlined above. However, in this embodiment, after the precircle probe has been circularized, a single universal primer is added, in the presence of a polymerase and dNTPs, such that a new linear copy of the closed probe is produced, with new termini. This linearized closed probe is then amplified as more fully described below. The “two-step” process is particularly advantageous for reducing unwanted background signals arising from subsequent amplification reactions. This can be achieved by designing the cleavage sites into the precircle probes that when cleaved will prevent any amplification of any probe. Additional background reduction processes may also be incorporated into the compositions and methods of the present invention and are discussed in more detail herein.

The methods of the invention are particularly advantageous in reducing problems associated with cross-hybridizations and interactions between multiple probes, which can lead to unwanted background amplification. By circularlizing the precircle probes and treating the reaction with exonuclease, linear nucleic acids are degraded and thus cannot participate in amplification reactions. This allows the methods of the invention to be more robust and multiplexable than other amplification methods that rely on linear probes.

Accordingly, the present invention provides compositions and methods for detecting, quantifying and/or genotyping target nucleic acid sequences in a sample. In general, the genotyping methods described herein relate to the detection of nucleotide substitutions, although as will be appreciated by those in the art, deletions, insertions, inversions, etc. may also be detected.

As will be appreciated by those in the art, the sample solution may comprise any number of things, including, but not limited to, bodily fluids (including, but not limited to, blood, urine, serum, lymph, saliva, anal and vaginal secretions, perspiration and semen) or solid tissue samples, of virtually any organism, with mammalian samples being preferred and human samples being particularly preferred); environmental samples (including, but not limited to, air, agricultural, water and soil samples); biological warfare agent samples; research samples; purified samples, such as purified or raw genomic DNA, RNA, proteins, etc.; raw samples (bacteria, virus, genomic DNA, mRNA, etc.). As will be appreciated by those in the art, virtually any experimental manipulation may have been done on the sample.

There is no limitation as to the source of the template nucleic acid: it can be from a eukaryote, e.g., from a mammal, such as human, mouse, ovine, bovine, or from a plant; it can be from a prokaryote, e.g., bacteria, protozoan; and it can also be from a virus.

Nucleic acid specimens may be obtained from an individual of the species that is to be analyzed using either “invasive” or “non-invasive” sampling means. A sampling means is said to be “invasive” if it involves the collection of nucleic acids from within the skin or organs of an animal (including, especially, a murine, a human, an ovine, an equine, a bovine, a porcine, a canine, or a feline animal). Examples of invasive methods include blood collection, semen collection, needle biopsy, pleural aspiration, umbilical cord biopsy, etc. Examples of such methods are discussed by Kim, C. H, et al. (J. Virol. 66; 3879-3882 (1992)); Biswas, B. et al, (Annals NY Acad. Sci. 590:582-583 (1990)); Biswas, B. et al. (J. Clin. Microbiol. 29; 2228-2233 (1991)).

In contrast, a “non-invasive” sampling means is one in which the nucleic acid molecules are recovered from an internal or external surface of the animal. Examples of such “non-Invasive” sampling means include “swabbing,” collection of tears, saliva, urine, fecal material, sweat or perspiration, hair etc. As used herein, “swabbing” denotes contacting an applicator/collector (“swab”) containing or comprising an adsorbent material to a surface in a manner sufficient to collect live cells, surface debris and/or dead or sloughed off cells or cellular debris. Such collection may be accomplished by swabbing nasal, oral, rectal, vaginal or aural orifices, by contacting the skin or tear ducts, by collecting hair follicles, etc.

Methods for isolating nucleic acid specimens are known in the art, and will depend on the type of nucleic acid isolated. When the nucleic acid is RNA, care to avoid RNA degradation must be taken, e.g., by inclusion of RNAsin. For example, genomic DNA can be prepared from human cells as described, e.g., in U.S. Pat. No. 6,027,889.

The present invention provides compositions and methods for genotyping and/or detecting the presence or absence of target nucleic acid sequences in a sample. By “nucleic acid” or “oligonucleotide” or grammatical equivalents herein means at least two nucleotides covalently linked together. A nucleic acid of the present invention will generally contain phosphodiester bonds, although in some cases, as outlined below, such as in the design of probes, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91956)), phosphorothioate (Mag at al., Nucleic Acids Res. 19:1437 (1991); and U.S. Pat. No. 5,644, 048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci, USA 92:6097 (1995); non-Ionic backbones (U.S. Pat. Nos. 5,386, 023, 5,637,684, 5,602,240, 5,216,141 and 4,469,863; Kiedrowshi at al., Angew. Chem. Intl. Ed, English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed, Y. S. Sanghul and P. Dan Cook; Mesmeeker at al., Bioorganic & Medicinal Chem. Lett. 4:395 (1994); Jeffs at al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghul and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine, hypoxathanine, isocytosine, isoguanine, etc. A preferred embodiment utilizes nucleic acid probes comprising some proportion of uracil, as is more fully outlined below. One embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as labeled nucleosides. In addition, "nucleoside" includes non-naturally occurring analog structures. Thus for example the individual units of a peptide nucleic acid, each containing a base, are referred to herein as a nucleoside. Similarly, the term "nucleotide" (sometimes abbreviated herein as "NTP"), includes both ribonucleic acid and deoxyribonucleic acid (sometimes abbreviated herein as "dNTP"). While many descriptions below utilize the term "dNTP", it should be noted that in many instances NTPs may be substituted, depending on the template and the enzyme.

The compositions and methods of the invention are directed to the detection of target sequences. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of a genotyping or amplification reaction such as a ligated circularized probe, an amplicon from an amplification reaction such as PCR, etc. Thus, for example, a target sequence from a sample is amplified to produce a secondary target (amplicon) that is detected. Alternatively, as outlined more fully below, what may be amplified is the probe sequence, although this is not generally preferred. The target sequence may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence, sequence or quantity of a target sequence in a sample. Generally speaking, this term will be understood by those skilled in the art. Preferred target sequences range from about 20 to about 1,000,000 in size, more preferably from about 50 to about 10,000, with from about 40 to about 50,000 being most preferred.

If required, the target sequence is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

In addition, in some cases, for example when genomic DNA is to be used, it can be captured, such as through the use of precipitation or size exclusion techniques. Alternatively, DNA can be processed to yield uniform length fragments using techniques well known in the art, such as, e.g., hydrodynamic shearing or restriction endonucleases.

The target sequences of the present invention generally comprise at least a first and a second target domain. Target domains are portions of the target sequence. In general, each target domain may be any length, with the understanding that longer sequences are more specific. The proper length of the target domains in a probe will depend on factors including the GC content of the regions and their secondary structure. The considerations are similar to those used to identify an appropriate sequence for use as a primer, and are further described below. The length of the probe and GC content will determine the Tm of the hybrid, and thus the hybridization conditions necessary for obtaining specific hybridization of the probe to the template nucleic acid. These factors are well known to a person of skill in the art, and can also be tested in assays. An extensive guide to the hybridization of nucleic acids is found in Tijssen (1993), “Laboratory Techniques in biochemistry and molecular biology-hybridization with nucleic acid probes.” Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Highly stringent conditions are selected to be equal to the Tm point for a particular probe. Sometimes the term “Td” is used to define the temperature at which at least half of the probe dissociates from a perfectly matched target nucleic acid. In any case, a variety of estimation techniques for estimating the Tm or Td are available, and generally described in Tijssen, supra. Typically, G-C base pairs in a duplex are estimated to contribute about 3° C. to the Tm, while A-T base pairs are estimated to contribute about 2° C., up to a theoretical maximum of about 60-100° C. However, more sophisticated models of Tm and Td are available and appropriate in which G-C stacking interactions, solvent effects, the desired assay temperature and the like are taken, into account. For example, probes can be designed to have a dissociation temperature (Td) of approximately 60° C., using the formula: $Td=(((((3\times\#GC)+(2\times\#AT))\times37)-562)/\#bp)-5$; where #GC, #AT, and #bp are the number of guanine-cytosine base pairs, the number of adenine-thymine base pairs, and the number of total base pairs, respectively, involved in the annealing of the probe to the template DNA.

The stability difference between a perfectly matched duplex and a mismatched duplex, particularly if the mismatch is only a single base, can be quite small, corresponding to a difference in Tm between the two of as little as 0.5 degrees. See Tibanyenda, N. et al., Eur. J. Biochem. 139:19 (1984) and Ebel, S. et al., Biochem. 31:12083 (1992). More importantly, it is understood that as the length of the homology region increases, the effect of a single base mismatch on overall duplex stability decreases. Thus, where there is a likelihood that there will be mismatches between the probe and the target domains, it may be advisable to include a longer targeting domain in the probe.

Thus, the specificity and selectivity of the probe can be adjusted by choosing proper lengths for the targeting domains and appropriate hybridization conditions. When the template nucleic acid is genomic DNA, e.g., mammalian genomic DNA, the selectivity of the targeting domains must be high enough to identify the correct base in $3\times10^9$ in order to allow processing directly from genomic DNA. However, in situations in which a portion of the genomic DNA is isolated first from the rest of the DNA, e.g., by separating one or more chromosomes from the rest of the chromosomes, the selectivity or specificity of the probe is less important.

The length of the probe, and therefore the hybridization conditions will also depend on whether a single probe is hybridized to the template nucleic acid, or several probes. If several probes are used, and if all the probes are to be hybridized simultaneously to the template nucleic acid, then it is desirable to design the targeting domains of the different probes such that their Tm and/or Td is similar, such that they all the probes will hybridize specifically to the template nucleic acid. These conditions can be determined by a person of skill in the art, by taking into consideration the factors discussed above, as well those described within the context of the primers.

However, due to the length of the precircle probes, it is preferred that each target domain range in size from about 5 bases to about 100 bases, with from about 5 to about 40 being especially preferred. As will be appreciated by those in the art, the target domains may be the same length or different lengths, and may have greatly differing Tms. The terms “first” and “second” are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

As outlined herein, the target domains may be adjacent (i.e. contiguous) or separated, i.e. by a “gap”. If separated, the target domains may be separated by a single nucleotide or a plurality of nucleotides, with from 1 to about 2000 being preferred, and from 1 to about 500 being especially preferred, although as will be appreciated by those in the art, longer gaps may find use in some embodiments.

In a preferred embodiment, e.g. for genotyping reactions, as is more fully outlined below, the target sequence comprises a position for which sequence information is desired, generally referred to herein as the “detection position”. In a particularly preferred embodiment, the detection position is a single nucleotide, although in alternative embodiments, it may comprise a plurality of nucleotides, either contiguous with each other or separated by one or more nucleotides. By “plurality” as used herein is meant at least two. As used herein, the base which base pairs with the detection position base in a target is termed the “interrogation position”. In the case where a single nucleotide gap is used, the NTP that has perfect complementarity to the detection position is called an “interrogation NTP”.

It should be noted in this context that “mismatch” is a relative term and meant to indicate a difference in the identity of a base at a particular position, termed the “detection position” herein, between two sequences. In general, sequences that differ from wild type sequences are referred to as mismatches. However, and particularly in the case of SNPs, what constitutes “wild type” may be difficult to determine as multiple alleles can be relatively frequently observed in the population, and thus “mismatch” in this context requires the artificial adoption of one sequence as a standard. Thus, for the purposes of this invention, sequences are referred to herein as “perfect match” and “mismatch”. “Mismatches” are also sometimes referred to as “allelic variants”. The term “allele”, which is used interchangeably herein with “allelic variant” refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation. The term "allelic variant of a polymorphic region of a gene" refers to a region of a gene having one of several nucleotide sequences found in that region of the gene in other individuals of the same species.

The present invention provides precircle probes that hybridize to the target sequence as described herein. In general, probes of the present invention are designed to be complementary to a target sequence (either the target sequence of the sample or to other probe sequences, for example for universal primers and barcodes, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, etc. Alternatively, single strand binding protein may also be used to increase specificity.

These parameters may also be used to control non-specific binding, as is generally outlined in U.S. Pat. No. 5,681,697. Thus it may be desirable to perform certain steps at higher stringency conditions to reduce non-specific binding.

The design, preparation and use of the precircle probes according to the present invention will now be described in detail. As outlined above and explained more fully herein, the precircle probes of the present invention comprise at least first and second targeting domains and at least one universal priming site or sequence. Optionally, the precircle probes may further comprise one or more cleavage sites, barcode sequences, one or more restriction sites and/or labeling sequences.

A "universal" priming site is a site to which a universal primer will hybridize. In general, "universal" refers to the use of a single primer or set of primers for a plurality of amplification reactions. For example, in the detection or genotyping of a 100 different target sequences, all the precircle probes may share the identical universal priming sequences, allowing for the multiplex amplification of the 100 different probes using a single set of primers. This allows for ease of synthesis (e.g. only one set of primers is made), resulting in reduced costs, as well as advantages in the kinetics of hybridization. Most importantly, the use of such primers greatly simplifies multiplexing in that only two primers are needed to amplify a plurality of probes.

It should also be noted that "sets" of universal priming sequences/primers may be used. For example, in highly multiplexed reactions, it may be useful to use several sets of universal sequences, rather than a single set; for example, 100 different precircle probes may have the same priming sequences, and the second 100 a different set, etc.

As will be appreciated by those in the art, the precircle probes of the invention can take on a variety of configurations. As a preliminary matter, the precircle probes can be designed wherein the 5' and 3' termini of the targeting domains hybridize to adjacent nucleotides in the target sequence, or with gaps, as is more fully outlined below.

In a preferred embodiment, the precircle probe comprises two targeting domains that hybridize adjacently (i.e. without any gap nucleotides) to the target domains of the target sequence; this is sometimes referred to herein as an "abutting" precircle probe. This embodiment finds use in applications directed to both detection and/or genotyping.

In a preferred embodiment, the abutting precircle probe is used for detection of target sequences rather than genotyping. In this embodiment, the target sequence does not contain a particular detection position. Thus, abutting precircle probes are designed having 5' and 3' termini that hybridize, with perfect complementarity, to the directly adjacent target domains of the target sequence, such that the 5' and 3' termini will be abutting when the probe is hybridized to the target. Only if perfect complementarity exists at the 5' and 3' termini will the two ends of the abutting precircle probe ligate in the presence of a ligase, outlined below, to form a closed circular probe, which can then be further treated as outlined below. Of course, one of skill in the art will appreciate that the further any non-complementary sequence is from the site of ligation, the more likely the probe will be ligated.

In an alternative embodiment, an abutting precircle probe is used for genotyping of a detection position in the target sequence. In this embodiment, at least one of the abutting precircle probes comprises an interrogation base at either the 3' or 5' terminus of the precircle probe, e.g. a nucleotide that has perfect complementarity to the detection position of the target sequence. As will be appreciated by those in the art, either the 3' or 5' position can be used, as ligases will not ligate unless perfect basepairing between both termini exists. This embodiment is generally depicted in FIG. 3A.

In a particularly preferred embodiment, a plurality of abutting precircle probes are used. In one such embodiment, each abutting precircle probe comprises a different barcode sequence, as is more fully described below. For example, if the SNP position is biallelic, e.g. contains two different bases, two abutting precircle probes are used, each with a different interrogation base and a different barcode. Only if perfect complementarity exists between the interrogation base and the detection position will ligation occur. In this embodiment, the barcode sequence serves as a type of “label” or “tag”, identifying which base was present in the interrogation position. Alternatively, two abutting precircle probes are used having a different interrogation base but the same barcode. In this embodiment, the probes are employed in separate reaction mixtures and are worked up individually and detected as described herein, such that only the probe having perfect complementarity between the interrogation base and the detection position will ligate to form a circularized probe for detection. The latter embodiment can be used for, e.g., distinguishing between major and minor alleles of a gene of interest.

The precircle probes of the present invention may also comprise non-abutting targeting domains that do not hybridize adjacent to each other on the target sequence, i.e. the corresponding target domains of the target sequence are separated by a gap domain comprising one or more nucleotides. These probes may also be used in applications directed to detection, amplification and/or genotyping.

In one such embodiment, the precircle probe comprises two targeting domains that hybridize to two target domains in a target sequence separated by a single nucleotide gap domain (a single nucleotide gap position). Again, this embodiment finds use in applications directed to both detection and/or genotyping, with the latter being preferred.

In a preferred embodiment, a single-gap precircle probe is used for genotyping of target sequence. In this embodiment, the target sequence includes a particular detection position in the gap domain, and precircle probes are designed having targeting domains that hybridize, with perfect complementarity, to the single-nucleotide separated target domains of the target sequence. In this embodiment, a polymerase and one species of dNTP is added. If the dNTP is an interrogation dNTP, e.g., it has perfect complementarity to the detection position nucleotide, the polymerase will extend the precircle probe and form a ligation structure. The addition of a ligase as outlined herein then results in a circularized probe.

In this genotyping embodiment, there must be a plurality of separate reactions; that is, if the allele is biallelic, at least two reactions are done, each with a different dNTP. Similarly, triallelic positions are run with at least three reactions, etc. Each reaction mixture may be worked up separately and detected (e.g. added to an array), or they may be pooled, after circularization and removal of the extra dNTPs, and processed together. In a particularly preferred embodiment, all four dNTP reactions can be done simultaneously in separate reaction mixtures each with a different dNTP in order to identify the complementarity of an allele, and/or to provide a measure of the inherent background.

Alternatively, one of skill in the art will recognize that the single-gap precircle probe can also be used for detection and/or amplification simply by adding all four dNTPS simultaneously in the same reaction mixture along with a polymerase, which adds the dNTP with perfect complementarity to the detection position for subsequent ligation and amplification of the probe.

In another preferred embodiment, the precircle probe comprises two targeting domains that hybridize to two target domains separated by a gap domain comprising a plurality of nucleotides (an “oligo-gap” probe). As above, this embodiment finds use in either detection, amplification or genotyping reactions, and can rely on either probes containing a “flap-gap”, or on one or more additional oligonucleotides, sometimes referred to herein as “gap oligonucleotides” or “intervening oligonucleotides”.

In a particularly preferred embodiment, the oligo-gap precircle probe is used in amplification reactions. In this embodiment, as is generally depicted in FIG. 36, the reaction proceeds using a polymerase and dNTPs, in the presence of a ligase, to form a closed circle probe. The closed circle probe is then cleaved and amplified as outlined herein. One of skill in the art will appreciate that, by incorporating the same primer or primers in each of a plurality of probes to a plurality of different target sequences, one may simultaneously amplify multiple targets of interest in a single reaction vessel.

In another preferred embodiment, the multi nucleotide gap probe is used with one or more gap oligonucleotides. In this embodiment, as is generally depicted in FIG. 3C, rather than fill in the gap enzymatically, a substantially complementary gap oligonucleotide is used, which is then ligated on each end as outlined herein. As will be appreciated by those in the art, this embodiment can also rely on the use of a plurality of gap oligonucleotides.

In a preferred embodiment, the oligo-gap probe is used in genotyping reactions. In this embodiment, the detection position is in the “middle” (e.g. at any position internal to the gap) of the gap, and a “flap-gap” precircle probe is used. This embodiment is generally depicted in FIG. 3D. Unlike other reactions outlined herein, this embodiment relies on traditional hybridization methods that utilize the variation of stringency conditions (temperature, buffer conditions, etc.) to distinguish nucleotides at the detection position. Thus, the reaction is run under conditions that allow ligation only when the interrogation base is perfectly complementary to the detection base. That is, since all other parameters being equal, a perfectly complementary probe will be more stable and presumably have a slower off rate than a probe comprising a mismatch at any particular temperature. Accordingly, by using different probes, each with a different base at the interrogation position, the identification of the base at the detection position is elucidated. As outlined above, identical or different barcodes may be incorporated into the probes for subsequent detection in separate or, the same reaction mixtures, respectively. The differences can be amplified by using different temperatures. It should also be noted that in this embodiment, the length of the gap and the position of the interrogation base should be taken into account, as long gaps with interrogation bases far from the terminus may still hybridize and allow ligation to take place.

Alternatively, the same type of reaction can occur using one or more gap oligonucleotides, as depicted in FIG. 3C. In this embodiment, if the interrogation position is internal to the gap oligonucleotide, traditional stringency control is done. Alternatively, the interrogation position can be at either the 5' or 3' (or both, in the case of two SNP detection positions being close together) terminus of the gap oligonucleotide. This embodiment may find use in the case where due to specificity concerns, the target domains need to be long; yet in general, the longer the precircle probe, the more synthetic quality control issues are present.

Similarly, there may be genotyping reactions done with a plurality of gap oligonucleotides, again either with internal interrogation positions or interrogation positions at one or more termini of the gap oligonucleotides.

All of the foregoing embodiments of the claimed invention will benefit from reduction of background signals during subsequent amplification reactions. As described in more detail herein, one may render any unreacted probes and/or target sequences unavailable for amplification in a variety of ways. Preferred embodiments include, e.g. addition of exonuclease after ligation to degrade remaining linear nucleic acids, and/or the incorporation of appropriate labels (e.g. biotin) to allow separation and removal of either unreacted probe or the circularized probe:target complex, particularly when the latter comprises genomic DNA. Additional reduction steps are also contemplated and are discussed in further detail below including, e.g. extension of the circularized probe for further analysis of the extension product.

As is generally depicted in the figures and described herein, there are a variety of different embodiments to the present invention, including a "one step" and a "two step" process that may be employed after ligation of the precircle probe.

In the "one step" process, the closed circular probe is cleaved and amplified directly. In the "two step" process, the closed circular probe is first copied using a single universal priming site to produce an extension product of the closed circular probe. The closed circle probe is then removed along with the target sequence, and any uncircularized precircle probes. This extension product or "second strand" is now amplified, using the techniques outlined herein. This embodiment is generally pictured in FIGS. 5A-5I.

As outlined below, there are a wide variety of amplification methods which may be used, that may require either a single universal priming site or two priming sites. In a preferred embodiment, the amplification reaction is the PCR reaction and the precircle probes comprise two universal primers, one in each orientation, for use in PCR reactions. That is, as is known in the art, the orientation of primers is such to allow exponential amplification, such that the first universal priming sequence is in the "sense" orientation and the second universal priming sequence is in the "antisense" orientation.

In a preferred embodiment, the universal primers will be oriented as generally depicted in FIGS. 1-3 so that upon ligation and subsequent cleavage PCR amplification of the intervening targeting domains and optional barcode may be obtained. This embodiment is particularly preferred for, e.g., amplification of the target sequence(s). Alternatively, the primers may be oriented flanking a barcode as generally depicted in FIG. 4, such that only the barcode and primers may be exponentially amplified in subsequent PCR reactions. Additionally, the resulting amplicons may also be shortened by incorporation of cleavage sites as described in more detail below.

In general, the universal priming sequences/primers each range from about 12 to about 40 in length, with from about 15 to about 25 being preferred. Suitable universal priming sequences include, but are not limited to, those specifically exemplified herein.

Other amplification reactions, outlined below, may require one or more universal priming sequences as well.

In addition to the targeting domains and universal priming sites, the precircle probes preferably comprise at least a first cleavage site. Preferred cleavage sites are those that allow cleavage of nucleic acids in specific locations. Suitable cleavage sites include, but are not limited to, the incorporation of uracil or other ribose nucleotides, restriction endonuclease sites, etc.

In a preferred embodiment, the cleavage site comprises a uracil base. This allows the use of uracil-N-glycolylase, an enzyme which removes the uracil base while leaving the ribose intact. This treatment, combined with changing the pH (to alkaline) by heating, or contacting the site with an apurinic endonuclease that cleaves basic nucleosides, allows a highly specific cleavage of the closed circle probe.

In a preferred embodiment, a restriction endonuclease site is used, preferably a rare one. As will be appreciated by those in the art, this may require the addition of a second strand of nucleic acid to hybridize to the restriction site, as many restriction endonucleases require double stranded nucleic acids upon which to work. In one embodiment, the restriction site can be part of the primer sequence such that annealing the primer will make the restriction site double-stranded and allow cleavage.

When two priming sites are used, the cleavage site is preferably located between the two priming sites, such that upon cleavage, a linear probe is created with the priming sites at the termini, allowing the amplification of everything in between.

In some embodiments, more than one cleavage site is included. In this embodiment, as is generally depicted in FIG. 5F, there are a plurality of cleavage sites in the precircle probe. This may be done for a variety of reasons. In one embodiment, multiple cleavage sites can be used to render any probe incapable of amplification. This can be used to suppress unwanted PCR backgrounds as discussed herein in the two step method. In another embodiment, by cleaving off parts of the precircle probe, the required components for amplification are less. For example, by cleaving at the Junction of the target domains and the other components of the probe, only the barcode and universal primers need be amplified. A further advantage of locating the cleavage site other than between the two primers is that it can be used to prevent spurious amplification, particularly in the two-step process described above.

In addition to the targeting domains, cleavage site(s) and universal priming sites, the precircle probes of the invention may further comprise a barcode sequence. The terms "barcodes", "adapters", tags" and "zipcodes" have all been used to describe artificial sequences that are added to amplicons to allow separation of nucleic acid fragment pools. One preferred form of barcodes are hybridization barcodes. In this embodiment barcodes are chosen so as to allow hybridization to the complementary capture probes on a surface of an array. Barcodes serve as unique identifiers of the probe. In general, sets of barcodes and the corresponding capture probes are developed to minimize cross-hybridization with both each other and other components of the reaction mixtures, including the target sequences and sequences on the larger nucleic acid sequences outside of the target sequences (e.g. to sequences within genomic DNA). Other forms of barcodes are mass tags that can be separated using mass spectroscopy, electrophoretic tags that can be separated based on electrophoretic mobility, etc.

In general, both barcodes and the universal priming sequences/primers can be selected in a variety of ways, to avoid cross-hybridization, thereby preventing competition between individual primers and a target nucleic acid and preventing duplex formation of the primers in solution, and possible concatenation of the primers during PCR. If there is more than one constant region in the primer, the constant regions of the primer are selected so that they do not self-hybridize or form hairpin structures.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector™ program from Kodak.

In addition, the primers designed may be compared to the known sequences in the template nucleic acid, to avoid non specific hybridization of the primers to the template nucleic acid. For example, primers for use in detecting nucleotides in human genomic DNA can be "blasted" against human GenBank sequences, e.g., at the National Center for Biotechnology Information (NCBI) at http://www.ncbi.nlm.nih.gov/.

There are numerous algorithms that can be used for comparing sequences, such as probe sequences to template DNA sequences and probe and primer sequences. These algorithms include Sequencher, GCG, and the HGS Iris software. Any software which can align sequence and find regions of homology can be used, or the sequences can be compared manually.

A barcode for detection in array hybridization, e.g., high density arrays, are preferably around 20 nucleotides long and are described, e.g. in Shoemaker et al. (1996) Nature Genetics 14: 450. Barcode sequences should be maximally different yet still retain similar hybridization properties to facilitate simultaneous analysis on high-density oligonucleotide arrays. As described in Shoemaker et al., supra, an algorithm can be used to select sets of thousands (over 9,000) maximally distinguished 20mer barcode sequences that are predicted to have similar melting temperatures, no secondary structures and no extensive similarity between any two sequences (more than 5 mismatches). Moreover, hybridizations are sensitive and capable of detecting small differences in hybridization signal. For example, as further described in Shoemaker et al., supra, a two fold change in concentration was detected in the presence of a hybridization mixture with 120 oligonucleotides.

The use of barcodes allow the use of "universal arrays", e.g. arrays can be made with one set of capture probes that can be used in a wide variety of applications. The use of barcode sequences that allow the use of universal arrays has been described in limited contexts; see for example Chee et al., Nucl. Acid Res. 19:3301 (1991); Shoemaker et al., Nature Genetics 14:450 (1998); Barany, F. (1991) Proc. Natl. Acad. Sci. USA 88:189-193; EP 0 799 897 A1; WO 97/31256, all of which are expressly incorporated by reference.

As will be appreciated by those in the art, the length of the barcode sequences will vary, depending on the desired "strength" of binding and the number of different barcodes desired. In a preferred embodiment, barcode sequences range from about 6 to about 500 basepairs in length, with from about 8 to about 100 being preferred, and from about 10 to about 25 being particularly preferred.

In one embodiment, nucleic acid barcodes are used but not their hybridization properties. Rather, different length barcodes can be used, alternatively, the sequence the barcode is altered to result in different molecular weights. What is important is this embodiment is that each barcode have a different molecular weight. The barcodes are cleaved from the rest of the amplicon as described herein and subjected to mass spectroscopy analysis, or other techniques that rely on differential molecular weights for separation, such as gel electrophoresis.

Preferred barcode sequences (and thus their corresponding complementary capture probe sequences) are depicted in the examples and include those complementary to Affymetrix's GenFlex chip.

In a preferred embodiment, the precircle probes can also comprise additional elements. As is outlined herein, a labeling sequence may also be used. A labeling sequence has substantial complementarity to a label probe comprising labels, that can be added to the amplicons to label them, as is more fully outlined below. Again, it is preferred to use "universal" labeling sequences, or sets of sequences, to minimize the amount of sequence synthesis required and simplify multiplexing using multiple probes and/or multiple targets.

Accordingly, the invention provides precircle probes comprising a number of components, including, but not limited to, targeting domains, universal priming site(s), cleavage site(s), barcode sequences and labeling sequences. As is known in the art, these precircle probes (and the primers and capture probes outlined herein) can be made in a variety of ways. They may be may be synthesized chemically, e.g., according to the solid phase phosphoramidite triester method described by Beaucage and Caruthers (1981), Tetrahedron Letts., 22(20):1859-1862, e.g., using an automated synthesizer, as described in Needham-VanDevanter et al. (1984) Nucleic Acids Res., 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) J. Chrom. 255:137-149. The sequence of the synthetic oligonucleotides can be verified using the chemical degradation method of Maxam and Gilbert (1980) in Grossman and Moldave (eds.) Academic Press, NY, Methods in Enzymology 65:499-560. Custom oligos can also easily be ordered from a variety of commercial sources known to persons of skill.

Where probes are prepared by synthetic methods, it may be necessary to phosphorylate the 5' end of the probe, since oligonucleotide synthesizers do not usually produce oligonucleotides having a phosphate at their 5' end. The absence of a phosphate at the 5' end of the probe would otherwise prevent ligation of the 5' and 3' ends of the probe. Phosphorylation may be carried out according to methods well known in the art, using T4 polynucleotide kinase as described, e.g., in U.S. Pat. No. 5,593,840.

Probes and primers can also be prepared by recombinant methods, such as by including the probe in a plasmid that can be replicated in a host cell, e.g., bacteria, amplified and isolated by methods known in the art. The probe can then be cut out of the plasmid using a restriction enzyme that cuts around the probe. Alternatively, large amounts of probe can be prepared by PCR amplification using primers that are complementary to the 5' and 3' ends of the probe. The probe can then be further purified according to methods known in the art.

Probes can be prepared in one step, e.g., by synthetically synthesizing the whole probe. Alternatively, probes can be synthesized in at least two parts and linked together through linking oligonucleotides. For example, two parts of a precircle probe can be synthesized and can be linked together by using a bridging oligonucleotide, which contains sequences that are complementary to part A and part B of the probe. This is further described in Example 7. The bridging oligonucleotide is preferably at least from about 20 to about 50 nucleotides long, e.g., between 30 and 40 nucleotides. The bridging oligonucleotide preferably comprises at least about 10, more preferably, at least about 15 or 20 nucleotides that are complementary to each of part A and part B of the probe. The criteria to consider when designing bridging oligonucleotides are the same as those involved in designing a primer for hybridizing to a particular sequence, as described above. The ligation in the presence of the bridging oligonucleotide can be performed by regular ligation methods.

The methods of the invention proceed with the addition of the precircle probes to the target sequence. The targeting domains of the preclude probes hybridize to the target domains of the target sequence. If gaps exist, the reaction proceeds with the addition of one or more NTPs and an extension enzyme (or a gap oligo, as described herein). By "extension enzyme" herein is meant an enzyme that will extend a sequence by the addition of NTPs. As is well known in the art, there are a wide variety of suitable extension enzymes, of which polymerases (both RNA and DNA, depending on the composition of the target sequence and precircle probe) are preferred. Preferred polymerases are those that lack strand displacement activity, such that they will be capable of adding only the necessary bases at the end of the probe, without further extending the probe to include nucleotides that are complementary to a targeting domain and thus preventing circularization. Suitable polymerases include, but are not limited to, both DNA and RNA polymerases, including the Klenow fragment of DNA polymerase I, SEQUENASE 1.0 and SEQUENASE 2.0 (U.S. Biochemical), T5 DNA polymerase, Phi29 DNA polymerase and various RNA polymerases such as from *Thermus* sp., or Q beta replicase from bacteriophage, also SP6, T3, T4 and T7 RNA polymerases can be used, among others.

Even more preferred polymerases are those that are essentially devoid of a 5' to 3' exonuclease activity, so as to assure that the probe will not be extended past the 5' end of the probe. Exemplary enzymes lacking 5' to 3' exonuclease activity include the Klenow fragment of the DNA Polymerase and the Stoffel fragment of DNAPTaq Polymerase. For example, the Stoffel fragment of Taq DNA polymerase lacks 5' to 3' exonuclease activity due to genetic manipulations, which result in the production of a truncated protein lacking the N-terminal 289 amino acids. (See e.g., Lawyer et al., J. Biol. Chem., 264:6427-6437 [1989]; and Lawyer et al., PCR Meth. Appl., 2:275-287 [1993]). Analogous mutant polymerases have been generated for polymerases derived from *T. maritima*, Tsps17, TZ05, Tth and Taf.

Even more preferred polymerases are those that lack a 3' to 5' exonuclease activity, which is commonly referred to as a proof-reading activity, and which removes bases which are mismatched at the 3' end of a primer-template duplex. Although the presence of 3' to 5' exonuclease activity provides increased fidelity in the strand synthesized, the 3' to 5' exonuclease activity found in thermostable DNA polymerases such as Tma (including mutant forms of Tma that lack 5' to 3' exonuclease activity) also degrades single-stranded DNA such as the primers used in the PCR, single-stranded templates and single-stranded PCR products. The integrity of the 3' end of an oligonucleotide primer used in a primer extension process is critical as it is from this terminus that extension of the nascent strand begins. Degradation of the 3' end leads to a shortened oligonucleotide which in turn results in a loss of specificity in the priming reaction (i.e., the shorter the primer the more likely it becomes that spurious or non-specific priming will occur).

Yet even more preferred polymerases are thermostable polymerases. For the purposes of this invention, a heat resistant enzyme is defined as any enzyme that retains most of its activity after one hour at 40° C. under optimal conditions. Examples of thermostable polymerase which lack both 5' to 3' exonuclease and 3' to 5' exonuclease include Stoffel fragment of Taq DNA polymerase. This polymerase lacks the 5' to 3' exonuclease activity due to genetic manipulation and no 3' to 5' activity is present as Taq polymerase is naturally lacking in 3' to 5' exonuclease activity. Tth DNA polymerase is derived form *Thermus thermophilus*, and is available form Epicentre Technologies, Molecular Biology Resource Inc., or Perkin-Elmer Corp. Other useful DNA polymerases which lack 3' exonuclease activity include a Vent[R](exo−), available from New England Biolabs, Inc., (purified from strains of *E. coli* that carry a DNA polymerase gene from the archaebacterium *Thermococcus litoralis*), and Hot Tub DNA polymerase derived from *Thermus flavus* and available from Amersham Corporation.

Other preferred enzymes which are thermostable and deprived of 5' to 3' exonuclease activity and of 3' to 5' exonuclease activity include AmpliTaq Gold. Other DNA polymerases, which are at least substantially equivalent may be used like other N-terminally truncated *Thermus aquaticus* (Taq) DNA polymerase I. the polymerase named KlenTaq I and KlenTaq LA are quite suitable for that purpose. Of course, any other polymerase having these characteristics can also be used according to the invention.

The conditions for performing the addition of one or more nucleotides at the 3' end of the probe will depend on the particular enzyme used, and will generally follow the conditions recommended by the manufacturer of the enzymes used.

The nucleotides are preferably added to a final concentration from about 0.01 uM to about 100 uM, and preferably about 0.1 UM to 10 UM in the reaction. The concentration of ligase to add is described in the following section. Preferred, amounts of Taq DNA Polymerase Stoffel fragment include 0.05 u/ul. A typical reaction volume is about 10 to 20 ul. Preferred amounts of template and probe DNA are also described in the following section.

In a preferred embodiment, the template nucleic acids and probe(s) are combined in a reaction mixture together with a ligase, ligase buffer and polymerase. The template and probe(s) are then denatured, e.g., by incubation at 95° C. for about 5 to 10 minutes, and then annealed, e.g., by decreasing the temperature of the reaction. As described above, the annealing conditions will depend on the Tm of the homology regions. Polymerization and ligation are then done by adding nucleotides followed by incubation, e.g., for about 10 minutes at 65° C. Alternatively, the nucleic acids are first incubated together in the absence of enzymes, denatured and annealed and then the enzymes are added and the reactions are further incubated for, e.g., about 10 minutes at 65° C.

In order to decrease background signals that result from the attachment and ligation of a non complementary nucleotide, instead of adding a single dNTP to the polymerization reaction, one dNTP could be added along with the other three ddNTP's. These ddNTPs would not allow ligation but would render the reaction insensitive to small amounts of contaminating nucleotide.

Background signals may also result from the presence of the "correct" nucleotide in the reaction due to the presence of nucleotides in reagents, and its attachment to the probe. Contamination of reagents with nucleotides can be reduced by treatment of the reagents with an enzyme that degrades free nucleotides. Preferred enzymes include Apyrase and phosphotases, with the former being especially preferred. As described in the Examples, Apyrase is usually added to the reaction prior to the addition of the one or more dNTPs, at about a concentration of 0.5 mU/ul in a typical reaction of about 20 ul. Generally, the reactions are then incubated at 20° C. for a few minutes to up to 30 minutes. The enzyme is then denatured by incubation of the reaction for about 5 to 10 minutes at 95° C. Alternatively alkaline phosphatases may be used such as, e.g. shrimp alkaline phosphatase.

Ligation of the 3' and 5' ends of the probe(s) can be performed using an enzyme, or chemically. Preferably, ligation is carried out enzymatically using a ligase in a standard protocol. Many ligases are known and are suitable for use in the invention, e.g. Lehman, Science, 186: 790-797 (1974); Engler et al, DNA Ligases, pages 3-30 in Boyer, editor, The Enzymes, Vol. 15B (Academic Press, New York, 1982); and the like. Preferred ligases include T4 DNA ligase, T7 DNA ligase, *E. coli* DNA ligase, Taq ligase, Pfu ligase, and Tth ligase. Protocols for their use are well known, e.g. Sambrook et al (cited above); Barany, PCR Methods an Applications, 1: 5-16 (1991); Marsh et al, Strategies, 5: 73-76 (1992); and the like. Generally, ligases require that a 5' phosphate group be present for ligation to the 3' hydroxyl of an abutting strand. Preferred ligases include thermostable or (thermophilic) ligases, such as pfu ligase, Tth ligase, Taq ligase and Ampligase TM DNA ligase (Epicentre Technologies, Madison, Wis.). Ampligase has a low blunt end ligation activity.

The preferred ligase is one which has the least mismatch ligation and ligation across the gap activity. The specificity of ligase can be increased by substituting the more specific NAD+-dependant ligases such as *E. coli* ligase and (thermostable) Taq ligase for the less specific T4 DNA ligase. The use of NAD analogues in the ligation reaction further increases specificity of the ligation reaction. See, U.S. Pat. No. 5,508,179 to Wallace et al.

The conditions for carrying out the ligation will depend on the particular ligase used and will generally follow the manufacturer's recommendations. For example, preferred Ampligase concentrations are from about 0.0001 to about 0.001 u/ul, and preferably about 0.0005 u/ul. Preferred concentrations of probe nucleic acids are from about 0.001 to about 0.01 picomoles/ul and even more preferably, about 0.015 picomoles/ul. Preferred concentrations of template nucleic acids include from about 1 zeptomole/ul to about 1 attomole/ul, most preferably about 5 zeptomoles/ul. A typical reaction is performed in a total of about 20 ul.

In a preferred embodiment, the template nucleic acids and probe(s) are combined in a reaction mixture together with a ligase and ligase buffer. The template and probe(s) are then denatured, e.g., by incubation at 95° C. for about 5 to 10 minutes, and then annealed, e.g., by decreasing the temperature of the reaction. The annealing conditions will depend on the Tm of the homology regions, as described elsewhere herein. Annealing can be carried out by slowing reducing the temperature from 95° C. to about the Tm or several degrees below the Tm. Alternatively, annealing can be carried out by incubating the reaction at a temperature several degrees below the Tm for, e.g., about 10 to about 60 minutes. For example, the annealing step can be carried out for about 15 minutes. Ligation can be then carried out by incubation the reactions for about 10 minutes at 65° C.

Alternatively, the nucleic acids are denatured and annealed in the absence of the ligase, and the ligase is added to the annealed nucleic acids and then incubated, e.g., for about 10 minutes at 65° C. This embodiment is preferably for non heat stable ligases.

As mentioned previously, unreacted probes can contribute to backgrounds from undesired non-specific amplification. In a preferred embodiment, any unreacted precircle probes and/or target sequences are rendered unavailable for amplification. This can be done in a variety of ways, as will be appreciated by those in the art. In one embodiment, exonucleases are added, that will degrade any linear nucleic acids, leaving the closed circular probes. Suitable 3'-exonucleases include, but are not limited to, exo I, exo III, exo VII, exo V, and polymerases, as many polymerases have excellent exonuclease activity, etc.

In another preferred embodiment, terminal transferase can be used to add nucleotides comprising separation labels such as biotin to any linear molecules, and then the mixture run through a strepavidin system to remove any linear nucleic acids, leaving only the closed circular probes. For example, when genomic DNA is used as the target, this may be biotinylated using a variety of techniques, and the precircle probes added and circularized. Since the circularized probes are catenated on the genomic DNA, the linear unreacted precircle probes can be washed away. The closed circle probes can then be cleaved, such that they are removed from the genomic DNA, collected and amplified. Similarly, terminal transferase may be used to add chain terminating nucleotides, to prevent extension and/or amplification. Suitable chain terminating nucleotides include, but are not limited to, dideoxy-triphosphate nucleotides (ddNTPs), halogenated dNTPs and acyclo nucleotides (NEN). These latter chain terminating nucleotide analogs are particularly good substrates for Deep vent (exo$^-$) and thermosequenase.

In addition, known separation techniques based on size can be used to separate the genomic DNA with the associated closed circle probe and the linear probes.

In addition, it is important to note that there may be PCR background that results from polymerase extension of the 3' end of the probe along the template. This background may be reduced in order to obtain high levels of enrichment of the specifically ligated probes. The following represent examples of PCR background suppression techniques. These techniques may be based on the elimination of the original probe and/or template nucleic acids.

In one embodiment of the two step process, after ligating the probes, a biotinylated primer is introduced which is complementary to the first probe primer. An extension polymerization reaction is then performed resulting in either a full length probe complement (in the case of the ligated probes) or a truncated probe missing the second primer site (in the case of the unligated probes) (see, e.g., FIG. 1). This product can then be captured on magnetic streptavidin beads and the template and original probes washed away. The PCR can then performed using this "clean" product. Because the unligated probe products will lack the second primer site, they will not amplify. Numerous examples of such a reaction are provided in the Examples. Biotinylated probes can be synthesized on an oligonucleotide synthesizer.

In another embodiment, the probe is made to contain a uracil base between the first primer sequence and the first homology sequence. After a run-off reaction as described above (the two step process), uracil-N-glycosylase can be used to induce strand scission on all the original probes stopping any PCR. Only the full length extension products will amplify.

In yet another embodiment, instead of the elongation reaction as described above, a rolling circle polymerization reaction can be performed. In this way many concatenated copies of the ligated probes can be made, effectively increasing the concentration of the ligated probes relative to the unligated probes and leading to a lower level of amplified un-ligated probe. This technique is described, e.g., in Example 2, and in U.S. Pat. No. 5,854,033 by Lizardi et al.

Yet other methods to reduce background amplification, i.e., non specific amplification, include using an exonuclease to degrade any unligated probe. Prior to amplification, any exonuclease must be eliminated from the reaction mixture, e.g., by heat denaturation of the nuclease.

Once a closed circular probe is formed, it can follow one of two fates, as described herein. In a preferred embodiment, any remaining linear probes, sequences and primers are removed, and the closed circle probe is cleaved as outlined herein, and amplified as outlined below, to form amplicons (the "one-step" process). Alternatively, a linear copy of the closed probe is made, and it is this linear copy (comprising new termini) that is used in the amplification reactions.

Once cleaved, the linearized cleaved probes can then be amplified. However, in the genotyping "gap" embodiments, it is useful to first remove or degrade any dNTPs prior to the addition of the interrogation dNTP. This can be done in a variety of ways, as outlined herein, generally by the addition of nucleotide degrading enzymes, including, but not limited to, apyrase, as outlined herein.

Once cleaved, the linearized cleaved probes can then be amplified. As will be appreciated by those in the art, there are a wide variety of suitable amplification techniques that can be used to form the amplicons of the invention that are then detected, generally via the use of arrays, as is more fully outlined below. Suitable amplification methods include both target amplification and signal amplification and include, but are not limited to, polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), and invasive cleavage technology. All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a cleaved probe is added to a reaction mixture that comprises the necessary amplification components, and amplicons are formed.

In general, the amplicon comprises a detectable label, such as a fluorescent label, which is either incorporated by the enzyme or present on the original primer. As required, the unreacted primers are removed, in a variety of ways, as will be appreciated by those in the art. The hybridization complex is then disassociated, and the amplicon is detected and optionally quantitated by an array. In some cases, the first amplicon serves as a target sequence for a secondary reaction, which then produces a, number of second amplicons, which can be detected as outlined herein.

Accordingly, the reaction starts with the addition of a primer nucleic acid to the target sequence which forms a hybridization complex. Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identity of the enzyme will depend on the amplification technique used, as is more fully outlined below. Similarly, the modification will depend on the amplification technique, as outlined below.

Once the enzyme has modified the primer to form an amplicon, the hybridization complex is disassociated. In one aspect, dissociation is by modification of the assay conditions. In another aspect, the modified primer no longer hybridizes to the target nucleic acid and dissociates. Either one or both of these aspects can be employed in signal and target amplification reactions as described below. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 15 to 50 cycles being especially preferred. In certain embodiments, e.g., where one desires quantifying a specific sequence, it may be desirable to perform several parallel amplification reactions each using a different number of cycles, such that at least in one set of reactions, the amplification reaction will be in the exponential phase, and will therefore provide a direct correlation between the level of amplified product and the number of original sequences.

After a suitable time of amplification, unreacted primers are removed, if required, in a variety of ways, as will be appreciated by those in the art, and the hybridization complex is disassociated. In general, the amplicon comprises a detectable label, such as a fluorescent label, which is either incorporated by the enzyme or present on the original primer, and the amplicon is added to an array as outlined below. Detection proceeds via detection of the label as an indication of the presence, absence or amount of the target sequence, as is more fully outlined below.

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), transcription mediated amplification (TMA) and nucleic acid sequence based amplification (NASBA).

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "Immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostable polymerase such as Taq I polymerase and thermal cycling.

Accordingly, the PCR reaction requires at least one PCR primer, a polymerase, and a set of dNTPs, As outlined herein, the primers may comprise the label, or one or more of the dNTPs may comprise a label.

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2' deoxyadenosine 5'-O-(1-thiotriphosphate), 5-methyldeoxycytidine 5'-triphosphate, 2'-deoxyuridine 5'-triphosphate, adn 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'-3' exonuclease activity. However, if less than all the nucleotides are substituted, the polymerase preferably lacks 5'-3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindIII, AvaI, Fnu4HI, TthIIII, NcII, BstXI, BamHI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'-3', thereby creating another newly synthesized strand. The polymerase chosen should be able to initiate 5'-3' polymerization at a nick site, should also displace the polymerized strand downstream from the nick, and should lack 5'-3' exonuclease activity (this may be additionally accomplished by the addition of a blocking agent). Thus, suitable, polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

In a preferred embodiment, the target amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques may be described as follows. A single stranded target nucleic acid, usually an RNA target sequence (sometimes referred to herein as "the first target sequence" or "the first template", which is the cleaved circular probe), is contacted with a first primer, generally referred to herein as a "NASBA primer" (although "TMA primer" is also suitable). Starting with a DNA target sequence is described below. These primers generally have a length of 25-100 nucleotides, with NASBA primers of approximately 50-75 nucleotides being preferred. The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT. When the amplification reaction is TMA, the reverse transcriptase enzyme further comprises a RNA degrading activity as outlined below.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from *E. coli* and calf thymus.

The ribonuclease activity degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage *Salmonella* phage sp6, or Pseudomonase phage gh-1.

In some embodiments, TMA and NASBA are used with starting DNA target sequences. In this embodiment, it is necessary to utilize the first primer comprising the RNA polymerase promoter and a DNA polymerase enzyme to generate a double stranded DNA hybrid with the newly synthesized strand comprising the promoter sequence. The hybrid is then denatured and the second primer added.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

In this way, a number of secondary target molecules (e.g., amplicons) are made. As is more fully outlined below, these reactions (that is, the products of these reactions) can be detected in a number of ways.

In embodiments in which the unreacted linear probes are removed, an alternative to target amplification is signal amplification based on interactions with a specific probe sequence such as a barcode sequence. In a preferred embodiment, the amplification technique is signal amplification. Signal amplification involves the use of limited number of target molecules as templates to either generate multiple signalling probes or allow the use of multiple signalling probes. Signal amplification strategies include OLA, CPT, QβR and invasive cleavage technology.

In a preferred embodiment, single base extension (SBE; sometimes referred to as "minisequencing") is used for amplification. Briefly, SBE is a technique that utilizes an extension primer that hybridizes to the target nucleic acid, in this case to at least the barcode sequence. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target strand. Generally, the nucleotide is derivatized such that no further extensions can occur, so only a single nucleotide is added. However, for amplification reactions, this may not be necessary. Once the labeled nucleotide is added, detection of the label proceeds as outlined herein. See generally Sylvanen et al., Genomics 8:654-692 (1990); U.S. Pat. Nos. 5,846,710 and 5,888,819; Pastinen et al., Genomics Res. 7(6):606-614 (1997); all of which are expressly incorporated herein by reference.

The reaction is initiated by introducing the assay complex comprising the cleaved circular probe to a solution comprising a first nucleotide, frequently an nucleotide analog. By "nucleotide analog" in this context herein is meant a deoxynucleoside-triphosphate (also called deoxynucleotides or dNTPs, i.e. dATP, dTTP, dCTP and dGTP), that is further derivatized to be chain terminating. As will be appreciated by those in the art, any number of nucleotide analogs may be used, as long as a polymerase enzyme will still incorporate the nucleotide at the interrogation position. Preferred embodiments utilize dideoxy-triphosphate nucleotides (ddNTPs). Generally, a set of nucleotides comprising ddATP, ddCTP, ddGTP and ddTTP is used, at least one of which includes a label, and preferably all four.

In a preferred embodiment, the nucleotide analogs comprise a detectable label, which can be either a primary or secondary detectable label as outlined below. However, the enzymatic incorporation of nucleotides comprising fluorophores is poor under many conditions; accordingly, preferred embodiments utilize secondary detectable labels.

In addition to a first nucleotide, the solution also comprises an extension enzyme, generally a DNA polymerase. Suitable DNA polymerases include, but are not limited to, the Klenow fragment of DNA polymerase I, SEQUENASE 1.0 and SEQUENASE 2.0 (U.S. Biochemical), T5 DNA polymerase and PhI29 DNA polymerase. If the NTP is complementary to the base of the detection position of the target sequence, which is adjacent to the extension primer, the extension enzyme will add it to the extension primer. Thus, the extension primer is modified, i.e. extended, to form a modified primer, sometimes referred to herein as a "newly synthesized strand".

A limitation of this method is that unless the target nucleic acid is in sufficient concentration, the amount of unextended primer in the reaction greatly exceeds the resultant extended-labeled primer. The excess of unextended primer competes with the detection of the labeled primer in the assays described herein. Accordingly, when SBE is used, preferred embodiments utilize methods for the removal of unextended primers as outlined herein.

One method to overcome this limitation is thermocycling minisequencing in which repeated cycles of annealing, primer extension, and heat denaturation using a thermocycler and thermo-stable polymerase allows the amplification of the extension probe which results in the accumulation of extended primers. For example, if the original unextended primer to target nucleic acid concentration is 100:1 and 100 thermocycles and extensions are performed, a majority of the primer will be extended.

Thus, the SBE reaction requires, in no particular order, an extension primer, a polymerase and dNTPs, at least one of which is labeled.

In a preferred embodiment, the signal amplification technique is OLA. OLA, which is referred to as the ligation chain reaction (LCR) when two-stranded substrates are used, involves the ligation of two smaller probes into a single long probe, using the target sequence as the template. In LCR, the ligated probe product becomes the predominant template as the reaction progresses. The method can be run in two different ways; in a first embodiment, only one strand of a target sequence is used as a template for ligation; alternatively, both strands may be used. See generally U.S. Pat. Nos. 5,185,243, 5,679,524 and 5,573,907; EP 0 320 308 31; EP 0 336 731 31; EP 0 439 182 B1; WO 90/01069; WO 89/12696; WO 97/31256; and WO 89/09835, and U.S. Ser. Nos. 60/078,102 and 60/073,011, all of which are incorporated by reference.

In a preferred embodiment, the cleaved circular probe comprises a first target domain and a second target domain, which are adjacent and contiguous, and should span the barcode sequence. A first OLA primer and a second OLA primer nucleic acids are added, that are substantially complementary to their respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two OLA primers are then covalently attached, for example using a ligase enzyme such as is known in the art, to form a modified primer. This forms a first hybridization complex comprising the ligated probe and the target sequence. This hybridization complex is then denatured (disassociated), and the process is repeated to generate a pool of ligated probes.

In a preferred embodiment, OLA is done for two strands of a double-stranded target sequence. The target sequence is denatured, and two sets of probes are added: one set as outlined above for one strand of the target, and a separate set (i.e. third and fourth primer probe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

Again, as outlined above, the detection of the LCR reaction can also occur directly, in the case where one or both of the primers comprises at least one detectable label, or indirectly, using sandwich assays, through the use of additional probes; that is, the ligated probes can serve as target sequences, and detection may utilize amplification probes, capture probes, capture extender probes, label probes, and label extender probes, etc.

In a preferred embodiment, the signal amplification technique is invasive cleavage technology, which is described in a number of patents and patent applications, including U.S. Pat. Nos. 5,846,717; 5,614,402; 5,719,028; 5,541,311; and 5,843,669, all of which are hereby incorporated by reference in their entirety. Invasive cleavage technology is based on structure-specific nucleases that cleave nucleic acids in a site-specific manner. Two probes are used: an "invader" probe and a "signalling" probe, that adjacently hybridize to a target sequence with overlap. For mismatch discrimination, the invader technology relies on complementarity at the overlap position where cleavage occurs. The enzyme cleaves at the overlap, and releases the "tail" which may or may not be labeled. This can then be detected.

Generally, invasive cleavage technology may be described as follows. A cleaved circular probe is recognized by two distinct probes. A first probe, generally referred to herein as an "invader" probe, is substantially complementary to a first portion of the cleaved circular probe. In this embodiment, a barcode is not necessary, as the first portion of the cleaved circular probe can include a target specific domain. A second probe, generally referred to herein as a "signal probe", is partially complementary to a target domain of the cleaved circular probe; the 3' end of the signal oligonucleotide is substantially complementary to the cleaved circular probe while the 5' end is non-complementary and preferably forms a single-stranded "tail" or "arm". The non-complementary end of the second probe preferably comprises a "generic" or "unique" sequence, e.g. a barcode sequence, that is used to indicate the presence or absence of the target nucleic acid, as described below. The barcode sequence of the second probe preferably comprises at least one detectable label, although as outlined herein, since this detection sequence can function as a target sequence for a capture probe, sandwich configurations utilizing label probes as described herein may also be done.

Hybridization of the first and second oligonucleotides near or adjacent to one another on the target nucleic acid forms a number of structures. In a preferred embodiment, a forked cleavage structure forms and is a substrate of a nuclease which cleaves the detection sequence from the signal oligonucleotide. The site of cleavage is controlled by the distance or overlap between the 3' end of the invader oligonucleotide and the downstream fork of the signal oligonucleotide. Therefore, neither oligonucleotide is subject to cleavage when misaligned or when unattached to target nucleic acid.

In a preferred embodiment, the nuclease that recognizes the forked cleavage structure and catalyzes release of the tail is thermostable, thereby, allowing thermal cycling of the cleavage reaction, if desired. Preferred nucleases derived from thermostable DNA polymerases that have been modified to have reduced synthetic activity which is an undesirable side-reaction during cleavage are disclosed in U.S. Pat. Nos. 5,719,028 and 5,843,669, hereby expressly by reference. The synthetic activity of the DNA polymerase is reduced to a level where it does not interfere with detection of the cleavage reaction and detection of the freed tall. Preferably the DNA polymerase has no detectable polymerase activity. Examples of nucleases are those derived from *Thermus aquaticus, Thermus flavus*, or *Thermus thermophilus*.

In another embodiment, thermostable structure-specific nucleases are Flap endonucleases (FENS) selected from FEN-1 or FEN-2 like (e.g. XPG and RAD2 nucleases) from Archaebacterial species, for example, FEN-1 from *Methanococcus jannaschii, Pyrococcus furiosis, Pyrococcus woesei*, and *Archaeogtobus fulgidus*. (U.S. Pat. No. 5,843,669 and Lyamichev et al., 1999. Nature Biotechnology 17:292-297; both of which are hereby expressly by reference).

In a preferred embodiment, the nuclease is AfuFEN1 or PfuFEN1 nuclease. To cleave a forked structure, these nucleases require at least one overlapping nucleotide between the signal and invasive probes to recognize and cleave the 5' end of the signal probe. To effect cleavage the 3'-terminal nucleotide of the invader oligonucleotide is not required to be complementary to the target nucleic acid. In contest, mismatch of the signal probe one base upstream of the cleavage site prevents creation of the overlap and cleavage.

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety.

Generally, CPT may be described as follows. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. In general, a first probe sequence (e.g. one end of the primer) comprises a capture tag, such as biotin, and the other (the second probe sequence) at least one label. Upon completion of the reaction, the binding partner of the capture tag (e.g. streptavidin) is used to remove all unreacted probes and the cleaved first probe sequences, leaving behind the second probe sequence, which can be detected, for example by binding to an array. In the present invention, the CPT primers and precircle probes are constructed such that it is the barcode sequence that serves as the second probe sequence.

By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal. As used herein, the scissile linkage, is any connecting chemical structure which joins two probe sequences and which is capable of being selectively cleaved without cleavage of either the probe sequences or the sequence to which the scissile probe is hybridized. The scissile linkage may be a single bond, or a multiple unit sequence. As will be appreciated by those in the art, a number of possible scissile linkages may be used.

In a preferred embodiment, the scissile linkage comprises RNA. This system, previously described in as outlined above, is based on the fact that certain double-stranded nucleases, particularly ribonucleases, will nick or excise RNA nucleosides from a RNA:DNA hybridization complex. Of particular use in this embodiment is RNAseH, Exo III, and reverse transcriptase.

CPT may be done enzymatically or chemically. That is, in addition to RNAseH, there are several other cleaving agents which may be useful in cleaving RNA (or other nucleic acid) scissile bonds. For example, several chemical nucleases have been reported; see for example Sigman et al., Annu. Rev. Biochem, 1990, 59, 207-236; Sigman et al., Chem. Rev, 1993, 93, 2295-2316; Bashkin et al., J. Org. Chem. 1990, 55, 5125-5132; and Sigman et al., Nucleic Acids and Molecular Biology, vol. 3, F. Eckstein and D. M. J. Lilley (Eds), Springer-Verlag, Heidelberg 1989, pp. 13-27; all of which are hereby expressly incorporated by reference.

The first step of the CPT method requires hybridizing a primary scissile primer (also called a primary scissile probe) to the target. This is preferably done at a temperature that allows both the binding of the longer primary probe and disassociation of the shorter cleaved portions of the primary probe, as will be appreciated by those in the art.

In general, the scissile probes are introduced in a molar excess to their targets, with ratios of scissile probe:target of at least about 100:1 being preferred, at least about 1000:1 being particularly preferred, and at least about 10,000:1 being especially preferred. In some embodiments the excess of probe: target will be much greater. In addition, ratios such as these may be used for all the amplification techniques outlined herein.

Once the hybridization complex between the primary scissile probe and the target has been formed, the complex is subjected to cleavage conditions. As will be appreciated, this depends on the composition of the scissile probe; if it is RNA, RNAseH is introduced. It should be noted that under certain circumstances, such as is generally outlined in WO 95/00666 and WO 95/00667, hereby incorporated by reference, the use of a double-stranded binding agent such as RNAseH may allow the reaction to proceed even at temperatures above the Tm of the primary probe:target hybridization complex. Accordingly, the addition of scissile probe to the target can be done either first, and then the cleavage agent or cleavage conditions introduced, or the probes may be added in the presence of the cleavage agent or conditions.

The cleavage conditions result in the separation of the two (or more) probe sequences of the primary scissile probe. As a result, the shorter probe sequences will no longer remain hybridized to the target sequence, and thus the hybridization complex will disassociate, leaving the target sequence intact.

The optimal temperature for carrying out the CPT reactions is generally from about 5° C. to about 25° C. below the melting temperatures of the probe:target hybridization complex. This provides for a rapid rate of hybridization and high degree of specificity for the target sequence. The Tm of any particular hybridization complex depends on salt concentration, G-C content, and length of the complex, as is known in the art and described herein.

These steps are repeated by allowing the reaction to proceed for a period of time. The reaction is usually carried out for about 15 minutes to about 1 hour. Generally, each molecule of the target sequence will turnover between 100 and 1000 times in this period, depending on the length and sequence of the probe, the specific reaction conditions, and the cleavage method. For example, for each copy of the target sequence present in the test sample 100 to 1000 molecules will be cleaved by RNAseH. Higher levels of amplification can be obtained by allowing the reaction to proceed longer, or using secondary, tertiary, or quaternary probes, as is outlined herein.

Upon completion of the reaction, generally determined by time or amount of cleavage, the uncleaved scissile probes must be removed or neutralized prior to detection, such that the uncleaved probe does not bind to a detection probe, causing false positive signals. As will be appreciated by those in the art, this may be done in a variety of ways.

In a preferred embodiment, the separation is facilitated by the use of beads containing the primary probe. Thus, when the scissile probes are attached to beads, removal of the beads by filtration, centrifugation, the application of a magnetic field, electrostatic interactions for charged beads, adhesion, etc., results in the removal of the uncleaved probes.

After removal of the uncleaved probe, as required, detection proceeds via the addition of the cleaved probe sequences to the array compositions, as outlined below. In general, the cleaved probe is bound to a capture probe, either directly or indirectly, and the label is detected. In a preferred embodiment, no higher order probes are used, and detection is based on the probe sequence(s) of the primary primer. In a preferred embodiment, at least one, and preferably more, secondary probes (also referred to herein as secondary primers) are used; the secondary probes hybridize to the domains of the cleavage probes; etc.

Thus, CPT requires, again in no particular order, a first CPT primer comprising a first probe sequence, a scissile linkage and a second probe sequence; and a cleavage agent.

In this manner, CPT results in the generation of a large amount of cleaved primers, which then can be detected as outlined below.

In all of the amplification methods described herein, labels are used. In general, either direct or indirect detection of the target products (e.g. amplicons) can be done. "Direct" detection as used in this context, as for the other reactions outlined herein, requires the incorporation of a label, in this case a detectable label, preferably an optical label such as a fluorophore, into the amplicon, with detection proceeding as outlined below. In this embodiment, the label(s) may be incorporated in a variety of ways: (1) the primers comprise the label(s), for example attached to the base, a ribose, a phosphate, or to analogous structures in a nucleic acid analog; (2) modified nucleosides are used that are modified at either the base or the ribose (or to analogous structures in a nucleic acid analog) with the label(s); these label-modified nucleosides are then converted to the triphosphate form and are incorporated into a newly synthesized strand by an extension enzyme such as a polymerase; (3) modified nucleotides are used that comprise a functional group that can be used (post-enzymatic reaction) to add a detectable label; (4) modified primers are used that comprise a functional group that can be used to add a detectable label in a similar manner; or (5) a label probe that is directly labeled and hybridizes to a portion of the amplicon can be used. Any of these methods result in a detectable amplicon.

Thus, the modified strands comprise a detection label. By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, by spectroscopic, photochemical, biochemical, immunochemical, electrical, optical or chemical means. Useful labels in the present invention include spectral labels such as fluorescent dyes (e.g., fluorescein isothiocyanate, Texas red, rhodamine, dixogenin, biotin, and the like), radiolabels (e.g., 3H, 125I, 35S, 14C, 32P, 33P, etc.), enzymes (e.g., horse-radish peroxidase, alkaline phosphatase etc.) spectral calorimetric labels such as colloidal gold or colored glass or plastic (e.g. polystyrene, polypropylene, latex, etc.) beads; magnetic, electrical, thermal labels; and mass tags. Labels can also include enzymes (horseradish peroxidase, etc.) and magnetic particles. Preferred labels include chromophores or phosphors but are preferably fluorescent dyes. Suitable dyes for use in the invention include, but are not limited to, Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone mines anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay of the invention, or which can be modified to incorporate such functionalities include, e.g., dansyl chloride; fluoresceins such as 3,6-dihydroxy-9-phenylxanthydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl) palmitate; dansyl phosphatidylethanolamine; N,N'-dioctadecyl oxacarbocyanine: N,N'-dihexyl oxacarbocyanine; merocyanine, 4-(3'-pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis (2-methyl-5-phenyl-oxazolyl))benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-(p-(2benzimidazolyl)-phenyl)maleimide; N-(4-fluoranthyl)maleimide; bis(hornovanillic acid); resazarin; 4-chloro-7-nitro-2,1,3-benzooxadiazole; merocyanine 540; resorufin; rose bengal; 2,4-diphenyl-3 (2H)-furanone, fluorescent lanthanide complexes, including those of Europium and Terbium, fluorescein, rhodamine, tetramethylrhodamine, eosin, erythrosin, coumarin, methylcoumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference. Other labels are described in U.S. Ser. No. 60/242,901, filed Oct. 24, 2000, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises a primary detection label (for example, attached to the NTP and therefore to the amplicon) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

In one embodiment, the label is a mass tag, as is more fully outlined below.

Once labeled, if applicable, the amplicons comprising the barcodes of the invention are detected. All of the methods and compositions herein are drawn to methods of detecting, quantifying and/or determining the base at the detection position of a target nucleic acid, generally by having differential reactions occur depending on the presence or absence of a mismatch. The reaction products are generally detected on arrays as is outlined herein, although a number of different detection methods may be used.

Accordingly, the present invention provides methods and compositions useful in the detection of nucleic acids. As will be appreciated by those in the art, the compositions of the invention can take on a wide variety of configurations, as is generally outlined in the Figures. As is more fully outlined below, preferred systems of the invention work as follows. An amplicon is attached (via hybridization) to an array site. This attachment is generally a direct hybridization between a barcode on the amplicon and a corresponding capture probe, although in some instances, the system can rely on indirect "sandwich" complexes using capture extender probes as are known in the art. In a preferred embodiment, the target sequence (e.g. the amplicon) itself comprises the labels. Alternatively, a label probe is added, that will hybridize to a label sequence on the amplicon, forming an assay complex. The capture probes of the array are substantially (and preferably perfectly) complementary to the barcode sequences.

The terms length determination, separation-by-length assay, and separation-by-length assay medium are taken collectively to mean a process and its related apparatus that achieves separation of DNA fragments on the basis of length, size, mass, or any other physical property. This includes generally, liquid chromatography, electrophoresis and direct mass spectrometry; more particularly, high performance liquid chromatography (HPLC) and capillary electrophoresis or gel electrophoresis, and MALDI-TOF MS respectively.

Where the tag is a hybridization tag, in order to keep high specificity, hybridization is normally carried out under the most stringent conditions, achieved through various combinations of temperature, salts, detergents, solvents, chaotropic agents, and denaturants. Such conditions are further described herein in context of the homology regions and primers.

Multiple sample nucleic acid hybridization analysis has been conducted on a variety of filter and solid support formats (see G. A. Beltz et al., in Methods in Enzymology, Vol. 100, Part B, R. Wu, L. Grossmam, K. Moldave, Eds., Academic Press, New York, Chapter 19, pp. 266-308, 1985). One format, the so-called "dot blot" hybridization, involves the non-covalent attachment of target DNAs to a filter, which are subsequently hybridized with a radioisotope labeled probe(s). "Dot blot" hybridization gained wide-spread use, and many versions were developed (see M. L. M. Anderson and B. D. Young, in Nucleic Acid Hybridization—A Practical Approach, B. D. Hames and S. J. Higgins, Eds., IRL Press, Washington D.C., Chapter 4, pp. 73-111, 1985). The "dot blot" hybridization has been further developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

Another format, the so-called "sandwich" hybridization, involves attaching oligonucleotide probes covalently to a solid support and using them to capture and detect multiple nucleic acid targets. (M. Ranki et al., Gene, 21, pp. 77-85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R, B. Wallace et al. 6 Nucleic Acid Res. 11, p. 3543, 1979; and B. J. Connor et al., 80 Proc. Natl. Acad. Sci, USA pp. 278-282, 1983). Multiplex versions of these formats are called "reverse dot blots".

In another approach of matrix hybridization, Beattie et al., in The 1992 San Diego Conference; Genetic Recognition, November, 1992, used a microrobotic system to deposit micro-droplets containing specific DNA sequences into individual microfabricated sample wells on a glass substrate. The hybridization in each sample well is detected by interrogating miniature electrode test fixtures, which surround each individual microwell with an alternating current (AC) electric field.

One preferred aspect of the present invention is that it results in high-throughput screening capabilities. In the assays described herein, from a few up to millions of different tags identifying, e.g., SNPs, can be identified simultaneously. For example, using simple dot-blot hybridization methods, membranes with thousands of immobilized probes can be generated for screening against tags. The solid-phase techniques described below can be adapted to having literally millions of different immobilized nucleic acids per square inch. Similarly, very large sets of amplified DNAs, e.g., tags, can be immobilized on membranes for simultaneous screening against one or more sequence.

In one embodiment, the identity of the amplification products are determined by detecting the molecular weights of the amplification product or a fragment thereof, such as by chromatography or mass spectroscopy.

For instance, the gross molecular weight of an amplification product or a discrete fragment thereof can be detected. As set forth above, each member of a probe library (i.e., all of the probes in the reaction) has a unique molecular weight label based on the particular sequence of the tag. For instance, mass spectrometry can provide high detection sensitivity and accuracy of mass measurements that can discern between probes which, while identical in length, differ in sequence by only base. Thus, complex libraries can be constructed by calculating the overall molecular weight of each amplification product to be detected by varying the G/C/A/T content in the tag sequence. In certain preferred embodiments, the nucleic acid sequence which is being detected includes, as its only variable sequence, the tag sequence and not the template homology regions. Such fragments can be generated, for example, by including restriction sites that flank the tag sequence, or choosing the PCR primers such that only the tag sequence is the only variable region of the covalently closed circular product which is included in the amplification products. That being said, in those embodiments where the amplification product which is being detected also includes the template homology region(s), the calculation and design of the tag sequences will need to include the variability in the THRs as well in order to produce products having a unique molecular weight so as to be discernable from one another by mass spectroscopy or other detection means as may be chosen.

Those skilled in the art will recognize that very simple algorithms can be used to calculate the molecular weights for each member of a library by varying the sequence of the tag, taking into account if necessary the sequences of the template homology regions. The molecular weight complexity of the tag can be increased by allowing the probes to vary in length as well sequence.

In certain instances, the library can be deconvoluted by chromatographic techniques prior to detection by mass spectroscopy. For example, prior to introducing a sample into the spectrometer, the mixture can first be at least semi-purified. Separation procedures based on size (e.g. gel-filtration), solubility (e.g. isoelectric precipitation) or electric charge (e.g. electrophoresis, isoelectric focusing, ion exchange chromatography) may be used to separate a mixture of amplimers. A preferred separation procedure is high performance liquid chromatography (HPLC).

In certain embodiments, the amplification product can include an integrated mass label for multiplex sequencing. Multiplexing by mass modification in this case is obtained by mass-modifying the nucleic acid primer, e.g., at the level of the sugar or base moiety. Such embodiments are most practical when amplification products are to be mixed for detection after the amplification step rather than before.

Suitable mass spectrometry techniques for use in the present invention include DNA analyses of the present invention include collision-induced dissociation (CID) fragmentation analysis (e.g., CID in conjunction with a MS/MS configuration, see Schram, K. (1990) "Mass Spectrometry of Nucleic Acid Components," in Biomedical Applications of Mass Spectrometry 34:203-287; and Crain P. (1990) Mass Spectrometry Reviews 9:505-554); fast atomic bombardment (FAB mass spectrometry) and plasma desorption (PD mass spectrometry), see Koster et al. (1987) Biomedical Environmental Mass Spectrometry 14:111-116; and electrospray/ionspray (ES) and matrix-assisted laser desorption/ionization (MALDI) mass spectrometry (see Fenn et al. (1984) J. Phys. Chem. 88:4451-4459, Smith et al. (1990) Anal. Chem. 62:882-889, and Ardrey, B. (1992) Spectroscopy Europe 4:10-18). MALDI mass spectrometry is particularly well suited to such analyses when a time-of-flight (TOF) configuration is used as a mass analyzer (MALDI-TOF). See International Publication No. WO 97/33000, published Sep. 12, 1997, see also Huth-Fehre et al. (1992) Rapid Communications in Mass Spectrometry 6:209-213, and Williams et al. (1990) Rapid Communications in Mass Spectrometry 4:348-351.

Suitable mass spectrometry techniques for use in the mass tag analyses of the present invention include collision-induced dissociation (CID) fragmentation analysis (e.g., CID in conjunction with a MS/MS configuration, see Schram, K. (1990) "Mass Spectrometry of Nucleic Acid Components," in Biomedical Applications of Mass Spectrometry 34:203-287; and Crain P. (1990) Mass Spectrometry Reviews 9:505-554); fast atomic bombardment (FAB mass spectrometry) and plasma desorption (PD mass spectrometry), see Koster et al. (1987 Biomedical Environmental Mass Spectrometry 14:111-116; and electrospray/ionspray (ES) and matrix-assisted laser desorption/ionization (MALDI) mass spectrometry (see Fenn et al. (1984) J. Phys. Chem. 88:4451-4459, Smith et al. (1990) Anal. Chem. 62:882-889, and Ardrey, B. (1992) Spectroscopy Europe 4:10-18). MALDI mass spectrometry is particularly well suited to such analyses when a time-of-flight (TOF) configuration is used as a mass analyzer (MALDI-TOF). See International Publication No. WO 97/33000, published Sep. 12, 1997, see also Huth-Fehre et al. (1992) Rapid Communications in Mass Spectrometry 6:209-213, and Williams et al. (1990) Rapid Communications in Mass Spectrometry 4:348-351.

In this regard, a number of mass tags suitable for use with nucleic acids are known (see U.S. Pat. No. 5,003,059 to Brennan and U.S. Pat. No. 5,547,835 to Koster), including mass tags which are cleavable from the nucleic acid (see International Publication No. WO 97/27331).

In still another embodiment, the various tag sequences can be concatenated and sequenced by traditional sequencing techniques, e.g., Sanger or Maxim-Gilbert techniques. To further illustrate, the amplification products can be generated to include restriction sites that flank the tag sequence. Thus, the amplification product can be represented by the formula linker-TAG-linker. After treatment of the amplification products with the restriction enzymes, linker-TAG-linker fragments are ligated to form concatenated nucleic molecules. For example, 5' and 3' linkers can carry a BamH1 and BglII site, respectively, so as to produce compatible sticky ends. In the illustrated example, by carrying out the ligation in the presence of BamH1 and BglII, the resulting concatemer will result in the restriction fragments being linked in a head-to-tail format by virtue of the redigestion of BamHI/BamHI and BglII/BglII ligation products but not of the BamHI/BglII ligation products (which do not produce a sequence recognized by either restriction enzyme).

The concatamer arrays can be isolated, preferably as 2-3 kb fragments, and ligated into an amplification vector. The amplified arrays can then be readily sequenced, with the junction site of restriction enzymes marking the boundaries of one tag sequence from the next.

In another embodiment, the hybridization tags are detected on a micro-formatted multiplex or matrix devices (e.g., DNA chips) (see M. Barinaga, 253 Science, pp. 1489, 1991; W.

Balm, 10 Bio/Technology, pp. 757-758, 1992). These methods usually attach specific DNA sequences to very small specific areas of a solid support, such as micro-wells of a DNA chip. In one variant, the invention is adapted to solid phase arrays for the rapid and specific detection of multiple polymorphic nucleotides, e.g., SNPs. Typically, an oligonucleotide is linked to a solid support and a tag nucleic acid is hybridized to the oligonucleotide. Either the oligonucleotide, or the tag, or both, can be labeled, typically with a fluorophore. Where the tag is labeled, hybridization is detected by detecting bound fluorescence. Where the oligonucleotide is labeled, hybridization is typically detected by quenching of the label. Where both the oligonucleotide and the tag are labeled, detection of hybridization is typically performed by monitoring a color shift resulting from proximity of the two bound labels. A variety of labeling strategies, labels, and the like, particularly for fluorescent based applications are described, supra.

In one embodiment, an array of oligonucleotides are synthesized on a solid support. Exemplar solid supports include glass, plastics, polymers, metals, metalloids, ceramics, organics, etc. Using chip masking technologies and photoprotective chemistry it is possible to generate ordered arrays of nucleic acid probes. These arrays, which are known, e.g., as "DNA chips," or as very large scale immobilized polymer arrays ("VLSIPS TM" arrays) can include millions of defined probe regions on a substrate having an area of about 1 cm2 to several cm2, thereby incorporating sets of from a few to millions of probes.

The construction and use of solid phase nucleic acid arrays to detect target nucleic acids is well described in the literature. See, Fodor et al. (1991) Science, 251: 767-777; Sheldon et al. (1993) Clinical Chemistry 39(4): 718-719; Kozal et al. (1996) Nature Medicine 2(7): 753-759 and Hubbell U.S. Pat. No. 5,571,639. See also, Pinkel et al. PCT/US95/16155 (WO 96/17958). In brief, a combinatorial strategy allows for the synthesis of arrays containing a large number of probes using a minimal number of synthetic steps. For instance, it is possible to synthesize and attach all possible DNA 8 mer oligonucleotides (48, or 65,536 possible combinations) using only 32 chemical synthetic steps. In general, VLSIPS™ procedures provide a method of producing 4n different oligonucleotide probes on an array using only 4n synthetic steps.

Light-directed combinatorial synthesis of oligonucleotide arrays on a glass surface is performed with automated phosphoramidite chemistry and chip masking techniques similar to photoresist technologies in the computer chip industry. Typically, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface.

A 96 well automated multiplex oligonucleotide synthesizer (A.M.O.S.) has also been developed and is capable of making thousands of oligonucleotides (Lashkari et al. (1995) PNAS 93; 7912). Existing light-directed synthesis technology can generate high-density arrays containing over 65,000 oligonucleotides (Lipshutz et al. (1995) BioTech. 19: 442.

Combinatorial synthesis of different oligonucleotide analogues at different locations on the array is determined by the pattern of illumination during synthesis and the order of addition of coupling reagents. Monitoring of hybridization of target nucleic acids to the array is typically performed with fluorescence microscopes or laser scanning microscopes. In addition to being able to design, build and use probe arrays using available techniques, one of skill is also able to order custom-made arrays and array-reading devices from manufacturers specializing in array manufacture. For example, Affymetrix Corp., in Santa Clara, Calif. manufactures DNA VLSIP™ arrays.

It will be appreciated that oligonucleotide design is influenced by the intended application. For example, where several oligonucleotide-tag interactions are to be detected in a single assay, e.g., on a single DNA chip, it is desirable to have similar melting temperatures for all of the probes. Accordingly, the length of the probes are adjusted so that the melting temperatures for all of the probes on the array are closely similar (it will be appreciated that different lengths for different probes may be needed to achieve a particular T[m] where different probes have different GC contents). Although melting temperature is a primary consideration in probe design, other factors are optionally used to further adjust probe construction, such as selecting against primer self-complementarity and the like. The "active" nature of the devices provide independent electronic control over all aspects of the hybridization reaction (or any other affinity reaction) occurring at each specific microlocation. These devices provide a new mechanism for affecting hybridization reactions which is called electronic stringency control (ESC). For DNA hybridization reactions which require different stringency conditions, ESC overcomes the inherent limitation of conventional array technologies. The active devices of this invention can electronically produce "different stringency conditions" at each microlocation. Thus, all hybridizations can be carried out optimally in the same bulk solution. These arrays are described in U.S. Pat. No. 5,051,380 by Sosnowski et al.

Accordingly, the present invention provides array compositions comprising at least a first substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (Affymetrix GeneChip™), spotting techniques (Synteni and others), printing techniques (Hewlett Packard and Rosetta), electrode arrays, three dimensional "gel pad" arrays, etc. Liquid arrays may also be used.

As those in the art will appreciate, the size of the array will vary. Arrays containing from about 2 different capture probes to many millions can be made, with very large arrays being possible. Preferred arrays generally range from about 100 different capture probes to about 100,000, with array densities varying accordingly.

In general, the arrays comprise a substrate with associated capture probes. By "substrate" or "solid support" or other grammatical equivalents herein is meant any material that can be modified to contain discrete individual sites appropriate for the attachment or association of capture probes and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Methods of adding, washing and detecting the amplicons on the array are well known.

Thus, the compositions of the present invention may be used in a variety of research, clinical, quality control, or field testing settings.

In a preferred embodiment, the present invention finds use in the quantification of PCR reactions. Thus, the invention provides a method for quantifying the number of one or more specific sequences in a sample of nucleic acids. The method may be similar to any of the methods described above, so long as the product being detected is present in proportions that are directly correlated with the amount of original template sequence. This is the case, e.g., where the method involves a hybridization step to the template DNA, circularization of the probe, extension of the primers and detection of the extension product. In a preferred embodiment, the method further comprises an amplification step, wherein the amplification reaction is a controlled amplification. This is the case, e.g., when using PCR amplification and stopping the PCR reaction during the exponential phase. The amount of amplified product in this situation will be directly proportional to the amount of original sequence in the nucleic acid sample. Thus, in a preferred embodiment, several amplification reactions are conducted in parallel, using a different number of amplification cycles in each of them. This will assure that at least one of the reactions will have been stopped in the exponential phase.

In methods for quantifying the number of a specific sequence in a sample, it may also be desirable in certain situations to include a marker nucleic acid. The marker nucleic acid can be added to the reaction during the hybridization stage or at any stage thereafter and be subject or not to the same reactions. Alternatively, the marker DNA is used merely to determine the amount of amplified product at the end of the amplification step.

The methods for genotyping and those for quantifying can be used simultaneously, so long as the processes are controlled, such that the amount of amplified product is directly correlated to the amount of the original sequence in the sample nucleic acid.

Nucleic acid variations (i.e., genetic variations) to be detected according to the method of the invention include variations in one or more consecutive or non-consecutive nucleotides in a nucleic acid sample. These variations may be present on a single nucleic acid molecule, e.g., a chromosome, or on several nucleic acid molecules. The invention is particularly applicable for determining the identity of alleles of variable genomic regions (also referred to herein as "allelic variants of a polymorphic region"), e.g., polymorphic regions, is situations in which it has previously been established that different individuals may have one of several possible alleles (as opposed to discovering a new variable region). Generally, the methods of the invention can detect nucleotide insertions, deletions, substitutions, chromosomal translocations and other genetic lesions or variations.

Exemplary variable regions include SNPs. Certain SNPs have two alleles, others have three alleles and yet others have four alleles. The presence of SNPs may be indicative of, for example, a certain population, a disease state, pr a propensity for a disease state.

Other variable regions include more than one nucleotides, and may be polymorphic regions, simple sequence repeats (SSRs), short tandem repeats (STRs), and microsatellite repeats (MRs).

In another embodiment, the methods of the invention permit the detection and identification of microorganisms, e.g., pathogens infecting mammals. Thus, the invention can be used, e.g., to identify the particular strain of a virus that is infecting a human subject, e.g., the particular strain of human immunodeficiency virus, or papilloma virus (HPV), among others. Strains of microorganisms often differ from each other in a few nucleotides, whereas the remaining of their genomes is identical. Thus, probes can be made to recognize the conserved regions and to identify the particular variable nucleotide(s).

For example, a wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes.*

Fungal infectious agents which can be detected by the present invention include *Cryptococcus neoformans, Blastomyces dermatitidis, Histoplasma capsulatum, Coccidloides immitis, Paracoccidioldes brasiliensis, Candida albicans, Aspergillus fumigautus, Phycomycetes* (*Rhizopus*), *Sporothrix schenckii, Chromomycosis*, and *Maduromycosis.*

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovate, Onchoverva volvulus, Leishmania, Trypanosoma* spp., *Schistosoma* spp., *Entamoeba histolytica, Cryptosporidum, Glardia* spp., *Trichimonas* spp., *Balatidium coil, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis.*

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections and in animal breeding programs.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Distinction of Two Templates Differing by a Single Nucleotide

This example demonstrates that it is possible to distinguish two nucleic acids which differ by a single nucleotide by a method in which an oligonucleotide probe is hybridized to the nucleic acid prior to PCR amplification.

Eight reactions were conducted in parallel in which one of two template DNAs, differing from each other by a single nucleotide (referred to herein as "SNP"), were incubated with or without one of two oligonucleotide probes. The different combinations are set forth in Table 1. The template DNA S7 is 600 by long double stranded DNA amplified from *S. cerevisiae* strain S2880, which includes the nucleotide sequence 5' ATCTCGGGATATCAGACTTAGCGGCAC-CGTCCTCACCG 3'(SEQ ID NO: 10): 1 and template DNA Y7 is 600 by long double stranded DNA from *S. cerevisiae* strain YJM789, which includes the nucleotide sequence 5' ATCTCGGGATATCAGACTTAGCGGTAC-CGTCCTCACCG 3'(SEQ ID NO: 11). The two template DNAs are identical except in the underlined nucleotide. The oligonucleotide probe "S" (also referred to as Y2:L: S288C) has the nucleotide sequence 5'CCGCTAAGTCTGATATC-CCGAGAT/GTCCACGAGGTCTCTAGTC/GACCTG-CAGCGTACG/CGG ACCTCAAGTGAAGTACA/CGGT-GAGGACGGT/G 3' (SEQ ID NO: 12); and the oligonucleotide probe "Y" (also referred to as Y21: yjm789) has the nucleotide sequence 5'CCGCTAAGTCTGATATC-CCGAGAT/GTCCACGAGGTCTCTAGTC/GACCTG-CAGCGTACG/CGG ACCTCAAGTGAAGTACA/CGGT-GAGGACGGT/A 3' (SEQ ID NO: 13). The "/" in the probe sequences indicate the different parts of the probe: homology 1/primer 1/primer 2/barcode/homology 2/SNP. The oligonucleotide probe Y is identical to probe S, except that the 3' most base is complementary to the SNP nucleotide in template DNA Y7,

TABLE 1

| Contents of the different reactions | | | | | | | | |
|---|---|---|---|---|---|---|---|---|
| | Reaction | | | | | | | |
| | 1 | 2 | 3 | 4 | 5 | 6 | 7 | 8 |
| Probe | S | Y | none | S | Y | none | S | Y |
| Template | S7 | S7 | S7 | Y7 | Y7 | Y7 | none | none |

A ligase mix was prepared by combining (per reaction): 8 ul of 5×Tth ligase buffer (from Marsh Biomedical, Rochester, N.Y.); 0.32 ul of Tth ligase (from Marsh Biomedical, Rochester, N.Y.) and 29.7 ul of water. To the 38 ul of ligase mix, 1 ul of template DNA at 10 pmol/ul was added. The reaction was incubated for 60 minutes at 55° C. to hybridize the template DNA and the probe and to ligate the 3' and 5' ends of the oligonucleotide probe. To 12.5 ul of this reaction was then added 37.5 ul of PCR mix, prepared by mixing (per reaction) 5 ul of 10×Taq Gold buffer (from PE Biosystems, Foster City, Calif.); 6 ul dNTPs at 1.25 mM; 0.2 ul of AmpliTaq Gold DNA Polymerase at 5 u/ul (from PE Biosystems, Foster City, Calif.) 1 ul of primer p1BAR at 10 pmol/ul; 1 ul of primer P2 at 10 pmol/ul; and 24.3 ul of water. The primer p1 Bar has the nucleotide sequence 5' GACTAGAGACCTCGTGGAC 3' (SEC) ID NO: 1) and the primer P2 has the nucleotide sequence 5' GACCTGCAGCGTACG 3' (SEQ ID NO: 2). The reactions were then incubated for 10 minutes at 95° C. to denature the template DNA, followed by 14 cycles of 95° C. for 20 seconds; 57° C. (decreasing by 0.5 degrees each cycle) for 1 minute; followed by 16 cycles of 95° C. for 20 seconds; 50° C. for 45 seconds; followed by incubation at 4° C.

20 ul of each of the amplification products were then subjected to electrophoresis on a 2% weight/volume agarose gel, and the amplification products were visualized by ethidium bromide staining and U.V. light. The results indicate the presence of a band of about 100 nucleotides in the lanes containing the reaction products in which the probe contains the complementary SNP nucleotide to that present in the template DNA, but not in the other lanes. Thus, probe S identifies the SNP on the template DNA S7 and probe Y identifies the SNP on the template DNA Y7. No product is amplified from a reaction mixture containing template DNA S7 and probe Y or template DNA Y7 and probe S.

Thus, this example demonstrates the identification of a SNP using a method involving hybridization, ligation and then PCR amplification.

Example 2

Identification of a SNP by "Gap Filling"

This example describes a method for determining the identity of a nucleotide, e.g., a SNP, comprising adding an oligonucleotide probe in four reactions containing a polymerase, a ligase, and one of the four nucleotides.

Four different SNPs were tested in singleplex reactions. Sixteen reactions were conducted in parallel, in which each of four DNA templates were incubated with one of four probes. In this example, the template DNAs were from 36 to 42 base oligonucleotides from *S. cerevisiae*. The different combinations are set forth in Table 2. The nucleotide sequences of the templates and probes are as follows (the structure of the probes is indicated as; homology 1/primer 1/primer 2/barcode/(+/−DraI)/homology 2):

```
Template DNA Y1:TOS:T:
                                        (SEQ ID NO: 14)
5' ACATTTAGATCTGCAGTTTCTAATATGAATTCAGTGGAAAAT 3';

Template DNA Y2:TO S:C:
                                        (SEQ ID NO: 15)
5' TCGGGATATCAGACTTAGCGGCACCGTCCTCACCGT 3';

Template DNA Y3:TO S:A:
                                        (SEQ ID NO: 16)
5' GATCAAATGCGACCATATTCATCAAACTTATAGGCG 3';

Template DNA Y5:TO S:G:
                                        (SEQ ID NO: 17)
5' CCAGTCCCTTGAGTTCGCGAATAGTAATTTTGGTGATACCTG 3';
```

-continued

```
Probe Y1:PL:119:31 (also referred to as SNP1):
                                        (SEQ ID NO: 18)
5'GAAACTGCAGATCTAAATGTACC/UGTCCACGAGGTCTCTAGTC/TG
TAAAACGACGGCCAGTU/GCTGGAGTTCGCACGCTATA/ATTTTCCACT
GAATTCATATT 3';

Probe Y2:PL:C:119:55 (also referred to as SNP2):
                                        (SEQ ID NO: 19)
5'CCGCTAAGTCTGATATCCCGAGAT/UGTCCACGAGGTCTCTAGTC/TG
TAAAACGACGGCCAGTU/CAAAGGTGGAGCTGCACACT/TTTAAA/ACGG
TGAGGACGGT 3';

Probe Y3:PL:C:119:131(also referred to as SNP3):
                                        (SEQ ID NO: 20)
5'ATGGTCGCATTTGATCGAG/UGTCCACGAGGTCTCTAGTC/TGTAAAA
CGACGGCCAGTU/GCCTGGGTTACGTGTCTACT/TTTAAA/CGCCTATAA
GTTTGATGAA 3';
and

Probe Y5:PL:119:167(also referred to as SNP5):
                                        (SEQ ID NO: 21)
5'GCGAACTCAAGGGACTGGTAC/UGTCCACGAGGTCTCTAGTC/TGTAA
AACGACGGCCAGTU/GCAATATGTAACTCTCTGGG/CAGGTATCACCAAA
ATTACTATT 3'.
```

TABLE 2

Contents of the different reactions

| | Reaction 1 | 2 | 3 | 4 | 5 | 6 | 7 | 8 |
|---|---|---|---|---|---|---|---|---|
| Probe | Y1:PL 119:31 | Y1:PL 119:31 | Y1:PL 119:31 | Y1:PL 119:31 | Y2:PL:C 119:55 | Y2:PL:C 119:55 | Y2:PL:C 119:55 | Y2:PL:C 119:55 |
| Template | Y1:TO S:T | Y1:TO S:T | Y1:TO S:T | Y1:TO S:T | Y2:TO S:C | Y2:TO S:C | Y2:TO S:C | Y2:TO S:C |
| dNTP | dATP | dCTP | dGTP | dTTP | dATP | dCTP | dGTP | dTTP |

| | Reaction 9 | 10 | 11 | 12 | 13 | 14 | 15 | 16 |
|---|---|---|---|---|---|---|---|---|
| Probe | Y3:PL 119:131 | Y3:PL 119:131 | Y3:PL 119:131 | Y3:PL 119:131 | Y5:PL: 119:167 | Y5:PL: 119:167 | Y5:PL: 119:167 | Y5:PL: 119:167 |
| Template | Y3:TO S:A | Y3:TO S:A | Y3:TO S:A | Y3:TO S:A | Y5:TO S:G | Y5:TO S:G | Y5:TO S:G | Y5:TO S:G |
| dNTP | dATP | dCTP | dGTP | dTTP | dATP | dCTP | dGTP | dTTP |

A DNA mix was prepared by mixing (per reaction) 2 ul of pfu ligase buffer (from Stratagene, San Diego, Calif.); 0.1 mul of template oligonucleotide at 400 fmoles/ul; 0.4 ul of probe oligo (also referred to as "barcode oligo") at 10 pmoles/ul; and 17.5 ul of water. The DNA was denatured by incubating these reactions at 95° C. for 5 minutes. The nucleic acids were then annealed by incubating the reactions at 65° C. for one hour. The final template amount was 40 femtomoles/reaction, and that of the probe oligonucleotide was 4 picomoles/reaction. To each reaction, 20 ul of prewarmed (1 minute at 65° C.) polymerase/ligase/dNTP mix was added. This mix was prepared by combining (per reaction) 2 ul of 10×pfu ligase buffer (from Stratagene, San Diego, Calif.); 2 ul of one dNTP at 1 mM; 0.05 ul. of Taq DNA Polymerase Stoffel fragment (from PE Biosystems, Foster City, Calif.) at 10 u/ul; 1 ul of pfu Ligase (from, Stratagene, San Diego, Calif.) at 4 u/ul; and 14.95 ul of water. The 40 ul reactions were incubated at 65° C. for 10 minutes.

The template DNA was then subjected to rolling circle amplification as follows, 4 ul of the above reactions was added to 32 ul of RCA mix prewarmed at 65° C. for 10 minutes. RCA mix was prepared by combining (per reaction)

4 ul of 10× Vent buffer (from New England Biolabs, Beverly, Mass.); 2 ul of DMSO; 6.4 ul of Vent DNA pol. Exo− at 2 u/ul (NEB); 0.36 ul of RCA primer at 100 pmole/ul; 0.93 ul of T4 gene 32 Protein at 1.7 mg/ml (USB); 0.4 ml of $MgSO_4$ at 100 mM; and 17.91 ul of water. The nucleotide sequence of the RCA primer contains at its 5' end the complement of a portion of the sequence of primer 2, followed by the sequence of primer 1 and has the nucleotide sequence 5' GTCGTTTTACAGACTAGAGACCTCGTGGAC 3' (SEQ ID NO: 22). The reactions were then incubated at 92° C. for 3 minutes (heat denaturation), following which, 4 ul of prewarmed dNTP mix containing 4 mM of all four nucleotides was added, and the reactions were further incubated at 65.5° C. for 4.5 hours. This amplification results in the synthesis of a long strand having at its 5' end the RCA primer, followed by the rest of primer 2-primer 1-HR1-HR2-tag-primer 2-[primer 1-HR1-HR2-tag-primer 2-]n.

For the PCR amplification step, two reactions were done for each of the template/probe combinations by combining 1 ul of each of the above reactions with 19 ul of PCR mix containing (per reaction) 2 ul of 10×Taq Gold buffer (from PE Biosystems, Foster City, Calif.); 0.75 ul of dNTPs at 4.0 mM; 0.15 ul of AmpliTaq gold DNA Polymerase at 5 u/ul (PE); 0.16 ul of P1bar primer (SEQ ID NO: 1) at 100 pmol/ul; 0.16 ul of M13 primer (i.e., primer 2) at 100 pmol/ul; 2 ul of $MgCl_2$ at 25 mM; and 13.78 ul of water. The nucleotide sequence of the M13 primer is 5' TGTAAAACGACGGCCAGT 3'(SEQ ID NO: 3). The PCR reactions were denatured for 5 minutes at 95° C. and then subjected to either 15 or 25 cycles of 20 seconds at 95° C. and 1 minute at 50° C.

20 ul of each of the reactions were then subjected to gel electrophoresis in 2% agarose, and the products visualized as described in Example 1. The results indicate that in one of each of the four reactions containing a different dNTP each, amplification product is obtained with the dNTP that is complementary to the SNP in the DNA. For example, more amplification product was detected in the reaction in which dATP was added to the probe containing a thymidine as SNP nucleotide, compared to the reactions in which dCTP, dGTP or dTTP was added.

Thus, this example demonstrates a method for identifying a nucleotide in a nucleic acid, comprising hybridization of a probe to the nucleic acid, gap filling by the addition of a specific dNTP through polymerization and ligation, extension of a primer, ligation, PCR amplification; and detection of amplified product(s).

Example 3

Background Suppression by Capture of the Run-Off Products Using Biotin-Streptavidin This experiment is a demonstration of a biotin capture cleanup method used to suppress background that arises from elongation events that are primed by unligated oligo probe during PCR amplification. A biotinylated primer is used to make a first copy of the ligated probe. This copy is captured with streptavidin coated magnetic beads while all other molecules are washed away. The captured copy is then amplified in a PCR reaction.

The template DNAs and probes were identical to those used in Example 1: The two template DNAs used were the 600 by amplicons designated S7 and Y7, comprising SEQ ID NO: 10 and 11, respectively, which differ from each other in as single, nucleotide; and the two probes S and Y, having SEQ ID NO: 12 and 13, respectively.

The different combinations of template and probes are set forth in Table 3.

TABLE 3

Components of the reaction mixtures

| | Reaction 1 | 2 | 3 | 4 | 5 | 6 | 7 | 8 |
|---|---|---|---|---|---|---|---|---|
| Probe | S allele | S allele | S allele | S allele | Y allele | Y allele | Y allele | Y allele |
| Template | Y7 | S7 | S7 | none | Y7 | Y7 | S7 | none |
| other | | | No ligase | | | No ligase | | |

Two barcode oligo mixes were prepared (one for each barcode oligo) by mixing 20 ul of 5×Tth ligase buffer, 15 ul of barcode oligonucleotide S or Y at 10 pmoles/ul; and 62.5 ul of water, and 19.5 ul of this mix was added to 8 strip tubes. To each strip tube, 0.5 ul of respective PCR template S7 or Y7 at 0.04 ug/ul was added. The final barcode and template amount was 30 picomoles and 40 femtomoles per reaction, respectively.

21.5 ul of ligase mix that was prepared by mixing 36 ul of 5×Tth ligase buffer and 135 ul of water, was added to strip tubes 3 and 6 (reactions without ligase). 3.5 ul of Tth ligase (50 u/ul Marsch Bio.) was added to the remaining ligase mix and 21 ul of this mix were added to the remaining tubes. The tubes were heated for 1 minute at 65° C., and 20 ul of each tube was added to each of the strip tubes containing the DNAs. The volume of each reaction was 40 ul.

Biotinylated P1Bar primer is identical to P1bar primer (SEQ ID NO:1) except that it was synthesized with a 5' biotin.

For rolling amplification, an extension mix (RCA mix) was prepared by combining (for 20 reactions) 40 ul of 10× vent buffer; 20 ul DMSO; 64 ul of Vent DNA Polymerase exo− at 2 u/ul (NEB); 3.6 ul of P1bar biotin primer (SEQ ID NO: 1) at 100 pmol/ul; 9.3 ul of T4 gene 32 protein 1.7 m/ml; 4 ul of $MgSO_4$ at 100 mM; 40 ul of each of the four dNTPs at 4 mM; and 179.2 ul of water to obtain a final volume of 360 ul. 18 ul of RCA mix that was prewarmed for 1 minute at 65° C., was added to 2 ul of the above reactions, and incubated for 2.5 minutes at 65° C. This results in having 8 tubes each with Taq and Vent elongated biotin P1bar primer.

The biotinylated run-off product was isolated using stock Dynabeads (10 ug/ul). These beads can capture up to 20 pmole of biotinylated oligo using 10 ul of stock, 20 ul out of the 40 ul were taken from each reaction tube and captured with Dynal beads as follows: the stock beads were first washed thrice with 2M NaCl Buffer (use same volume of buffer as sample); equal volumes of sample and washed beads were combined to obtain a final 1M NaCl mix; this mix was centrifuged at 43° C. for 15 minutes at 1400 rpm; the beads were washed twice with 100 ul of 2M NaCl buffer and then, once with 100 ul double distilled water (by gentle tapping instead, not by pipetting); the beads were resuspended in 50 ul of 50 mM NaOH and incubated at room temperature for 5 minutes; the supernatant (which may be neutralized with 5 ul of 0.5M HCl) was removed; and the beads were resuspended in original sample volume (eg. 20 ul) using 1×TE.

A PCR mix was prepared by mixing 48 ul of 10×Taq Gold buffer; 18 ul of dNTPs at 4.0 mM; 3.84 ul of P1Bar primer (SEQ ID NO; 1) at 100 pmol/ul; 3.84 ul of M13 primer (SEQ ID NO: 3) at 100 pmol/ul; 48 ul of MgCl2 at 25 mM; and 330.7 ul of water to obtain a total of 456 ul. 1.0 ul of bead slurry reaction was added to 19 ul PCR mix; denatured for 5 minutes at 95° C.; and subjected to 30 or 40 cycles of PCR as follows: 20 seconds at 95° C. and 1 minute at 60° C.

20 ul of each reaction was then subjected to electrophoresis in 2% agarose, and the bands were visualized as described in the previous examples. The results indicate that more amplification product was obtained in reactions in which the probe perfectly matches the template DNA and ligase is included, i.e., in reactions 2 and 5. In addition, isolation of the run-off product on beads allows cleaner amplification.

Example 4

Background Suppression by Digestion of the Probe with Uracil-N-Glycosylase Prior to Amplification Another method to suppress background that arises as a result of extension from unligated oligonucleotide probe during PCR is to digest the unligated probe with uracil-N glycosylase prior to PCR amplification. Digestion of the unligated oligonucleotide probe with uracil-N-glycosylase (also referred to as "UNG") breaks the probe into three fragments that can no longer prime the generation of PCR background amplicons.

This example describes a method using comparing uracil-N-glycosylase as a and biotin isolation of run-off product cleanup methods.

The template DNA and probes were the same as those used in Example 3 (note that these oligonucleotides were synthesized with U bases in the indicated locations), and the different combinations were also the same (Table 3). In this example, pfu ligase was used instead of Tth ligase.

Two barcode oligo mixes were prepared (one for each barcode oligo) by mixing 10 ul of 5×Tth ligase buffer, 15 ul of barcode oligonucleotide S (SEQ ID NO: 12) or Y (SEQ ID NO: 13) at 10 pmoles/ul; and 72.5 ul of water. 19.5 ul of this mix was added to 8 strip tubes. To each strip tube, 0.5 ul of respective PCR template 57 or Y7 at 0.40 ug/ul was added. The final barcode and template amount was 30 picomoles and 40 femtomoles per reaction, respectively.

The reaction mixtures (containing the DNAs) were denatured for 5 minutes at 95° C. and annealed for 15 minutes at 65° C. 23.75 ul of ligase mix prepared by combining 24 ul of 10×pfu ligase buffer and 204 ul of water, were added into strip tubes 3 and 6. 10 ul of pfu ligase at 4 u/ul (Stratagene) was added to the remaining mix of 204.25 ul. To each tube (except tubes 3 and 6), 20 ul of ligase mix prewarmed for 1 minute at 65° C. was added, and the reactions were incubated for 10 minutes at 65° C. (ligation reactions). The final reaction volume was 40 ul.

2 ul of ligation reactions were added to 18 ul of extension mix, which was prepared by combining 40 ul of 10×Taq Gold buffer; 15 ul of dNTPs at 4 mM each; 3 ul of AmpliTaq Gold DNA Polymerase at 5 u/ul (P.E.); 3.2 ul biotin RCAP1Bar primer (5' GTCGTTTTACAGACTAGAGACCTCGTGGAC 3' SEQ ID NO: 28) at 100 pmol/ul (same as in example 3); 40 ul of MgCl2 at 25 mM; and 258.8 ul of water to obtain a final volume of 360 ul of PCR reaction mix. The reactions were then incubated for 10 minutes at 95° C. to denature the ligated product as well as to activate Taq Gold. One set of reactions was then incubated for 2 minutes at 65° C., and another set of reactions was The One set of reactions was then incubated for 15 minutes at 65° C. to run-off and another set of reactions was not incubated at 65° C. (no run-off control). This resulted in 2×8 tubes with Taq elongated biotin RCA primer. The RCA biotin primer contains sequence appended to the 5' end of the P1 primer and was used to increase the distance between the priming sequences and the bead in case the bead sterically hindered the PCR reaction.

Two PCR mixes were prepared as described in Example 3 with and without the addition of 1 ul per reaction of uracil-N-glycosylase (PE Biosystems, Foster City, Calif.). 1.0 ul of extension reaction was added to 19 ul PCR mix; denatured for 5 minutes at 95° C.; and subjected to 25 cycles of PCR as follows: 20 seconds at 95° C. and 1 minute at 64° C. Also, as a control, 1 ul of a 1:10 dilution of the ligation reaction (no extension) was added to 19 ul PCR mix, denatured for 5 minutes at 95° C.; and subjected to 25 cycles of PCR as follows: 20 seconds at 95° C. and 1 minute at 64° C.

20 ul of each reaction was then subjected to electrophoresis in 2% agarose, and the bands were visualized as described in the previous examples. The results indicate that, in the no extension controls, all background is eliminated by UNG digestion of the probe (lanes 1, 3, 4, 6, 7, 8). In addition, this control shows that the specific signal (lanes 2 and 5) are also eliminated without the extension step, thus confirming that the original probe is degraded by UNG and that extension is required for signal. The extendedsion experiments indicate that UNG eliminates the background (lanes 1, 3, 4, 6, 7, 8) but not the specific signal (lanes 2 and 5).

Example 5

Background Suppression by Use of Apyrase

Another source of background signal comes from contaminating nucleotides in various reagents such as ligase and template preparations. These contaminating nucleotides generate signal in the polymerase-ligase step even if the added nucleotide is not complementary to the SNP being tested. To eliminate this source of background, apyrase, an enzyme that degrades nucleotides, was added to all reagents at the assembly of the reaction. Contaminating nucleotides were degraded in a 20° C. incubation, prior to the DNA denaturing step. Apyrase was heat inactivated during the denaturing and annealing steps so that the later added specific nucleotide is not degraded.

The different reactions performed are summarized in Table 4.

TABLE 4

| components of the different reactions: | | | | | | | | |
|---|---|---|---|---|---|---|---|---|
| | Reaction | | | | | | | |
| | 1 | 2 | 3 | 4 | 5 | 6 | 7 | 8 |
| probe | SNP 2 | SNP 2 | SNP 2 | SNP 2 | SNP 2 | SNP 2 | SNP 2 | SNP 2 |
| Template | Y7 | Y7 | Y7 | Y7 | S7 | S7 | S7 | S7 |
| dXTP | dATP | dCTP | dGTP | dTTP | dATP | dCTP | dGTP | dTTP |
| Other | Apyrase+ | Apyrase+ | Apyrase+ | Apyrase+ | Apyrase+ | Apyrase+ | Apyrase+ | Apyrase+ |
| | Reaction | | | | | | | |
| | 9 | 10 | 11 | 12 | 13 | 14 | 15 | 16 |
| probe | SNP 2 | SNP 2 | SNP 2 | SNP 2 | SNP 2 | SNP 2 | SNP 2 | SNP 2 |
| Template | S7 | S7 | S7 | S7 | | S7 | S7 | S7 |
| dXTP | dATP | dCTP | dGTP | dTTP | dGTP | dGTP | dTTP | |
| Other | Apyrase− | Apyrase− | Apyrase− | Apyrase− | Apyrase+ Template− | Apyrase+ Pol/lig− | Apyrase+ Pol/lig− | Apyrase+ dXTP− |

Three template/barcode mixes were prepared by mixing in each 6 ul of 10×pfu ampligase buffer; 1.8 ul of barcode oligo (having the sequence set forth in SEQ ID NO: 19); 3 ul of PCR template (either S7 SEQ ID NO 10, Y7 SEQ ID NO 11, or water; these templates are the same as those used in Example 1); and 49.2 ul of water to obtain a final volume of 60 ul. 12 ul of each were distributed into tubes.

12 ul of ligase mix was aliquoted into 16 strip tubes. The mix was prepared for the various reactions as described in Table 5, and the ligase dilution was prepared by mixing 5 ul of 10× ampligase buffer with 44.33 ul of water and 0.67 ul of Ampligase at 5 u/ul, resulting in a solution containing 0.067 u/ul of Ampligase.

TABLE 5

| Preparation of ligase mixes | | | | |
|---|---|---|---|---|
| Ligase mix | each | Rxn 1-8, 13, 16 (×16) | Rxn 9-12 (×8) | Rxn 14 and 15 (×4) |
| 10× ampligase buffer | 1.0 ul | 16.0 ul | 8.0 ul | 4.0 ul |
| Ampligase dilution | 0.125 | 2.0 ul | 1.0 ul | N/A |
| Taq DNA Pol. Stoffel frag 10 u/ul | 0.05 ul | 0.8 ul | 0.4 ul | N/A |
| Apyrase 50 mU/ul | 0.2 ul | 3.2 ul | N/A | 0.8 ul |
| H2O | | 106 ul | 54.6 ul | 27.2 ul |
| Total | 8.0 ul | 128.0 ul | 64.0 ul | 32.0 ul |

The barcode/template mixes were denatured for 5 minutes at 95° C. and annealed for 15 minutes at 65° C. 8 ul ligase mixes were added to the annealed DNA mixes. These were then incubated for 2 min at 20° C. degrees. The barcode/template mixes were then denatured for 5 minutes at 95° C. and annealed for 15 minutes at 65° C. The temperature was raised to 65° C. and 2 ul dXTP (1 mM) were added to the appropriate tubes, following which they were incubated for 10 min at 65° C. Final reaction volume was 20 ul. Final enzyme ligase concentration was 0.00042 units/ul in the ligation reaction (0.0084, units total), the final barcode concentration was 0.015 picomoles/ul and the final template concentration was approximately 2 femtomoles/ul. [Please confirm or infirm this sequence of steps] 2 ul of each ligation reaction were added to 18 ul of PCR extension mix, prepared by combining 85 ul of 4×E/U buffer (4×Taq Gold buffer; 3.2 picomoles per microliter P1bar primer (SEQ ID NO: 1); 10 mM MgCl2; 0.6 mM dNTPs); 2.55 ul of AmpliTaq Gold DNA Polymerase (P.E. Biosystems, Foster City, Calif.) at 5 u/ul and 218.5 ul of water to obtain a final volume of 306 ul. The reactions were incubated for 10 minutes at 95° C. to denature the ligated product as well as to activate Taq Gold. The reactions were then incubated for 2 minutes at 65° C. to run-off.

UNG clean up and amplification were conducted as follows. To each reaction (20 ul), 20 ul of UNG/PCR mix was added. This mix was prepared by combining 85 ul of 4×E/U buffer; 2.55 ul of AmpliTaq Gold DNA Polymerase (P.E.) at 5 u/ul; 17 ul of UNG (1 unit/ul PE Biosystems, Foster City, Calif.); 5.44 ul of M13 primer (SEQ ID NO: 3) at 100 pmol/ul and 230 ul of water to obtain a final volume of 340 ul. The reactions were incubated for 20 minutes at 37° C. and then heat denatured for 5 minutes at 95° C. PCR was conducted for 33 cycles as follows: 20 seconds at 95° C. and 1 minute at 60° C.

The amplification products were analyzed in the same way as in the previous examples. The results indicate that the presence of apyrase in the reactions strongly reduce background amplification. This can be seen, e.g., by comparing the first four lanes 3 and 4, in which the absence of apyrase in a tube containing dCTP (nucleotide that is not complementary to the SNP in the template DNA) results in a band, whereas the presence of apyrase in the same reaction does not produce a band. In comparison, in the first two lanes, representing reactions done with dATP (the nucleotide that is complementary to the SNP in the template DNA), the presence or absence of apyrase does not affect the signal observed, thus showing that the signal is specific, and not resulting from background amplification. Thus, the use of apyrase can reduce background amplification.

Example 6

Detection of Two SNPs in a Single Reaction

This example describes an example of a reaction in which two SNPs were detected simultaneously. The background reduction methods using apyrase; and uracil-N-glycosylase digestion; or and biotin capture of extension products were included.

The combinations of template and probe are were as shown in Table 6. The DNA templates were 600 by DNA fragments amplified from S. cerevisiae. The template S7 (SEQ ID NO: 10 is described in Example 1. Template S37 is a 600 by long double stranded DNA amplified from S. cerevisiae strain S288C, which includes the nucleotide sequence 5'CCAGTC-CCTTGAGTTCGCGAATAGTAATTTTGGTGATACCTG 3'(SEQ ID NO: 179). The barcode oligonucleotides are SNP2 (SEQ ID NO: 19) and SNP5 (SEQ ID NO: 21).

TABLE 6

Components of the reactions

| | Reaction | | | | | | | |
|---|---|---|---|---|---|---|---|---|
| | 1 | 2 | 3 | 4 | 5 | 6 | 7 | 8 |
| probe | SNP 2 | SNP 2 | SNP 5 | SNP 5 | SNP 2 SNP 5 | SNP 2 SNP 5 | SNP 2 SNP 5 | SNP 2 SNP 5 |
| Template | S-7 | S-7 | S-37 | S-37 | S-7 S-37 | S-7 S-37 | S-7 S-37 | S-7 S-37 |
| dXTP | dCTP | dGTP | dCTP | dGTP | dATP | dCTP | dGTP | dTTP |

DNA template/probe reaction mixtures were prepared as set forth in Table 7. The enzyme mix listed in the table was prepared by mixing 154.3 ul water; 22 ul of 10× ampligase buffer; 2.2 ul of Apyrase at 50 mU/ul; 1.38 ul of Ampligase dilution (5 ul of 10× ampligase buffer; 44.33 ul of water and 0.67 ul of Ampligase at 5 u/ul); and 0.55 ul of Taq DNA Pol. Stoffel fragment at 10 u/ul.

TABLE 7

Components of DNA/enzyme mix

| DNA/ Enzyme mix | Mix 1&2 (×2.5) | Mix 3&4 (×2.5) | Mix 5-8 (×5) |
|---|---|---|---|
| Enzyme mix | 41.0 ul | 41.0 ul | 82.0 ul |
| Template S-7 | 1.25 ul (S7) | | 2.5 ul (S7) |
| Template S-37 | | 1.25 ul (S37) | 2.5 ul (S37) |
| SNP2 1 pmol/ul | 0.75 ul (SNP2) | | 1.5 ul (SNP2) |
| SNP5 1 pmol/ul | | 0.75 ul (SNP5) | 1.5 ul (SNP5) |
| Total | 45.0 ul | 45.0 ul | 90.0 ul |

18 ul of the mix were distributed into strip tubes. The potential contaminating nucleotides dXTPs were degraded by incubation of the reactions for 4 minutes at 20° C. The reactions were then heated for 5 minutes at 95° C. and annealed by incubation for 15 minutes at 65° C., 2 ul of the respective dXTPs 0.1 mMset forth in Table 6 were added to the reactions and the reactions were incubated for 10 minutes at 65° C. (ligation reactions). In the ligation reaction (20 ul), the final barcode concentration was 0.015 picomoles/ul and template was approximately 2 femtomoles/ul. Final ligase concentration was 0.00042 units/ul in the ligation reaction (0.0084 units total).

6 ul of ligation reactions were added to 54 ul of extension mix prewarmed for 1 minute at 95° C. The extension mix was prepared by combining 54 ul of 10×Taq Gold buffer; 4.05 ul AmpliTaq Gold DNA Polymerase at 5 u/ul; 64.8 ul of dNTPs at 1.25 mM each; 54 ul of MgCl2 at 25 mM; 4.32 ul of P1BAR (SEQ ID NO 1) biotin primer at 100 pmol/ul; and 101.61 ul of water.

The reactions were incubated 10 minutes at 95° C. to denature the ligated products as well as to activate Taq Gold and then incubated for 2 minutes at 55° C. to 79° C. gradient to runoff. The reactions were then cooled to 4° C.

Three cleanups were performed: UNG cleanup, a low stringency biotin cleanup (3 washes), and an increased stringency biotin cleanup (6 washes). 20 ul of each reaction were subjected to capture on Dynal beads. The stock beads were washed thrice with 2M NaCl Buffer using the same volume of buffer as that of the sample. To 25 ul of beads were added 75 ul 1M NaCl, 20 ul of sample were mixed with 80 ul of beads in NaCl to get final 1M NaCl mix and incubated at 43° C. for 15 min, pipetting up and down every 5 minutes. The beads were then washed 3 or 6 times in 200 ul of 0.5 M NaCl/0.5 M NaOH buffer, followed by a wash with 200 ul of 0.5 M NaCl in TE. The beads were resuspended in 200 ul of: 100 mM NaCl, TE, 0.25% DMSO, 0.01% Triton, and heated for 15-20 min at 70° C. This releases non-specifically bound product to beads. The beads were then washed again with 200 ul TE. The beads were resuspended in original sample volume (eg. 20 ul) using 1×TE.

Amplification of the cleaned up extension product was carried out by mixing 20 ul of the extension product with 20 ul of UNG/PCR mix prepared by combining 18 ul 10×TaqAQ Gold buffer; 1.35 ul AmpliTaq gold DNA polymerase at 5 u/ul; 21.6 ul of dNTPs at 1.25 mM each; 18 ul of MgCl2 at 25 mM; 1.44 ul P1Bar primer (SEQ ID NO: 1 !) at 100 pmol/ul; 1.44 ul M13 primer (SEQ ID NO: 3) at 100 pmol/ul; 9 ul of UNG at 1 unit/ul; and 109.17 ul of water. The reactions were incubated for 20 minutes at 37° C., heat denatured for 5 minutes at 95° C. and subjected to 14 PCR cycles including 20 seconds denaturation at 95° C.; 1 minute annealing at 63° C.; and 10 seconds extension at 72° C.; followed by 20 cycles of 20 seconds at 95° C.; 45 seconds at 56° C. and 10 seconds at 72° C. The reactions were incubated for another 10 seconds at 72° C. and then at 4° C.

The reaction products were analyzed in the same way as in the previous example. The results show that, as expected, a stronger amplification signal was obtained in lanes 2, 3, 6 and 7 (which correspond to reactions including dNTPs that are complementary to the SNP in the template DNA) relative to the other lanes. Since lanes 6 and 7 comprise the two template DNAs and the same two probes and that the reactions were identical except for addition of dCTP in one reaction and dGTP in the other reaction, these results show that two different SNPs can be identified using in the same reaction if the two dNTPs are included in the same reactions.

The amplified products from reactions 6 and 7 were also subjected to a DraI restriction digest, which cleaves between the tag sequence and the homology region THR2s. Because the two different probes have different length homology regions, it is evident it possible to identify which the probe is which was amplified in each reaction on a high resolution gel. Probe 5 consisted of 109 bases, whereas probe 2 consisted of 104 bases.

Accordingly, 1 ul of DraI enzyme was added to 20 ul of PCR product of reactions 6 and 7 and incubated at 37° C. for 1 hour. The results show that, as expected, the amplification product observed in reaction 6 corresponds to probe SNP2, whereas that observed in reaction 7 corresponds to probe SNP7. These results provide further support for multiplexing.

Example 7

Use of a Two Part Probes Instead of a One Part Probe

All probe oligonucleotides described above were synthesized as a single molecule. This example shows the functional use of a two part ligated oligonucleotide probe. These probes ewers made constructed by ligating a 40 base oligonucleotide to a 60 base oligonucleotide using a bridge oligonucleotide that is common to all probes.

The template/probe combinations are set forth in Table 8. The template S37 and the probe SNP5 (SEQ ID NO: 21) were was described in the previous Example. SNP5 was described in Example 2 (SEQ ID NO: 21). SNP5 2 part probe was constructed by ligating part A, comprising the template homology region 1 and primer 1 homology region with part B comprising primer 2 homology region, barcode sequence, DraI and template homology region 2. The two parts were enzymatically ligated with a bridging oligonucleotide having the sequence 5' ACTGGCCGTCGTTTTACA/GACTAGAGACCTCGTGGAC 3' (SEQ ID NO: 226; the "/" indicates the portions that are complementary to part A and part B, respectively. Ligation was carried out as follows: 10 picomoles each of SNP5 part A, SNP5 part B, and the bridging oligonucleotide were incubated with 5 units of ampligase, in 1× ampligase buffer for one hour at 60 degrees C. The probes contain an uracil base between the primer 2 homology region and the barcode sequence.

TABLE 8

| Components of the reactions | | | | | | | | |
|---|---|---|---|---|---|---|---|---|
| | Reaction | | | | | | | |
| | 1 | 2 | 3 | 4 | 5 | 6 | 7 | 8 |
| probe | SNP 5 Syn 3 | SNP 5 Syn 3 | SNP 5 Syn 3 | SNP 5 Syn 3 | SNP 5 2 part | SNP 5 2 part | SNP 5 2 part | SNP 5 2 part |
| Template | S-37 | S-37 | S-37 | S-37 | S-37 | S-37 | S-37 | S-37 |
| dXTP | dATP | dCTP | dGTP | dTTP | dATP | dCTP | dGTP | dTTP |

An enzyme mix was prepared by combining 148.3 ul of water, 20 ul of pfu ampligase buffer; 5 ul of template S37 at 0.04 . . . ug/ul; 2 ul of Apyrase at 50 mU/ul; 1.25 ul Ampligase dilution (5 ul 10× ampligase buffer; 44.33 ul water; and 0.67 ul Ampligase at 5 u/ul); and 0.5 ul Taq DNA Polymerase Stoffel fragment at 10 u/ul. DNA enzyme mixes were prepared by combining 79.7 ul of enzyme mix with 1.35 ul of either probe at 1 pmol/ul. In the ligation reaction (20 ul), the final barcode concentration was 0.015 picomoles/ul, template is approximately 2 femtomoles/ul. Final ligase concentration was 0.00042 units/ul in the ligation reaction (0.0084 units total).

18 ul were aliquoted into strip tubes. The dXTPsPotential contaminating nucleotides were degraded by incubation for 4 minutes at 20° C. The DNA is then denatured by incubation for 5 minutes at 95° C., and annealed by incubation for 15 minutes at 65° C., 2 ul of respective dXTPs at . . . 0.1 mM, . . . was added to the appropriate reactions and incubated for 10 minutes at 65° C. (ligation reactions).

2 ul of ligation reactions were added to 18 ul of extension mix prewarmed at 95° C. Extension mix was prepared by combining 45 ul 4×E/U buffer (described in example 5); 1.35 ul of AmpliTaq gold DNA Polymerase at 5 u/ul and 115.65 ul of water. The reactions were incubated for 10 minutes at 95° C. to denature the ligated product as well as to activate Taq Gold. The reactions were incubated for 2 minutes to runoff, and then brought to 4° C. (extension reaction).

UNG cleanup and amplification was performed by mixing 20 ul of extension reaction with 20 ul of UNG/PCR mix, prepared by mixing 85 ul of 4×E/U buffer; 2.55 ul of AmpliTaq Gold DNA Polymerase at 5 u/ul; 17 ul UNG at 1 unit/ul; 5.44 ul of M13 primer (SEQ ID NO 3) at 100 pmol/ul and 230 ul of water. The reactions were incubated for 20 minutes at 37° C.; denatured for 10 minutes at 95° C.; subjected to 14 PCR cycles of 20 seconds at 95° C., 1 minute at 69.6° C. (decreasing by 0.4 degrees every cycle) and 10 seconds at 72° C.; followed by 20 PCR cycles of 20 seconds at 95° C.; 45 seconds at 64° C.; and 10 seconds at 72° C. The reactions were then incubated for 10 seconds at 72° C. and then soaked at 4° C.

The reaction products were analyzed in the same way as in the previous examples. The results clearly show that amplification was observed only in lanes 2 and 6, both of which contained the dGTP, which is the nucleotide that is complementary to the SNP in the template DNA. In addition, the bands in the two reactions were similar, indicating that 2 part probes are as functional as a one part probe.

Example 8

Detection of a SNP Among in *S. cerevisiae* Genomic DNA

This example describes the detection of a SNP within in *S. cerevisiae* genomic DNA template using the polymerase/ligase method with a two part probe, and Apyrase and UNG for reducing background amplification.

PCR Template DNA used in this example was either *S. cerevisiae* genomic DNA (referred to as genomic template) alone or containing varying concentrations of the template DNA S37 (SEQ ID NO: 179 described in previous examples) was diluted in *S. cerevisiae* genomic DNA (referred to as genomic template). To obtain the different dilutions of S37 genomic DNA, the yeast The probe used in this example was SNP5 (SEQ ID NO 21). Probe DNA was first diluted to 0.3 pmol/ul, from which 4 aliquots of 19 ul were prepared. 1 ul of S37 DNA was added to the first tube, mixed, one ul of this dilution was added into the next tube and so on so that the PCR template 537 is serially diluted by the probegenomic DNA. In reactions 7 and 8, no PCR template is added and only genomic DNA template is present.

The different probe and template DNA combinations are set forth in Table 9,

TABLE 9

| Components of the reactions | | | | | | | | |
|---|---|---|---|---|---|---|---|---|
| | Reaction | | | | | | | |
| | 1 | 2 | 3 | 4 | 5 | 6 | 7 | 8 |
| Probe | SNP5 | SNP5 | SNP5 | SNP5 | SNP5 | SNP5 | SNP5 | SNP5 |
| Template | S37/10 | S37/10 | S37/200 | S37/200 | S37/4000 | S37/4000 | — | — |
| Genomic template | + | + | + | + | + | + | + | + |
| dXTP | C | G | C | G | C | G | C | G |

The reactions were carried out as described in Example 7. Briefly, the template and probe DNAs were combined and incubated with 100 ng of genomic yeast DNA, Apyrase, Ampligase and Taq DNA Polymerase Stoffel fragment for 4 minutes at 20° C. to degrade the dXTPpotential contaminating nucleotides. The reactions were then denatured by incubation at 95° C. and annealed by ramping down to 65° C. over about 30 minutes, and then incubated for 10 minutes at 65° C.

2 ul of each reaction was added to 18 ul of runoff mix prepared by combining (per reaction) 2 ul 10×Taq Gold buffer; 0.75 ul dNTPs at 4 mM each; 0.15 ul of AmpliTaq gold DNA Polymerase at 5 u/ul; 0.16 ul P1bar biotin primer (SEQ ID NO 1) at 100 pmol/ul; 2 ul MgCl2 at 25 mM; and 12.94 ul water. The reactions were heat denatured for 10 minutes at 95° C. and runoff products obtained by incubation for 2 minutes at 60° C. While the reactions were still at 60° C., 20 ul of the reactions were transferred to a UNG/PCR mix prepared by combining 2 ul of 10×Taq Gold buffer; 0.75 ul dNTPs at 1.25 mM each; 0.3 ul AmpliTaq Gold DNA Polymerase at 100 pmol·ul; 1 ul UNG; 0.32 ul M13 primer (SEQ ID NO 3) at 100 pmol/ul; 2 ul MgCl2 at 25 mM; and 13.31 ul water. The reactions were incubated for 20 minutes at 37° C., heat denatured for 5 minutes at 95° C. and subjected to 14 and 30 amplification cycles of 20 seconds at 95° C. and 1 minute at 60° C. each.

The amplification products were analyzed as described above. The results show the presence of an amplified product in each lane containing a reaction with a dCTP (the nucleotide complementary to the SNP in the template DNA), but not in lanes containing a reaction with a dGTP. Thus, identification of the SNP was clear even in template DNA highly diluted with yeast DNA. In addition, a strong band was also seen in lanes 7, which contained only genomic template and no S37 template, but not in lane 8, which contained dGTP. Thus, this example clearly shows that a SNP can be identified in a unique sequence in genomic DNA.

In lanes 7 and 8, with no added PCR template, the only template present is genomic template demonstrating that a SNP can be detected from genomic DNA.

Example 9

Detection of Five SNPs in the Same Reaction

This example demonstrates the identification of five SNPs in template DNA in a single reaction using the ligase/polymerase method, two part probes, and the Apyrase, biotin isolation of extension product, and UNG background reduction methods.

The template DNAs were a mix of 600 base pair PCR templates amplified from *S cerevisiae*; S-7 (SEQ ID NO: 10), 26 containing the sequence 5' ACATTTAGATCTGCAGTTTCTAATATGAATTCAGTGGAAAAT 3'(SEQ ID NO: 238), 30 containing the sequence 5' GATCAAATGCGACCATATTCATCAAACTTATAGGCG 3' (SEQ ID NO: 167 and 37 containing both sequences 5' TACTGTACCCATTTTTTTGTCGCTTAAGGTTTCGCGT 3' (SEQ ID NO: 5) and SEQ ID NO: 17 $(S37)_9$. The probes used were SNPs1, 2, 3, and 5 described previously, e.g., in Example 2. SNP4 (Y4:PL:C:119:159) has the nucleotide sequence 5'ACAAAAAAATGGGTACAGTATAA/UGTCCACGAGGTCTCTAGTC/TTGTAAAACGACGGCCAGT/UGGTAGTACGGTGCTCTTACACTTTAAA/ACGCGAAACCTTAAG 3' (SEQ ID NO: 23; representing homology 1/primer1/primer 2/barcode/DraI/homology2; U is uracil). The different combinations of template DNA and probes is set forth in Table 10.

TABLE 10

| Components of each reaction | | | | | | | | |
|---|---|---|---|---|---|---|---|---|
| | Reaction | | | | | | | |
| | 1 | 2 | 3 | 4 | 5 | 6 | 7 | 8 |
| probe | SNPs 1, 2, 3, 4, 5 | SNPs 1, 2, 3, 4, 5 | SNPs 1, 2, 3, 4, 5 | SNPs 1, 2, 3, 4, 5 | SNPs 1, 2, 3, 4, 5 | SNPs 1, 2, 3, 4, 5 | SNPs 1, 2, 3, 4, 5 | SNPs 1, 2, 3, 4, 5 |
| Template | S-7, 26, 30, 37 | S-7, 26, 30, 37 | S-7, 26, 30, 37 | S-7, 26, 30, 37 | S-7, 26, 30, 37 | S-7, 26, 30, 37 | S-7, 26, 30, 37 | S-7, 26, 30, 37 |
| dXTP | dATP | dCTP | dGTP | dTTP | dATP | dCTP | dGTP | dTTP |

The reactions were carried out as described in Example 8. Briefly, the template and probe DNAs are combined and incubated with Apyrase, Ampligase and Taq DNA Polymerase Stoffel fragment for 4 minutes at 20° C. to degrade the dXTPs. The enzyme mix was prepared by combining 109.1 ul of water, 18 ul 10×pfu Ampligase buffer; 2.7 ul of each barcode olio; 4.5 ul of each template DNA; 1.8 ul Apyrase at 50 mU/ul; 1.125 ul Ampligase dilution (5 ul Ampligase buffer; 44.33 water and 0.67 ul Ampligase 5 u/ul); and 0.45 ul Taq DNA Polymerase Stoffel fragment at 10 u/ul. 18 ul of the mix were transferred to strip tubes, which were incubated for 4 minutes at 20° C. to degrade potential contaminating nucleotides. The reactions were then denatured by incubation at 95° C. for 5 minutes and annealed at 65° C. for 15 minutes. 2 ul of the respective dXTP was added and the reactions incubated for 10 minutes at 65° C. In the ligation reaction (20 ul), the final barcode probe concentration was 0.015 picomoles/ul and, template concentration was approximately 2 femtomoles/ul. Final ligase concentration was 0.00042 units/ul in the ligation reaction (0.0084 units total).

0.2 ul of each reaction was added to 18 ul of runoff mix preheated to 95° C. prepared by combining 34 ul 10×Taq Gold buffer; 40.8 ul dNTPs at 1.25 mM each; 2.25 ul of AmpliTaq gold DNA Polymerase at 5 u/ul; 2.72 ul P1bar biotin primer (SEQ ID NO: 1) at 100 pmol/ul; 34 ul MgCl2 at 25 mM; and 306 ul water. The reactions were heat denatured for 10 minutes at 95° C. and runoff products obtained by incubation for 2 minutes at 60° C. The reactions were then brought to 4° C.

Biotin cleanup was performed as described in Example 6. Briefly, the beads were washed as described and resuspended in 2 volumes 2M NaCl. 20 ul of each reaction were added to 20 ul of beads to get a 1M NaCl mix. The mix was incubated at 43° C. for 15 min, pipetting up and down every 5 minutes. The beads were then washed 6 times in 200 ul of 0.5 M NaCl/0.5 M NaOH buffer, followed by a wash with 200 ul of 0.5 M NaCl in TE. The beads were resuspended in 200 ul of: 100 mM NaCl, TE, 0.25% DMSO, 0.01% Triton, and heated for 15-20 min at 70° C. This releases non-specifically bound product to beads. The beads were then washed again with 200 ul TE. The beads were resuspended in original sample volume (eg. 20 ul) using 1×TE.

20 ul of the reactions were transferred to a UNG/PCR mix prepared by combining 18 ul of 10×Taq Gold buffer; 21.6 ul dNTPs at 1.25 mM each; 1.35 ul AmpliTaq Gold DNA Polymerase at 100 pmol·ul; 1.44 ul P1Bar primer (SEQ ID NO 1) at 100 pmol/ul; 9 ul UNG; 2.88 ul M13 biotin primer (SEQ ID NO: 3) at 100 pmol/ul; 18 ul MgCl2 at 25 mM; and 107.9 ul water. The reactions were incubated for 20 minutes at 37° C., heat denatured for 5 minutes at 95° C. and subjected to 14 amplification cycles of 20 seconds at 95° C.; 1 minute at 69.6° C. (decreasing by 0.4° C. every cycle); and 10 seconds at 72° C. and 20 amplification cycles of 45 seconds at 64° C.; and 10 seconds at 72° C. The reactions are then incubated for 10 seconds at 72° C. and further incubated at 4° C.

The amplified products were analyzed by gel electrophoresis and the result indicate that an amplification product is seen for each nucleotide as expected (A, C, G, T in lanes 1, 2, 3, 4 respectively). The five SNPs tested had the following nucleotide matches: SNP1, dATP; SNP2, dGTP; SNP3, dTTP: and both SNP4 and SNP5, dCTP. Therefore different SNPs are amplified in each lane although this cannot be distinguished by gel electrophoresis The amplified products were further then analyzed by hybridization of each multiplexed reaction to a DNA chip. Each dXTP reaction (multiplexed to 5 probes) was hybridized to a separate chip. In each case, the hybridization mixture consisted of the following: 2.0 ul of the above PCR reaction, 0.5 ul of a control (border) oligo at 0.7 fm/ul, 2.9 ul M13 complement oligo at 10 pm/ul (10 fold excess over the M13 primer of the PCR reaction), brought up to 160 ul in 6×SSPE-T buffer (6×SSPE buffer with 0.005% Triton). This mixture was denatured for 2 min at 95° C. C and then put incubated on ice for 5 min. The solution was loaded on a DNA chip and hybridized at 42° C. C for 4 hours. After this period, the chip was washed with 6×SSPE-T, 5 times and loaded with the following for fluorescent labeling: 0.5 ul of Streptavidin R-Phycoerythrin conjugate (1 mg/ml), 10 ul of BSA (20 mg/ml), brought up to 160 ul in SSPE-T buffer. The chip was incubated for 10 minutes at 42 C. After this, the chip was again washed with SSPE-T buffer 5 times and loaded onto a laser fluorescence scanner for analysis of the multiplexed reaction products. The signal at each of the five probe features of interest were averaged over the 8×5 pixels per feature, background subtracted and then normalized using the average signal intensity of the control (border) features. This effectively normalized the difference in hybridization efficiency on the four different chips. Table 11 shows normalized signal intensity from four hybridizations, one for each nucleotide. The signal:noise ratio corresponds to the normalized signal at the expected nucleotide to the highest normalized signal at the other three nucleotides.

TABLE 11

Normalized signal intensity from DNA chip hybridization

| | A Signal | C Signal | G Signal | T Signal | Base call | Signal:Noise |
|---|---|---|---|---|---|---|
| Probe 1 | 1.5 | 0.01 | 0.02 | 0.03 | Correct | 50:1 |
| Probe 2 | 0.2 | 0.04 | 1.3 | 0.16 | Correct | 6.5:1 |
| Probe 3 | 0.06 | 0 | 0 | 0.56 | Correct | 9:1 |
| Probe 4 | 0.03 | 0.14 | 0.02 | 0.01 | Correct | 5:1 |
| Probe 5 | 0.24 | 0.48 | 0.18 | 0.27 | Correct | 2:1 |

The results of the DNA chips hybridization are not shown, however, three separate hybridizations were done. The reaction to which dATP was added was colored in green. The reaction to which dCTP was added was in blue. The reaction to which dGTP was in red. The allele calls are shown by the color of the spot at the given SNP tag location; SNP1: A; SNP2: G and SNP5: C.

Thus, this example demonstrates that multiplexing is possible with the method of the invention, and that the different SNPs can easily be identified by hybridization to DNA chips.

Example 10

Multiplexing with *S. cerevisiae* Genomic DNA

This example demonstrates multiplexing on yeast genomic DNA using gap modular synthesis and Apyrase and UNG to reduce background.

The template DNA from *S. cerevisiae* (S96 genomic DNA at 197 ng/ul [what is S96 DNA? we tested two strain of yeast 596 and YJM, in all examples, 596 was used]) was incubated with one or more SNP probes, as set forth in Table 12. The sequences of the two part probes are provided in the previous examples.

TABLE 12

| Components of the reactions | | | | | | | | |
|---|---|---|---|---|---|---|---|---|
| | Reaction | | | | | | | |
| | 1 | 2 | 3 | 4 | 5 | 6 | 7 | 8 |
| Probe dXTP | SNP 1 dATP | SNP 1 dCTP | SNP 1 dGTP | SNP 1 dTTP | SNP 2 dATP | SNP 2 dCTP | SNP 2 dGTP | SNP 2 dTTP |
| | Reaction | | | | | | | |
| | 9 | 10 | 11 | 12 | 13 | 14 | 15 | 16 |
| Probe dXTP | SNP 3 dATP | SNP 3 dCTP | SNP 3 dGTP | SNP 3 dTTP | SNP 4 dATP | SNP 4 dCTP | SNP 4 dGTP | SNP 4 dTTP |
| | Reaction | | | | | | | |
| | 17 | 18 | 19 | 20 | 21 | 22 | 23 | 24 |
| Probe dXTP | SNP 5 dATP | SNP 5 dCTP | SNP 5 dGTP | SNP 5 dTTP | All 5 probes dATP | All 5 probes dCTP | All 5 probes dGTP | All 5 probes dTTP |

The reactions were carried out as described in Example 9. Briefly, the template and probe DNAs were combined and incubated with Apyrase, Ampligase and Taq DNA Polymerase Stoffel fragment for 4 minutes at 20° C. to degrade the dXTPs. An enzyme mix was prepared by combining 409.95 ul of water, 60 ul 10×pfu Ampligase buffer; 15.3 ul of template DNA at 197 ng/ul; 6 ul Apyrase at 50 mU/ul; 0.75 ul Ampligase; and 3 ul Taq DNA Polymerase Stoffel fragment at 10 u/ul. 18 ul were transferred to strip tubes. The final mix was prepared by combining (for 5 reactions) 74.25 ul enzyme mix; 1.35 ul of each barcode oligoprobe and TE if necessary to obtain a volume of 81 ul.

The reactions were then denatured by incubation at 95° C. and annealed at 65° C. for 15 minutes. 2 ul of the respective dXTP at 0.1 mM was added and the reactions were incubated for 10 minutes at 65° C. In the ligation reaction (20 ul), the final barcode probe concentration was 0.015 picomoles/ul.

3 ul of each reaction was added to 27 ul of runoff mix prepared by combining 78 ul 10×Taq Gold buffer; 93.6 ul dNTPs at 1.25 mM each; 5.85 ul of AmpliTaq gold DNA Polymerase at 5 u/ul; 6.24 ul P1bar biotin primer (SEQ ID NO 1) at 100 pmol/ul; 78 ul MgCl2 at 25 mM; and 440.31 ul water. The reactions were heat denatured (and Taq activated) for 10 minutes at 95° C. and runoff products obtained by incubation for 2 minutes at 60° C. The reactions were then, and chilled by incubation at 4° C.

20 ul of the reactions were transferred to a UNG/PCR mix prepared by combining 78 ul of 10×Taq Gold buffer; 93.6 ul dNTPs at 1.25 mM each; 78 ul AmpliTaq Gold DNA Polymerase; 39 ul UNG; 12.48 ul M13 primer (SEQ ID NO: 3) at 100 pmol/ul; 6.24 ul P1Bar primer (SEQ ID NO: 1) at 100 pmol/ul; 78 ul MgCl2 at 25 mM; and 466.83 ul water. The reactions were incubated for 20 minutes at 37° C., heat denatured for 10 minutes at 95° C. and subjected to 14 amplification cycles of 20 seconds at 95° C.; 1 minute at 69.6° C. (decreasing by 0.4° C. every cycle), followed by 30 amplification cycles of 20 seconds at 95° C.; 45 seconds at 64° C.; and 10 seconds at 72° C. The reactions were then incubated for 10 seconds at 72° C. and then soaked at 4° C.

The amplification products were analyzed as described in Example 8. The results clearly show the presence of amplification products in reactions in which the dNTP that was added is complementary to the SNP in the template DNA. For example, lane 7 shows a reaction with a SNP2 probe and dGTP, which is the nucleotide that is complementary to the SNP in the template DNA at that location. Similarly, lane 18 shows an amplification product resulting from the addition of dCTP which is the complementary nucleotide to SNP5 in template DNA. In reactions 22, 23 and 24, bands are also clearly visible indicating that amplification does occur in multiplexed reactions.

The dCTP and the dGTP nucleotide reactions were also analyzed by hybridization to DNA chips. The hybridization conditions were similar to those in the example 9, except that 20 ul of the PCR reaction was used in the hybridization mix and the chip was hybridized for 12 hours. Table 13 shows normalized signal intensity from the two hybridizations. The Signal:Noise ratio corresponds to the normalized signal at the expected nucleotide to the normalized signal at the other nucleotide.

TABLE 13

| Normalized signal intensity from DNA chip hybridization | | | | |
|---|---|---|---|---|
| | C Signal | G Signal | Base call | Signal:Noise |
| Probe 2 | 0.13 | 0.39 | Correct | 3:1 |
| Probe 4 | 0.16 | 0.08 | Correct | 2:1 |
| Probe 5 | 0.13 | 0.05 | Correct | 2.5:1 |

Example 11

Detection of SNPs in Very High Complexity DNA

To mimic the complexity and quantity of DNA needed to genotype human DNA, yet still use the current yeast specific probes, *S. cerevisiae* DNA was mixed with calf thymus DNA in an equimolar ratio or further diluted and then performed the SNP genotyping reaction. Calf thymus DNA is mammalian DNA and contains roughly the same complexity in base pairs as does human DNA.

The reactions are set forth in Table 143. Yeast genomic DNA (200 ng/ul) was serially diluted into calf thymus (100 ng/ul) as follows, 1 ul of yeast S96 was mixed with 19 ul of calf thymus (Dilution 1). 2 ul of Dilution 1 were mixed into 18 ul of calf thymus (Dilution 2), 2 ul of Dilution 2 were mixed into 18 ul of calf thymus (Dilution 3).

TABLE 143

| | Components of the reactions | | | | | | | |
|---|---|---|---|---|---|---|---|---|
| | Reaction | | | | | | | |
| | 1 | 2 | 3 | 4 | 5 | 6 | 7 | 8 |
| probe | SNP5 | SNP5 | SNP5 | SNP5 | SNP5 | SNP5 | SNP5 | SNP5 |
| Yeast S96 Genomic uncut | 100 ng | 100 ng | 10 ng | 10 ng | 1 ng | 1 ng | 0.1 ng | 0.1 ng |
| Calf Thymus | 100 ng | 100 ng | 100 ng | 100 ng | 100 ng | 100 ng | 100 ng | 100 ng |
| dXTP | C | G | C | G | C | G | C | G |

An enzyme mix containing the template and probe DNAs was prepared by combining (per reaction) 4.875; 11.875; 13.875; or 14.575 ul of water; 2 ul 10×pfu Ampligase buffer; 0.3 ul of barcode olio; 10, 3, 1, or 0.3 ul of yeast genomic dilution; 0.2 ul Apyrase at 50 mU/ul; 0.125 ul Ampligase; and 0.5 ul Taq DNA Polymerase Stoffel fragment at 10 u/ul. 18 ul were transferred to strip tubes. dXTPs Potential contaminating nucleotides were degraded by incubation for 20 minutes at 4° C. The reactions were then denatured by incubation at 95° C. for 5 minutes and ramped down to 65° C. 2 ul dXTP at 100 uM dilution was added and the reactions were incubated at 65° C. for 10 minutes.

For Taq run-off, 2 ul of ligation mix was added to 18 ul of run-off mix and heat denatured for 10 minutes at 95° C. Runoff mix was prepared by combining (per reaction) 2 ul 10×Taq Gold buffer; 0.75 ul dNTPs at 4 mM each; 0.15 ul of AmpliTaq gold DNA Polymerase at 5 u/ul; 0.16 ul P1bar biotin primer (SEQ ID NO 1) at 10 pmol/ul; 2 ul MgCl2 at 25 mM; 1 ul UNG; and 13.78 ul water. The reactions were heat denatured (and Taq activated) for 10 minutes at 95° C. and runoff products obtained by incubation for 2 minutes at 60° C.

After runoff, while the mixture is still at 60° C., 20 ul of the extension reaction were transferred into a UNG/PCR mix, prepared by combining (per reaction) 2 ul of 10×Taq Gold buffer; 0.75 ul dNTPs at 1.25 mM each; 0.15 ul AmpliTaq Gold DNA Polymerase at 5 units/ul; 1 ul UNG; 0.16 ul M13 primer (SEQ ID NO 3) at 100 pmol/ul; 0.16 ul P1Bar primer (SEQ ID NO 1) at 100 pmol/ul; 2 ul MgCl2 at 25 mM; and 13.78 ul water. The reactions were incubated for 20 minutes at 37° C., heat denatured for 5 minutes at 95° C. and subjected to 35 amplification cycles of 20 seconds at 95° C.; 45 seconds at 64° C.; and 10 seconds at 72° C. The reactions are then incubated for 10 seconds at 72° C. and then soaked at 4° C.

The amplification products were analyzed by gel electrophoresis as described in the previous examples. The results indicate the presence of an amplification product in all lanes having reactions done in the presence of dCTP, the nucleotide that is complementary to the SNP in the template nucleic acid. This demonstrates that, even in the presence of several billion base pairs of DNA, a SNP can be detected by this method.

Example 12

Amplification of SNPs in Human DNA

This example demonstrates the use of the system to identify SNPs in human genomic DNA. This example used the polymerase/ligase method with two part synthesized probes and the Apyrase and UNG background reduction methods.

Two DNA samples were obtained from a Northern European donor and an Indian donor. The samples were screened for two markers in the human ATM gene, GenBank accession number HSU82828. This gene contains many polymorphisms including two SNPs: one at base 46611 (intron 17; G to A: 34,107) and the second one at 60136 (Intron 22; T to C: 35107). The probe designed to detect the SNP at base 46611 was prepared by ligating two oligonucleotides using a bridging oligonucleotide as described above, to produce a probe having the nucleotide sequence 5' AGAATAATTGTTTT-TATTTCTTTGAAC/UGTCCACGAGGTCTCTAGTC/TG-TAAAACGACGGCCAGT/UATGCGTACCCTCGACT-GAG/TTTAAA/TAGAGAAAACACTGTCTGC C 3' (SEQ ID NO: 264), represented as homology1/primer1/primer2/barcode/DraI/homology2 ("U" indicates uracil bases). The probe to detect the second SNP was also constructed by ligating two oligonucleotides using a bridging oligonucleotides, to produce a probe having the nucleotide sequence 5' AATAACCTTTCAGTGAGTTTTGAC/UGTCCACGAG-GTCTCTAGTC/TGTAAAACGACGGCCAGT/UACTGT-CACCGGAGTCTGAG/TTTAAA/GACATATTGGAAG-TAACTTA 3' (SEQ ID NO: 275).

The compositions of the reactions are set forth in Table 145.

TABLE 154

| | Components of the reactions | | | | | | | |
|---|---|---|---|---|---|---|---|---|
| | Reactions | | | | | | | |
| | 1 | 2 | 3 | 4 | 5 | 6 | 7 | 8 |
| probe oligo | ATM46611 | ATM46611 | ATM46611 | ATM46611 | ATM60136 | ATM60136 | ATM60136 | ATM60136 |
| Genomic templatee | NE | NE | NE | NE | NE | NE | NE | NE |
| dXTP | dATP | dCTP | dGTP | dTTP | dATP | dCTP | dGTP | dTTP |

TABLE 154-continued

| Components of the reactions | | | | | | | | |
|---|---|---|---|---|---|---|---|---|
| | Reactions | | | | | | | |
| | 9 | 10 | 11 | 12 | 13 | 14 | 15 | 16 |
| probe oligo | ATM46611 | ATM46611 | ATM46611 | ATM46611 | ATM60136 | ATM60136 | ATM60136 | ATM60136 |
| Genomic templatee | EI | EI | EI | EI | EI | EI | EI | EI |
| dXTP | dATP | dCTP | dGTP | dTTP | dATP | dCTP | dGTP | dTTP |

NE stands for North European and EI stands for Indian.

An enzyme mix containing the template and probe DNAs was prepared by combining 232.7 ul of water; 40 ul 10×pfu Ampligase buffer; 4 ul Apyrase at 50 mU/ul; 2.5 ul Ampligase; and 9.5 ul Taq DNA Polymerase Stoffel fragment at 10 u/ul. Four enzyme/DNA mixes were prepared by combining 65.07 ul enzyme mix; 13.5 ul of template DNA; and 0.54 ul probe DNA. 18 ul were transferred to strip tubes. dXTPs Potential contaminating nucleotides were degraded by incubation for 20 minutes at 4° C. The reactions were then denatured by incubation at 95° C. for 5 minutes and ramped down to 65° C. for about 15 minutes, 2 ul dXTP at 100 uM dilution was added and the reactions were incubated at 58 for 10 minutes.

For Taq run-off, 2 ul of ligation mix was added to 18 ul of run-off mix warmed to 95° C., prepared by combining 34 ul 10×Taq Gold buffer; 12.75 ul dNTPs at 1.25 mM each; 2.55 ul of AmpliTaq gold DNA Polymerase at 5 u/ul; 2.72 ul P1bar biotin primer (SEQ ID NO: 1) at 10 pmol/ul; 34 ul MgCl2 at 25 mM; and 220 ul water. The reactions were heat denatured (and Taq activated) for 10 minutes at 95° C. and runoff products obtained by incubation for 2 minutes at 60° C., and then chilled at 4° C.

20 ul of the extension reaction were transferred into a UNG/PCR mix, prepared by combining 34 ul of 10×Taq Gold buffer; 12.75 ul dNTPs at 1.25 mM each; 2.55 ul AmpliTaq Gold DNA Polymerase at 5 units/ul; 17 ul UNG 1 unit/ul; 2.72 ul M13 primer (SEQ ID NO 3) at 100 pmol/ul; 2.72 ul P1Bar primer (SEQ ID NO 1) at 100 pmol/ul; 34 ul MgCl2 at 25 mM; and 234.26 ul water. The reactions were incubated for 20 minutes at 37° C., heat denatured for 10 minutes at 95° C. and subjected to 35 amplification cycles of 20 seconds at 95° C.; 45 seconds at 64° C.; and 10 seconds at 72° C. The reactions are then incubated for 10 seconds at 72° C. and then soaked at 4° C.

The amplification products were analyzed by gel electrophoresis as described in previous examples. The results indicate the presence of an amplification product in lanes 3 and 11 for the ATM46611 SNP indicating that both genomic DNAs are homozygous G for this SNP. Amplification products in lane 6 but not 8 for the northern european donor indicates that this genomic DNA is homozygous for C for the ATM60136 SNP while the east indian genomic DNA is heterozygous for C and T due to the presence of products in the lanes 14 and 16 lanes, respectively.

Example 13

Increase in Signal Due to the Release of Ligated Circular Probe from Genomic DNA Using Uracil-N-Glycosylase Digestion Because it is difficult for polymerases to copy a primed circular probe while it is circularized around long DNA templates, signal is improved if the ligated probe is released from the genomic DNA template allowing free access to the ligated probe by primers and polymerase. In this example, this is achieved by depyrimidization of the ligated circularized probe by uracil-N-glycosylase also referred to as UNG) followed by heat scission of the abasic site by heat linearizes the ligated probe which can then be heat denatured from the genomic DNA template.

This example describes a method comparing probes containing (probes A9U and A10U) and not containing (A9 and A10) the UNG target base, uracil (dUTP or simply U) in a reaction containing or not containing the digesting enzyme uracil-N-glycosylase.

The template DNA used was purified human genomic DNA and the probes used have the nucleotide

```
sequence 5'
A9
                                      (SEQ ID NO: X)
TATGACCAGAGGTTTCTGACTGTCCACGAGGTCTCTAGTCTGTAAAACG
ACGGCCAGTGGGTACATCCAAGCAACCGAGTTTCCTGGCATTATATCAT
CT

A10
                                      (SEQ ID NO: X)
ACCTGGAAGCCAACTTCGTCCACGAGGTCTCTAGTCTGTAAAACGACGG
CCAGTAGCGTACTCTGAATGCCGTCGCCAGAAATTAGTCAAGGAAA

A9
                                      (SEQ ID NO: X)
UTATGACCAGAGGTTTCTGACTGTCCACGAGGTCTCTAGTCUTGTAAAA
CGACGGCCAGTGGGTACATCCAAGCAACCGAGTTTCCTGGCATTATATC
ATCT

A10
                                      (SEQ ID NO: X)
UCACCTGGAAGCCAACTTCGTCCACGAGGTCTCTAGTCUTGTAAAACGA
CGGCCAGTAGCGTACTCTGAATGCCGTCGCCAGAAATTAGTCAAGGAAA
```

A single nucleotide gap fill reaction mix was prepared by mixing 48 ul of 10× ampligase reaction buffer (Epicentre), 0.6 ul apyrase 500 milliunits/ul (Sigma), 2.4 ul Tag polymerase Stoffel fragment 10 units/ul (ABI), 0.6 ul Ampligase enzyme 5 units/ul (Epicentre), 24 ul human genomic DNA 100 ng/ul, and 345 ul water. 44.75 ul of this reaction mix was added to 0.25 ul of each probe (1.25 femptomoles/ul) 9 ul of which was pippetted into each of four positions in a reaction plate, one for each nucleotide.

The reaction mixtures (containing the DNAs) were incubate for 4 minutes at 20° C., denatured for 5 minutes at 95° C. and annealed for 15 minutes at 55° C. To each tube 1 ul of 1.25 micromolar deoxynucleotide (Pharmacia) was added (as indicated in table XX) and the reaction was incubated 10 minutes at 55° C. At this point, probes have been circularized around the genomic DNA if the correct nucleotide was added. The reaction mixture was then incubated at 95° C. for 2 minutes and then brought to 37° C. To each well, 25 ul of uracil-N-glycosylase mix was added consisting of 2.5 ul 10×Taq gold buffer (ABI), 1.6 ul 25 mM MgCl2, water, and 10 ul of UNG (if indicated in table XX). The reactions were incubated 20 minutes at 37° C. for depyrimidization, then for 10 minutes at 95° C. to break the abasic site.

TABLE XX components of the different reactions:

| | Reaction | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Probe | A10 | A9 | A10 | A9 | A10 | A9 | A10 | A9 | A10U | A9U | A10U | A9U | A10U | A9U | A10U | A9U |
| dXTP | dATP | dATP | dCTP | dCTP | dGTP | dGTP | dTTP | dTTP | dATP | dATP | dCTP | dCTP | dGTP | dGTP | dTTP | dTTP |
| UNG | – | – | – | – | – | – | – | – | – | – | – | – | – | – | – | – |
| | Reaction | | | | | | | | | | | | | | | |
| | 1 | 2 | 3 | 4 | 5 | 6 | 7 | 8 | 9 | 10 | 11 | 12 | 13 | 14 | 15 | 16 |
| Probe | A10 | A9 | A10 | A9 | A10 | A9 | A10 | A9 | A10U | A9U | A10U | A9U | A10U | A9U | A10U | A9U |
| dXTP | dATP | dATP | dCTP | dCTP | dGTP | dGTP | dTTP | dTTP | dATP | dATP | dCTP | dCTP | dGTP | dGTP | dTTP | dTTP |
| UNG | + | + | + | + | + | + | + | + | + | + | + | + | + | + | + | 25 |

Ligated probe products were amplified by adding 25 ul of an amplification mix consisting of 2.5 ul 10×Taq gold buffer (ABI), 1.6 ul 25 mM MgCl2, 2.24 ul dNTPs at 1.25 mM each, 0.08 ul of M13 primer (SEQ ID NO: XX) at 197 pmol/ul, 0.09 ul of P1Bar primer (SEQ ID NO: XX) at 186 pmol/ul, 0.4 ul Amplitaq Gold DNA polymerase 5 units/ul (ABI), and water, and thermocycling the mixture 20 seconds at 95° C., 45 seconds at 64° C., and 10 seconds at 72° C. for 31 cycles 20 ul of each reaction was then subjected to electrophoresis in 4% agarose, and the bands were visualized as described in the previous examples. The results indicate the signal, which is a band seen migrating at 100 base pairs as compared to the DNA ladder run to the left, is greatly increased in reactions with probes that contain a uracil and were incubated with uracil-N-glycosylase indicating that both the enzyme and its target uracil on the probe are necessary to release the circularized probe from the genomic DNA template and allow efficient amplification.

We claim:

1. A method of targeted amplification of nucleic acids comprising:

contacting a sample containing one or more target nucleic acid sequences with one or more precircle probes, wherein each precircle probe comprises at least a first and second targeting domain which hybridize to a target nucleic acid sequence and which flank at least one universal priming sequence, under conditions appropriate for hybridization of the first and second targeting domains of a precircle probe with a target nucleic acid sequence; extending the precircle probe with a polymerase such that the target nucleic acid sequence is copied, thereby producing an extended precircle probe; ligating one end of the extended precircle probe to the other end to create a closed circular probe;

optionally removing linear nucleic acid sequences remaining in the sample;

cleaving the closed circular probe prior to amplification; and amplifying the cleaved circular probe to produce amplified target nucleic acid sequence.

2. A method according to claim 1 wherein optionally removing linear nucleic acid sequences comprises treating the sample with an exonuclease.

3. A method according to claim 1 wherein amplifying the closed circular probe comprises using rolling circle amplification and/or optional PCR amplification.

4. A method according to claim 1 further comprising removing linear nucleic acid sequences remaining in the sample.

5. A method according to claim 1 wherein amplifying the closed circular probe comprises using primers directed at the universal priming sequence.

6. A method according to claim 1 further comprising recircularizing the amplified target nucleic sequence using the universal priming sequence.

* * * * *

UNITED STATES PATENT AND TRADEMARK OFFICE

CERTIFICATE OF CORRECTION

PATENT NO. : 7,993,880 B2
APPLICATION NO. : 12/709319
DATED : August 9, 2011
INVENTOR(S) : Willis et al.

It is certified that error appears in the above-identified patent and that said Letters Patent is hereby corrected as shown below:

<u>In the Claims:</u>

Column 82, claim 6, line 8, insert the word -- acid -- after "nucleic"

Signed and Sealed this
Thirteenth Day of December, 2011

David J. Kappos
*Director of the United States Patent and Trademark Office*

SEQUENCE LISTING

```
<160> NUMBER OF SEQ ID NOS: 29

<210> SEQ ID NO 1
<211> LENGTH: 38
<212> TYPE: DNA
<213> ORGANISM: Saccharomyces cerevisiae

<400> SEQUENCE: 1

atctcgggat atcagactta gcggcaccgt cctcaccg                              38


<210> SEQ ID NO 2
<211> LENGTH: 38
<212> TYPE: DNA
<213> ORGANISM: Saccharomyces cerevisiae

<400> SEQUENCE: 2

atctcgggat atcagactta gcggtaccgt cctcaccg                              38


<210> SEQ ID NO 3
<211> LENGTH: 92
<212> TYPE: DNA
<213> ORGANISM: Artificial Sequence
<220> FEATURE:
<223> OTHER INFORMATION: synthetic.

<400> SEQUENCE: 3

ccgctaagtc tgatatcccg agatgtccac gaggtctcta gtcgacctgc agcgtacgcg      60

gacctcaagt gaagtacacg gtgaggacgg tg                                    92


<210> SEQ ID NO 4
<211> LENGTH: 92
<212> TYPE: DNA
<213> ORGANISM: Artificial Sequence
<220> FEATURE:
```

<223> OTHER INFORMATION: synthetic.

<400> SEQUENCE: 4
ccgctaagtc tgatatcccg agatgtccac gaggtctcta gtcgacctgc agcgtacgcg 60
gacctcaagt gaagtacacg gtgaggacgg ta 92

<210> SEQ ID NO 5
<211> LENGTH: 19
<212> TYPE: DNA
<213> ORGANISM: Artificial Sequence
<220> FEATURE:
<223> OTHER INFORMATION: synthetic.

<400> SEQUENCE: 5
gactagagac ctcgtggac 19

<210> SEQ ID NO 6
<211> LENGTH: 15
<212> TYPE: DNA
<213> ORGANISM: Artificial Sequence
<220> FEATURE:
<223> OTHER INFORMATION: synthetic.

<400> SEQUENCE: 6
gacctgcagc gtacg 15

<210> SEQ ID NO 7
<211> LENGTH: 42
<212> TYPE: DNA
<213> ORGANISM: Saccharomyces cerevisiae

<400> SEQUENCE: 7
acatttagat ctgcagtttc taatatgaat tcagtggaaa at 42

<210> SEQ ID NO 8
<211> LENGTH: 36
<212> TYPE: DNA
<213> ORGANISM: Saccharomyces cerevisiae

<400> SEQUENCE: 8
tcgggatatc agacttagcg gcaccgtcct caccgt 36

<210> SEQ ID NO 9
<211> LENGTH: 36
<212> TYPE: DNA
<213> ORGANISM: Saccharomyces cerevisiae

<400> SEQUENCE: 9
gatcaaatgc gaccatattc atcaaactta taggcg 36

<210> SEQ ID NO 10
<211> LENGTH: 42
<212> TYPE: DNA
<213> ORGANISM: Saccharomyces cerevisiae

<400> SEQUENCE: 10
ccagtccctt gagttcgcga atagtaattt tggtgatacc tg 42

<210> SEQ ID NO 11
<211> LENGTH: 103
<212> TYPE: DNA
<213> ORGANISM: Artificial Sequence
<220> FEATURE:
<223> OTHER INFORMATION: synthetic.

<400> SEQUENCE: 11
gaaactgcag atctaaatgt accugtccac gaggtctcta gtctgtaaaa cgacggccag 60
tugctggagt tcgcacgcta taattttcca ctgaattcat att 103

<210> SEQ ID NO 12
<211> LENGTH: 103
<212> TYPE: DNA
<213> ORGANISM: Artificial Sequence
<220> FEATURE:
<223> OTHER INFORMATION: synthetic.

<400> SEQUENCE: 12
ccgctaagtc tgatatcccg agatugtcca cgaggtctct agtctgtaaa acgacggcca 60
gtucaaaggt ggagctgcac acttttaaaa cggtgaggac ggt 103

<210> SEQ ID NO 13
<211> LENGTH: 103
<212> TYPE: DNA
<213> ORGANISM: Artificial Sequence
<220> FEATURE:
<223> OTHER INFORMATION: synthetic.

<400> SEQUENCE: 13
atggtcgcat ttgatcgagu gtccacgagg tctctagtct gtaaaacgac ggccagtugc 60
ctgggttacg tgtctacttt taaacgccta taagtttgat gaa 103

<210> SEQ ID NO 14
<211> LENGTH: 103
<212> TYPE: DNA
<213> ORGANISM: Artificial Sequence
<220> FEATURE:
<223> OTHER INFORMATION: synthetic.

<400> SEQUENCE: 14
gcgaactcaa gggactggta cugtccacga ggtctctagt ctgtaaaacg acggccagtu 60
gcaatatgta actctctggg caggtatcac caaaattact att 103

<210> SEQ ID NO 15
<211> LENGTH: 30
<212> TYPE: DNA
<213> ORGANISM: Artificial Sequence
<220> FEATURE:
<223> OTHER INFORMATION: synthetic.

<400> SEQUENCE: 15
gtcgttttac agactagaga cctcgtggac 30

<210> SEQ ID NO 16
<211> LENGTH: 18
<212> TYPE: DNA
<213> ORGANISM: Artificial Sequence
<220> FEATURE:
<223> OTHER INFORMATION: synthetic.

<400> SEQUENCE: 16
tgtaaaacga cggccagt 18

<210> SEQ ID NO 17
<211> LENGTH: 30
<212> TYPE: DNA
<213> ORGANISM: Artificial Sequence
<220> FEATURE:
<223> OTHER INFORMATION: synthetic.

<400> SEQUENCE: 17
gtcgttttac agactagaga cctcgtggac 30

<210> SEQ ID NO 18
<211> LENGTH: 42
<212> TYPE: DNA
<213> ORGANISM: Artificial Sequence
<220> FEATURE:
<223> OTHER INFORMATION: synthetic.

<400> SEQUENCE: 18
ccagtccctt gagttcgcga atagtaattt tggtgatacc tg 42

<210> SEQ ID NO 19
<211> LENGTH: 37
<212> TYPE: DNA
<213> ORGANISM: Artificial Sequence
<220> FEATURE:
<223> OTHER INFORMATION: synthetic.

<400> SEQUENCE: 19
actggccgtc gttttacaga ctagagacct cgtggac 37

<210> SEQ ID NO 20
<211> LENGTH: 42
<212> TYPE: DNA
<213> ORGANISM: Saccharomyces cerevisiae
<400> SEQUENCE: 20
acatttagat ctgcagtttc taatatgaat tcagtggaaa at 42

<210> SEQ ID NO 21
<211> LENGTH: 36
<212> TYPE: DNA
<213> ORGANISM: Saccharomyces cerevisiae
<400> SEQUENCE: 21
gatcaaatgc gaccatattc atcaaactta taggcg 36

<210> SEQ ID NO 22
<211> LENGTH: 37
<212> TYPE: DNA
<213> ORGANISM: Saccharomyces cerevisiae
<400> SEQUENCE: 22
tactgtaccc atttttttgt cgcttaaggt ttcgcgt 37

<210> SEQ ID NO 23
<211> LENGTH: 103
<212> TYPE: DNA
<213> ORGANISM: Artificial Sequence
<220> FEATURE:
<223> OTHER INFORMATION: synthetic.

<400> SEQUENCE: 23
acaaaaaaat gggtacagta taaugtccac gaggtctcta gtctgtaaaa cgacggccag 60
tuggtagtac ggtgctctta catttaaaac gcgaaacctt aag 103

<210> SEQ ID NO 24
<211> LENGTH: 111
<212> TYPE: DNA
<213> ORGANISM: Artificial Sequence
<220> FEATURE:
<223> OTHER INFORMATION: synthetic.

-continued

<400> SEQUENCE: 24
agaataattg tttttatttc tttgaacugt ccacgaggtc tctagtctgt aaaacgacgg 60
ccagtuatgc gtaccctcga ctgagtttaa atagagaaaa cactgtctgc c 111

<210> SEQ ID NO 25
<211> LENGTH: 108
<212> TYPE: DNA
<213> ORGANISM: Artificial Sequence
<220> FEATURE:
<223> OTHER INFORMATION: synthetic.

<400> SEQUENCE: 25
aataaccttt cagtgagttt tgacugtcca cgaggtctct agtctgtaaa acgacggcca 60
gtuactgtca ccggagtctg agtttaaaga catattggaa gtaactta 108

<210> SEQ ID NO 26
<211> LENGTH: 100
<212> TYPE: DNA
<213> ORGANISM: Homo sapiens

<400> SEQUENCE: 26
tatgaccaga ggtttctgac tgtccacgag gtctctagtc tgtaaaacga cggccagtgg 60
gtacatccaa gcaaccgagt ttcctggcat tatatcatct 100

<210> SEQ ID NO 27
<211> LENGTH: 95
<212> TYPE: DNA
<213> ORGANISM: Homo sapiens

<400> SEQUENCE: 27
acctggaagc caacttcgtc cacgaggtct ctagtctgta aaacgacggc cagtagcgta 60
ctctgaatgc cgtcgccaga aattagtcaa ggaaa 95

<210> SEQ ID NO 28
<211> LENGTH: 102
<212> TYPE: DNA
<213> ORGANISM: Homo sapiens

<400> SEQUENCE: 28
utatgaccag aggtttctga ctgtccacga ggtctctagt cutgtaaaac gacggccagt 60
gggtacatcc aagcaaccga gtttcctggc attatatcat ct 102

<210> SEQ ID NO 29
<211> LENGTH: 98
<212> TYPE: DNA
<213> ORGANISM: Homo sapiens

<400> SEQUENCE: 29
ucacctggaa gccaacttcg tccacgaggt ctctagtcut gtaaaacgac ggccagtagc 60
gtactctgaa tgccgtcgcc agaaattagt caaggaaa 98